(12) United States Patent
Ponce, Jr. et al.

(10) Patent No.: US 8,852,591 B2
(45) Date of Patent: Oct. 7, 2014

(54) COMBINATION OF BLYS AND/OR APRIL INHIBITION AND IMMUNOSUPPRESSANTS FOR TREATMENT OF AUTOIMMUNE DISEASE

(75) Inventors: Rafael A. Ponce, Jr., Seattle, WA (US); Wayne J. Wallis, Seattle, WA (US); Matthew S. Holdren, Seattle, WA (US); Linda Zuckerman, Seattle, WA (US); Alisa M. Littau, Woodinville, WA (US); Kirk P. Van Ness, Bainbridge Island, WA (US); Claudia Pena Rossi, Geneva (CH); Hans Otto Lennart Graffner, Helsingborg (SE)

(73) Assignee: Zymogenetics, Inc., Seattle, WA (US)

( * ) Notice: Subject to any disclaimer, the term of this patent is extended or adjusted under 35 U.S.C. 154(b) by 283 days.

(21) Appl. No.: 12/057,133

(22) Filed: Mar. 27, 2008

(65) Prior Publication Data

US 2008/0260737 A1 Oct. 23, 2008

Related U.S. Application Data

(60) Provisional application No. 60/908,365, filed on Mar. 27, 2007.

(51) Int. Cl.
*A61K 39/395* (2006.01)
*A61K 38/17* (2006.01)
*A61K 45/06* (2006.01)

(52) U.S. Cl.
CPC ............. *A61K 45/06* (2013.01); *A61K 38/1793* (2013.01)
USPC ..................................... 424/134.1; 424/278.1

(58) Field of Classification Search
CPC ............................ A61K 45/06; A61K 38/1793
See application file for complete search history.

(56) References Cited

U.S. PATENT DOCUMENTS

2005/0163775 A1 * 7/2005 Chan et al. .................. 424/144.1

FOREIGN PATENT DOCUMENTS

| AU | 2006 201 471 | 5/2006 | |
|---|---|---|---|
| JP | 2003-522800 | 11/2000 | |
| JP | 2004-535182 | 5/2002 | |
| JP | 2008-520587 | 6/2008 | |
| WO | 01/60397 | 8/2001 | |
| WO | WO 01/60397 | 8/2001 | |
| WO | 02/094852 | * 11/2002 | |
| WO | WO 02/094852 | 11/2002 | |
| WO | 03/001877 | 1/2003 | |
| WO | WO 03/001877 | 1/2003 | |
| WO | 03/014294 | 2/2003 | |
| WO | WO 03/014294 | 2/2003 | |
| WO | 03/055979 | 7/2003 | |
| WO | WO 03/055979 | 7/2003 | |
| WO | 2006/052493 | 5/2006 | |
| WO | WO 2006/052493 | 5/2006 | |
| WO | WO 2006/053390 | 5/2006 | |
| WO | 2006/068867 | 6/2006 | |
| WO | WO 2006/068867 | 6/2006 | |
| WO | 2007/019618 | 2/2007 | |
| WO | WO 2007/019618 | 2/2007 | |
| WO | WO 2007/134326 | 11/2007 | |
| WO | WO 2009/062960 A1 | 5/2009 | |

OTHER PUBLICATIONS

Berenbaum (Clin Exp. Immunol, 28(1018, 1977).*
Dooley et al (J. Am. Soc. Nephrol. 10:833-839, 1999).*
Jonsson et al (International Immunopharmacology 3:31-37, 2003).*
Ramanujam et al (The Journal of Immunology, 173:3524-3534, 2004).*
Stohl et al (Clinical Immunology, 104(2):115-122, 2002).*
Koyama et al (Ann Rheum Dis 64:1065-1067, 2005).*
Gross et al, (Immunity, 15:289-302, 2001).*
Stein et al (The Journal of Clinical Investigation, 109(12):1587-1598, 2002).*

* cited by examiner

*Primary Examiner* — Patricia A Duffy
(74) *Attorney, Agent, or Firm* — Alston & Bird LLP

(57) ABSTRACT

The invention relates to novel combination therapies involving BLyS or BLyS/APRIL inhibition and immunosuppressants for the treatment of autoimmune diseases. One preferred method is where the BLyS and/or APRIL antagonist is a Fc-fusion protein which can be a TACI-Fc-fusion protein comprising the extracellular domain of TACI or a functional fragment thereof, a BAFF-R-Fc-fusion protein comprising the extracellular domain of BAFF-R or a functional fragment thereof, or a BCMA-Fc-fusion protein comprising the extracellular domain of BCMA or a functional fragment thereof. In the methods of the present invention some of the immunosuppressive drugs contemplated include cyclophosphamide (CYC), azathioprine (AZA), cyclosporine A (CSA), or mycophenolate mofetil (MMF), although any drug that suppresses the immune system may be suitable. The methods of the present invention reduce the levels of various immunoglobulins in patients in need of such reduction, such as those suffering from autoimmune diseases.

14 Claims, 3 Drawing Sheets

COMBINATION OF BLYS AND/OR APRIL INHIBITION AND IMMUNOSUPPRESSANTS FOR TREATMENT OF AUTOIMMUNE DISEASE

CROSS-REFERENCE TO RELATED APPLICATIONS

The present application claims the benefit of U.S. Provisional Patent Application Nos. 60/908,365, filed Mar. 27, 2007, which is herein incorporated by reference in its entirety.

FIELD OF THE INVENTION

The invention relates to novel combination therapies involving BLyS or BLyS/APRIL inhibition and immunosuppressants for the treatment of autoimmune diseases.

BACKGROUND OF THE INVENTION

Lymphocytes are one of several populations of white blood cells; they specifically recognize and respond to foreign antigen. The three major classes of lymphocytes are B lymphocytes (B cells), T lymphocytes (T cells) and natural killer (NK) cells. B lymphocytes are the cells responsible for antibody production and provide humoral immunity. B cells mature within the bone marrow and leave the marrow expressing an antigen-binding antibody on their cell surface. When a naive B cell first encounters the antigen for which its membrane-bound antibody is specific, the cell begins to divide rapidly and its progeny differentiate into memory B cells and effector cells called plasma cells. Memory B cells have a longer life span and continue to express membrane-bound antibody with the same specificity as the original parent cell. Plasma cells do not produce membrane-bound antibody but instead produce secreted form of the antibody. Secreted antibodies are the major effector molecules of humoral immunity.

A group of tumor necrosis factor (TNF) receptors found on the surface of B cells under various conditions are among the cellular regulators of B cell function in the immune system. In particular, three TNF receptors: transmembrane activator and CAML interactor (TACI), B cell activator belonging to the TNF family receptor (BAFF-R), and B cell maturation protein (BCMA) are known to bind one or both TNF ligands-Lymphocyte stimulator (BLyS also known as BAFF, TALL-1, ztnf4 and THANK) and a proliferation-inducing ligand (APRIL). Specifically, TACI and BCMA are known to bind both BLyS and APRIL and BAFF-R binds only BLyS.

A number of BLyS and/or APRIL antagonists have been developed in order to block the various functions of BLyS, which include but should not be limited to B cell co-stimulation, plasmablast and plasma cell survival, Ig class switching, enhanced B-cell antigen presenting cell function, survival of malignant B cells, development of B-1 cell function, B cell development beyond the T-1 stage, and complete germinal centre formation Some of these molecules can also bind to and block the effect of APRIL on B cells and other components of the immune system (Dillon et al. (2006) Nat. Rev. Drug Dis. 5, 235-246). Molecules that have been developed to affect B cell function by interfering with BLyS and/or APRIL binding include BLyS antibodies such as Lymphostat-B (Belimumab) (Baker et al, (2003) Arthritis Rheum, 48, 3253-3265 and WO 02/02641); receptor-extracellular domain/Fc domain fusions proteins such as TACI-Ig, including one particular embodiment, atacicept (U.S. Patent Application No. 20060034852), BAFF-R-Fc (WO 05/0000351), and BCMA-Ig or other fusion proteins utilizing receptor extracellular domains. A further class of BLyS and/or APRIL antagonists include other molecules relying on BLyS binding ability to block binding to its receptors such as AMG 623, receptor antibodies, and other molecules disclosed in WO 03/035846 and WO 02/16312

The current approach for the treatment of autoimmune diseases is suppression of the unwanted immune reaction. For example, in the treatment of lupus nephritis (LN), a serious complication involving the kidney of patients suffering from systemic lupus nephritis (SLE), several immunosuppressive drugs have proven beneficial. These drugs include cyclophosphamide (CYC), azathioprine (AZA), cyclosporine A (CSA), and mycophenolate mofetil (MMF) (for general reviews see, Mok et al. (2003) Ann Rheum Dis 62, 799-804 and Iaccarino et al. (2007) Autoimmunity Reviews 6, 190-195). Although these drugs are beneficial, there remains a need in the art to improve the response to immune suppressive drugs in order to effectively treat autoimmune disease.

SUMMARY OF THE INVENTION

One aspect of the present invention is a method of reducing immunoglobulin levels in a mammal comprising administering a BLyS and/or APRIL antagonist and an immunosuppressive drug. One preferred method is where the BLyS and/or APRIL antagonist is a Fc-fusion protein which can be a TACI-Fc-fusion protein comprising the extracellular domain of TACI or a functional fragment thereof, a BAFF-R-Fc-fusion protein comprising the extracellular domain of BAFF-R or a functional fragment thereof, or a BCMA-Fc-fusion protein comprising the extracellular domain of BCMA or a functional fragment thereof. In particular, the Fc-fusion protein comprises the polypeptide sequences of SEQ ID NO: 19, SEQ ID NO: 21, SEQ ID NO: 23, SEQ ID NO: 25, or SEQ ID NO: 26.

In another embodiment, the BLyS and/or APRIL antagonist is a BLyS antibody, preferably that binds BLyS within a region comprising amino acids 162-275 of SEQ ID NO: 8, or the BLyS antibody known as LymphoStat-B. In further embodiment, the BLyS and/or APRIL antagonist is a TACI antibody, preferably that binds TACI within a region comprising 72-109 of SEQ ID NO:2 or 82-222 of SEQ ID NO:2.

In the methods of the present invention some of the immunosuppressive drugs contemplated include cyclophosphamide (CYC), azathioprine (AZA), cyclosporine A (CSA), or mycophenolate mofetil (MMF), although any drug that suppresses the immune system may be suitable. The immunoglobulin level that is reduced by the present method can be IgM, IgG, IgA, IgD or IgE or combinations thereof The present invention also encompasses a method of alleviating a B-cell regulated autoimmune disorders comprising administering to a patient suffering from the disorder, a therapeutically effective amount of an immunosuppressive drug and of a BLyS and/or APRIL antagonist. In one embodiment, the autoimmune disorder is selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis. One disease specifically treated in this manner is lupus nephritis.

Particularly when the autoimmune disorder is rheumatoid arthritis, systemic lupus erythematosus, or lupus nephritis, in one embodiment, the BLyS and/or APRIL antagonist and the immunosuppressive drug can be administered in further conjunction with therapy using a second immunosuppressive drug such as nonsteroidal anti-inflammatory drugs (NSAIDs), glucocorticoid, prednisone, and disease-modifying antirheumatic drug (DMARD).

The methods of the present invention utilize immunosuppressive drugs which have been shown to be effective in treating autoimmune disease in combination with the BLyS and/or APRIL antagonist. Among the immunosuppressive drugs contemplated for use in the methods of the present invention are cyclophosphamide (CYC), azathioprine (AZA), cyclosporine A (CSA), and mycophenolate mofetil (MMF).

In any of the methods of treatment or alleviation of a disorder where the immunosuppressive drug and the BLyS and/or APRIL antagonist are administered to a patient, the immunosuppressive drug and BLyS and/or APRIL antagonist can be administered concurrently or sequentially. In a specific embodiment, the immunosuppressive agent is administered before BLyS and/or APRIL antagonist A composition comprising an immunosuppressive agent and a BLyS and/or APRIL antagonist is also provided.

Further provided by the invention is an article of manufacture comprising an immunosuppressive agent, a BLyS and/or APRIL antagonist, and a label wherein the label indicates that the composition is for treating a B cell regulated autoimmune disorder.

In any of the embodiments of the methods, compositions and articles of manufacture of the invention, the BLyS and/or APRIL antagonist, if an antibody, includes chimeric and humanized antibodies.

In any of the embodiments of the methods, compositions and articles of manufacture of the invention, the BLyS and/or APRIL antagonist, in one embodiment, is a fusion protein between the extracellular domain of a receptor that binds BLyS and the Fc domain of an immunoglobulin, or an Fc-fusion protein. In specific embodiments, the Fc-fusion protein selected from the group consisting of TACI Fc-fusion protein comprising the extracellular domain of TACI, in particular atacicept, BAFF-R Fc-fusion protein comprising the extracellular domain of BAFF-R, in particular BR3-Ig, and BCMA Fc-fusion protein comprising the extracellular domain of BCMA. In other embodiments, the BLyS and/or APRIL antagonist is a BLyS antibody, in particular, a BLyS antibody that binds BLyS within a region of BLyS comprising residues 162-275, in particular Lymphostat B. In another embodiment, the BLyS and/or APRIL antagonist is a BAFF-R antibody including one that binds in a region comprising residues 23-38 of human BAFF-R. In another embodiment, the BLyS and/or APRIL antagonist is a TACI antibody, a BCMA antibody, or an antibody that binds both molecules as described in U.S. Patent Application No. 2003-0012783.

DETAILED DESCRIPTION OF THE PREFERRED EMBODIMENTS

Figure 1:
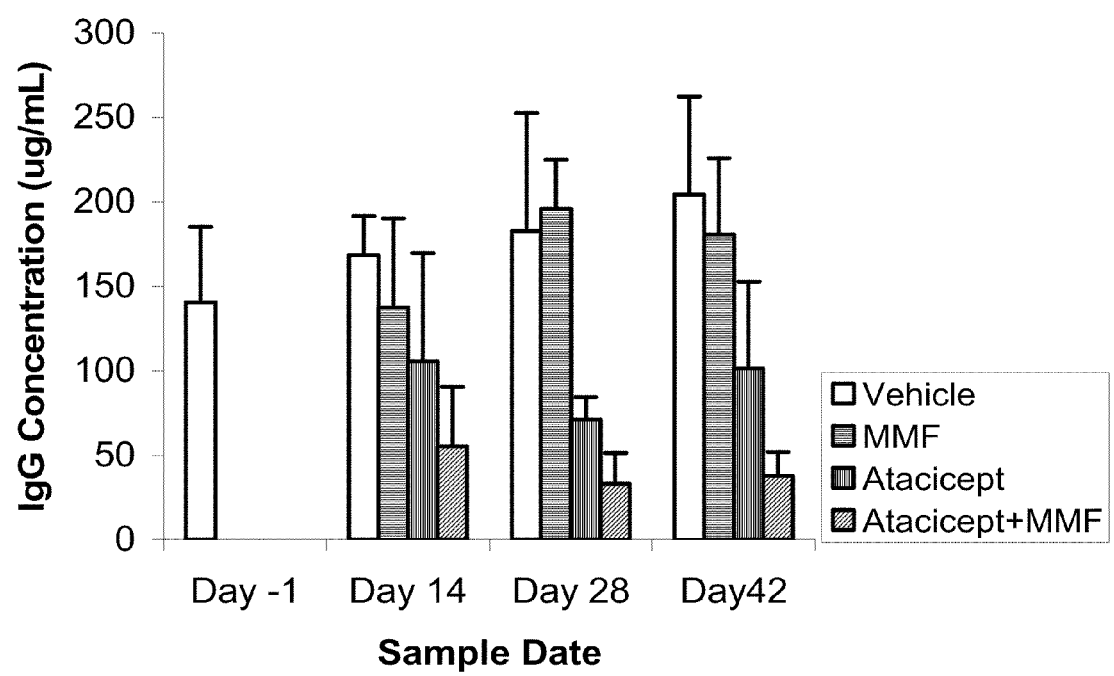
FIG. 1 graphs the mean value (±standard deviation) of IgG for the four treatment groups—vehicle, MMF only, atacicept only, and atacicept and MMF. All pairwise comparisons of these values were statistically significant (p<0.05) using log-transformed data other than vehicle vs. MMF alone.

While immunosuppressive treatment appears useful in the treatment of autoimmune disease, it was discovered from the experiments described herein that administration of a combination of immunosuppressives with a BLyS and/or APRIL antagonist is a method of treatment that will block multiple signal pathways in B cells believed responsible for the production of antibodies directed at self-antigens, thereby triggering and/or perpetuating the autoimmune condition. This results in a reduction of circulating immunoglobulin in a mammal undergoing such treatment. As such circulating immunoglobulin is believed at least partially responsible for triggering the negative symptoms of autoimmune disease, the combination of immunesuppressive drugs and therapies directed against the BLyS pathway therefore provides a novel method of treating B cell-mediated diseases such as B cell-based autoimmune diseases. The combination therapy of immunesuppressive drugs with a BLyS and/or APRIL antagonist may offer more effective alternatives to existing treatments for certain diseases, e.g., lupus nephritis.

An "autoimmune disease" herein is any non-malignant disease or disorder arising from antibodies that are produced directed against an individual's own (self) antigens and/or tissues.

As used herein, "B cell depletion" refers to a reduction in B cell levels in an animal or human after drug or antibody treatment, as compared to the level before treatment. B cell levels are measurable using well known assays such as by getting a complete blood count, by FACS analysis staining for known B cell markers, and by methods such as described in the Experimental Examples. B cell depletion can be partial or complete. In a patient receiving a B cell depleting drug, B cells are generally depleted for the duration of time when the drug is circulating in the patient's body and the time for recovery of B cells.

"Immunosuppressive drugs" are any molecules that interfere with the immune system and blunt its response to foreign or self antigens. Cyclophosphamide (CYC) and mycophenolate mofetil (MMF) are two such kinds of molecules. This term is intended to encompass any drug or molecule useful as a therapeutic agent in downregulating the immune system. This method particularly contemplates drugs that have been used to treat autoimmune diseases such as rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis.

The terms "BLyS" or "BLyS polypeptide," "TALL-1" or "TALL-1 polypeptide," or "BAFF" or "BAFF polypeptide" when used herein encompass "native sequence BLyS polypeptides" and "BLyS variants." "BLyS" is a designation given to those polypeptides which are encoded by the Human BLyS sequence (SEQ ID NO: 7) or the Mouse BLyS sequence (SEQ ID NO: 9). Polypeptides which show BLyS biological activity are encompassed within this designation as well. For example, a biologically active BLyS potentiates any one or combination of the following events in vitro or in vivo: an increased survival of B cells, an increased level of IgGand/or IgM, an increased numbers of plasma cells, and processing of NF-Kb2/100 to p 52NF-Kb in splenic B cells (e.g., Batten, M et al., (2000) J. Exp. Med. 192: 1453-1465; Moore, et al., (1999) Science 285: 260-263; Kayagaki, et al., (2002) 10: 515-524). Several assays useful for testing BLyS and/or APRIL antagonists such as the B cell proliferation assay described in WO 00/40716 among others are well known to one of ordinary skill in the art.

Briefly, human B cells are isolated from peripheral blood mononuclear cells using CD19 magnetic beads and the VarioMacs magnetic separation system (Miltenyi Biotec Auburn, Calif.) according to the manufacturer's instructions. Purified B cells are mixed with soluble BLyS (25 ng/ml) and recombinant human IL-4 (10 ng/ml Pharmingen), and the cells are plated onto round bottom 96 well plates at $1 \times 10^5$ cells per well. The BLyS and/or APRIL antagonist to be tested can be diluted from about 5 µg/ml to about 6 ng/ml, and incubated with the B cells for five days, pulsing overnight on day four with 1 µCi $^3$H-thymidine per well. As a control, BLyS and/or APRIL antagonist can also be incubated with B cells and IL-4 without BLyS. Plates are harvested using Packard plate harvester, and counted using the Packard reader.

A "native sequence" polypeptide comprises a polypeptide having the same amino acid sequence as the corresponding polypeptide derived from nature. Such native sequence polypeptides can be isolated from nature or can be produced by recombinant and/or synthetic means. The term "native sequence" specifically encompasses naturally-occurring truncated, soluble or secreted forms (e.g., an extracellular domain sequence), naturally-occurring variant forms (e.g., alternatively spliced forms) and naturally-occurring allelic variants of the polypeptide.

In general, "variant" polypeptides for any of the polypeptides disclosed in the present specification include polypeptides wherein one or more amino acid residues are added or deleted at the N- and/or C-terminus, as well as within one or more internal domains, of the full-length or "native sequence" amino acid sequence. When discussing extracellular domains of receptors, fragments that bind a native sequence BlyS polypeptide are also contemplated. Conversely, when discussing BLyS fragments, fragments that bind any one or more of the three BLyS receptors are contemplated. Ordinarily, a variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with the polypeptide or a specified fragment thereof. Generally, variant polypeptides do not encompass the native polypeptide sequence. Ordinarily, variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, or more.

As mentioned above, a BLyS and/or APRIL antagonist can function in a direct or indirect manner to partially or fully block, inhibit or neutralize BLyS signaling, in vitro or in vivo. For instance, the BLyS and/or APRIL antagonist can directly bind BLyS. For example, a direct binder is a polypeptide comprising the extracellular domain (ECD) of a BLyS receptor such as TACI, BAFF-R, and BCMA.

The BLyS receptors involved in the present invention can be described as follows. The TACI polypeptides of the invention include TACI polypeptides comprising or consisting of amino acids 1-246 of SEQ ID NO: 2. The general term "TACI" includes the TACI polypeptides described in WO 98/39361, WO 00/40716, WO 01/85782, WO 01/87979, WO 01/81417, and WO 02/094852. The TACI polypeptides of the invention can be isolated from a variety of sources, such as from human tissue types or from another source, or prepared by recombinant and/or synthetic methods. The BAFF-R polypeptides of the invention include the BAFF-R polypeptide comprising or consisting of the contiguous sequence of amino acid residues 1 to 184 of SEQ ID NO:4. The general term "BAFF-R" includes the BAFF-R polypeptides described in WO 02/24909 and WO 03/14294. The BAFF-R polypeptides of the invention can be isolated from a variety of sources, such as from human tissue types or from another source, or prepared by recombinant and/or synthetic methods. The BCMA polypeptide of the invention include BCMA polypeptides comprising or consisting of amino acid residues 1-184 of SEQ ID NO:6. The general term "BCMA" includes the BCMA polypeptides described in Laabi et al., EMBO J., 11: 3897-3904 (1992); Laabi et al., Nucleic Acids Res., 22: 1147-1154 (1994); Gras et al., Int. Immunology, 7: 1093-1106 (1995); and Madry et al., Int. Immunology, 10: 1693-1702 (1998). The BCMA polypeptides of the invention can be isolated from a variety of sources, such as from human tissue types or from another source, or prepared by recombinant and/or synthetic methods.

For the purposes of functioning as a BLyS and/or APRIL antagonist, the ECD of these receptors is a polypeptide essentially free of the transmembrane or cytoplasmic domains that generally retains the ability to bind BLyS. Specifically, the extracellular domain of TACI can comprise amino acids 1 to 154 of the TACI polypeptide sequence (SEQ ID NO: 2). Additionally, the ECD can be fragments or variants of this sequence, such as ECD forms of TACI as described in von Bulow et al., supra, WO 98/39361, WO 00/40716, WO 01/85782, WO 01/87979, and WO 01/81417. In particular, these ECD forms can comprise amino acids 1-106 of SEQ ID NO:2, amino acids 1-142 of SEQ ID NO:2, amino acids 30-154 of SEQ ID NO:2, amino acids 30-106 of SEQ ID NO:2, amino acids 30-110 of SEQ ID NO:2, amino acids 30-119 of SEQ ID NO:2, amino acids 1-166 of SEQ ID NO:2, amino acids 1-165 of SEQ ID NO:2, amino acids 1-114 of SEQ ID NO: 2, amino acids 1-119 of SEQ ID NO:2, amino acids 1-120 of SEQ ID NO:2, and amino acids 1-126 of SEQ ID NO:2. In addition, the TACI ECD can comprise those molecules having only one cysteine rich domain ECD forms of BAFF-R include those comprising amino acids 1-71 of the BAFF-R polypeptide sequence (SEQ ID NO: 4). Additionally, the ECD can be fragments or variants of this sequence such as ECD forms of BAFF-R as described in WO 02/24909, WO 03/14294, and WO 02/38766. In particular, these ECD forms can comprise amino acids 1-77 of SEQ ID NO: 4, amino acids 7-77 of SEQ ID NO:4, amino acids 1-69 of SEQ ID NO:4, amino acids 7-69 of SEQ ID NO:4, amino acids 2-62 of SEQ ID NO:4, amino acids 2-71 of SEQ ID NO:4, amino acids 1-61 of SEQ ID NO:4 and amino acids 2-63 of SEQ ID NO:4, amino acids 1-45 of SEQ ID NO:4, amino acids 1-39 of SEQ ID NO:4, amino acids 7-39 of SEQ ID NO:4, amino acids 1-17 of SEQ ID NO:4, amino acids 39-64 of SEQ ID NO:4, amino acids 19-35 of SEQ ID NO:4, and amino acids 17-42 of SEQ ID NO:4. In addition, the BAFF-R ECD can comprise those molecules having a cysteine rich domain.

ECD forms of BCMA include those comprising amino acids 1-48 of the BCMA polypeptide sequence (SEQ ID NO: 6). Additionally, the ECD can be fragments or variants of this sequence, such as ECD forms of BCMA as described in WO 00/40716 and WO 05/075511. In particular, these ECD forms can comprise amino acids 1-150 of SEQ ID NO:6, amino acids 1-48 of SEQ ID NO:6, amino acids 1-41 of SEQ ID NO:6, amino acids 8-41 of SEQ ID NO:6, amino acids 8-37 of SEQ ID NO:6, amino acids 8-88 of SEQ ID NO:6, amino acids 41-88 of SEQ ID NO:6, amino acids 1-54 of SEQ ID NO:6, amino acids 4-55 of SEQ ID NO:6, amino acids 4-51 of SEQ ID NO:6, and amino acids 21-53 of SEQ ID NO:6. In addition, the BCMA ECD can comprise those molecules having only a partial cysteine rich domain.

In a further embodiment, the BLyS binding region of a BLyS receptor (e.g., an extracellular domain or fragment thereof of BAFF-R, BCMA or TACI) can be fused to an Fc portion of an immunoglobulin molecule to facilitate its solubility in vivo. According to one embodiment, the BLyS and/or APRIL antagonist binds to a BLyS polypeptide with a binding affinity of 100 nM or less. According to another embodiment, the BLyS and/or APRIL antagonist binds to a BLyS polypeptide with a binding affinity of 10 nM or less. According to yet another embodiment, the BLyS and/or APRIL antagonist binds to a BLyS polypeptide with a binding affinity of 1 nM or less.

In another example, BLyS and/or APRIL antagonists include BLyS binding polypeptides that are not native sequences or varients thereof. Some examples of such polypeptides are those having the sequence of Formula I, Formula II, Formula III as described in WO 05/000351. In particular, some binding polypeptides include ECFDLLVRAWVPCSVLK (SEQ ID NO:13), ECFDLLVRHWVPCGLLR (SEQ ID NO:14), ECFDLLVR-RWVPCEMLG (SEQ ID NO:15), ECFDLLVRSWVPCH-MLR (SEQ ID NO:16), ECFDLLVRHWVACGLLR (SEQ ID NO:17), or sequences listed in FIG. 32 of WO 05/000351.

Alternatively, the BLyS and/or APRIL antagonist can bind an extracellular domain of native sequence TACI, BAFF-R, or BCMA at its BLyS binding region to partially or fully block, inhibit or neutralize BLyS binding in vitro, in situ, or in vivo. For example, such indirect antagonist is a TACI antibody that binds in a region of TACI such that the binding of BLyS is sterically hindered. For example, binding at amino acids 72-109 or a neighboring region is believed to block BLyS binding. It could also be advantageous to block APRIL binding to this molecule, which is believed to occur in the region of amino acids 82-222. Another BLyS and/or APRIL antagonist is a BAFF-R antibody that binds in a region of BAFF-R such that binding of human BAFF-R to BLyS is sterically hindered. For example, binding at amino acids 23-38 or amino acids 17-42 or a neighboring region is believed to block BLyS binding. Finally, a further indirect antagonist would be a BCMA antibody that binds in a region of BCMA such that the binding of BLyS is sterically hindered. For example, binding at amino acids 5-43 or a neighboring region is believed to block BLyS (or APRIL) binding.

In some embodiments, a BLyS and/or APRIL antagonist according to this invention includes BLyS antibodies. The term "antibody" when referring to is used in the broadest sense and specifically covers, for example, monoclonal antibodies, polyclonal antibodies, antibodies with polyepitopic specificity, single chain antibodies, and fragments of antibodies. According to some embodiments, a polypeptide of this invention is fused into an antibody framework, for example, in the variable region or in a CDR such that the antibody can bind to and inhibit BLyS binding to TACI, BAFF-R, or BCMA or inhibits BLyS signaling. The antibodies comprising a polypeptide of this invention can be chimeric, humanized, or human. The antibodies comprising a polypeptide of this invention can be an antibody fragment. Alternatively, an antibody of this invention can be produced by immunizing an animal with a polypeptide of this invention. Thus, an antibody directed against a polypeptide of this invention is contemplated.

In particular, antibodies specific for BLyS that bind within a region of human BLyS (SEQ ID NO: 8) comprising residues 162-275 and/or a neighboring amino acid of amino acids selected from the group consisting of 162, 163, 206, 211, 231, 233, 264 and 265 of human BLyS are contemplated. The binding of the antibodies are such that the antibody sterically hinders BLyS binding to one or more of its receptors. Such antibodies are described in WO 02/02641 and WO 03/055979. A particularly preferred antibody is the one described as Lyphostat-B (Baker et al. (2003) Arthritis Rheum, 48, 3253-3265).

The term "monoclonal antibody" as used herein refers to an antibody obtained from a population of substantially homogeneous antibodies, i.e., the individual antibodies comprising the population are identical except for possible naturally occurring mutations that can be present in minor amounts.

Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Methods of making chimeric antibodies are known in the art.

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin.

For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992). The humanized antibody includes a PRIMATIZED antibody wherein the antigen-binding region of the antibody is derived from an antibody produced by, e.g., immunizing macaque monkeys with the antigen of interest. Methods of making humanized antibodies are known in the art.

Human antibodies can also be produced using various techniques known in the art, including phage-display libraries. Hoogenboom and Winter, J. Mol. Biol., 227: 381 (1991); Marks et al., J. Mol. Biol., 222: 581 (1991). The techniques of Cole et al. and Boerner et al. are also available for the preparation of human monoclonal antibodies. Cole et al., Monoclonal Antibodies and Cancer Therapy, Alan R. Liss, p. 77 (1985); Boerner et al., J. Immunol., 147(1): 86-95 (1991).

"Functional fragments" of the binding antibodies of the invention are those fragments that retain binding to BLyS, TACI, BAFF-R, or BCMA with substantially the same affinity as the intact full chain molecule from which they are derived and may be able to deplete B cells as measured by in vitro or in vivo assays such as those described herein.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing-target cell and subsequently kill the-target cell with cytotoxins. The antibodies—"arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Ann. Rev. Immunol 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95: 652-656 (1998).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

Isolated antibody includes the antibody insitu within recombinant cells since at least one component of the antibody's natural environment will not be present. Ordinarily, however, isolated antibody will be prepared by at least one purification step.

Amino acids may be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M) (2) uncharged polar: Gly (G), Ser (S), Thr (T), Cys (C), Tyr (Y), Asn (N) Gln (Q) (3) acidic: Asp (D), Glu (E) (4) basic: Lys(K), Arg (R), His (H—)

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: H is, Lys, Arg; (5) residues that influence chain orientation: Gly, Pro; (6) aromatic: Trp, Tyr, Phe.

The term "conservative" amino acid substitution as used within this invention is meant to refer to amino acid substitutions which substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. In general, substitutions within a group may be considered conservative with respect to structure and function. However, the skilled artisan will recognize that the role of a particular residue is determined by its context within the three-dimensional structure of the molecule in which it occurs. For example, Cys residues may occur in the oxidized (disulfide) form, which is less polar than the reduced (thiol) form. The long aliphatic portion of the Arg side chain may constitute a critical feature of its structural or functional role, and this may be best conserved by substitution of a nonpolar, rather than another basic residue. Also, it will be recognized that side chains containing aromatic groups (Trp, Tyr, and Phe) can participate in ionic-aromatic or "cation-pi" interactions. In these cases, substitution of one of these side chains with a member of the acidic or uncharged polar group may be conservative with respect to structure and function. Residues such as Pro, Gly, and Cys (disulfide form) can have direct effects on the main chain conformation, and often may not be substituted without structural distortions.

"Percent (%) amino acid sequence identity" with respect to the ligand or receptor polypeptide sequences identified herein is defined as the percentage of amino acid residues in a candidate sequence that are identical with the amino acid residues in such a ligand or receptor sequence identified herein, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in the table below. The ALIGN-2 sequence comparison computer program was authored by Genentech, Inc. and the source code shown in the table below has been filed with user documentation in the U.S. Copyright Office, Washington D.C., 20559, where it is registered under U.S. Copyright Registration No. TXU510087. The ALIGN-2 program is-publicly available through Genentech, Inc., South San Francisco, Calif. or can be compiled from the source code provided in the table below. The ALIGN-2 program should be compiled for use on a UNIX operating system, preferably digital UNIX V4.0D. All sequence comparison parameters are set by the ALIGN-2 program and do not vary.

A useful method for identification of certain residues or regions in a protein that are preferred locations for mutagenesis is called "alanine scanning mutagenesis" as described by Cunningham and Wells Science, 244: 1081-1085 (1989). A residue or group of target residues are identified (e.g., charged residues such as arg, asp, his, lys, and glu) and replaced by a neutral or negatively charged amino acid (most preferably alanine or polyalanine) to affect the interaction of the amino acids with a binding target. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed variants are screened for the desired activity.

The term, "dihedral angle" refers to a rotation about a bond. See e.g., Creighton, T. E., (1993) Protein: Structures and Molecular Properties, 2 ed., W. H. Freeman and Company, New York, N.Y. The term, "phi," is a dihedral angle that denotes a rotation about the N—C bond of an amino acid. See e.g., Creighton, T. E., (1993) Protein: Structures and Molecular Properties, 2 ed., W. H. Freeman and Company, New York, N.Y. Type I beta turns are described in Hutchinson, E. G. & Thornton, J. M. (1994) A revised set of potentials for beta turn formation in proteins. Protein Science 3, 2207-2216.

A "fusion protein" and a "fusion polypeptide" refer to a polypeptide having two portions covalently linked together, where each of the portions is a polypeptide having a different property. The property may be a biological property, such as activity in vitro or in vivo. The property may also be a simple chemical or physical property, such as binding to a target molecule, catalysis of a reaction, etc. The two portions may be linked directly by a single peptide bond or through a peptide linker containing one or more amino acid residues. Generally, the two portions and the linker will be in reading frame with each other.

A "conjugate" refers to any hybrid molecule, including fusion proteins and as well as molecules that contain both amino acid or protein portions and non-protein portions. Conjugates may be synthesized by a variety of techniques known in the art including, for example, recombinant DNA techniques, solid phase synthesis, solution phase synthesis, organic chemical synthetic techniques or a combination of these techniques. The choice of synthesis will depend upon the particular molecule to be generated. For example, a hybrid molecule not entirely "protein" in nature may be synthesized by a combination of recombinant techniques and solution phase techniques.

As used herein, the term "Fc-fusion protein" designates antibody-like molecules which combine the binding specificity of a heterologous protein with the effector functions of immunoglobulin constant domains. Structurally, the Fc-fusion proteins comprise a fusion of an amino acid sequence with the desired binding specificity which is other than the antigen recognition and binding site of an antibody (i.e., is "heterologous"), and an immunoglobulin constant domain sequence. The Fc-fusion protein molecule typically includes a contiguous amino acid sequence comprising at least the binding site of a receptor or a ligand. The immunoglobulin constant domain sequence in the Fc-fusion protein can be obtained from any immunoglobulin, such as IgG-1, IgG-2, IgG-3, or IgG-4 subtypes, IgA (including IgA-1 and IgA-2), IgE, IgD or IgM. For example, useful Fc-fusion proteins according to this invention are polypeptides that comprise the BLyS binding portions of a BLyS receptor without the transmembrane or cytoplasmic sequences of the BLyS receptor. In one embodiment, the extracellular domain of BAFF-R, TACI or BCMA is fused to a constant domain of an immunoglobulin sequence.

The term "mammal" refers to any animal classified as a mammal, including humans, domestic and farm animals, and zoo, sports, or pet animals, such as dogs, horses, cats, cows, etc. Preferably, the mammal herein is human.

The term "therapeutically effective amount" refers to an amount of an antibody or a antagonist drug effective to "alleviate" or "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition of "treated" below. To the extent the drug may prevent growth and/or kill existing cancer cells, it may be cytostatic and/or cytotoxic.

The BLyS or BLyS receptor antibodies of the invention can be produced by transient or stable transfection eukaryotic host cells such as CHO cells.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN polyethylene glycol(PEG), and PLURONICS™.

Polynucleotides, Vectors, Host Cells

According to a number of embodiments disclosed herein, the BLyS and/or APRIL antagonist can comprise specific polypeptides that are produced using specific polynucleotides in specific vectors and using specific host cells. The various types of polypeptides of the present invention can be broadly described and are selected from the group consisting of receptor-based sequences, antibody-based sequences, and artificial (i.e., non-native) binding sequences. Examples of the receptor-based sequences are those sequences that bind BLyS that were isolated from or derived from domains of the receptors that bind BLyS in vivo, such as TACI, BAFF-R, or BCMA. Antibody-based sequences are those that are produced using antibody development technology and maintain the general structure of an antibody molecule. Examples of antibody-based sequences are LymphoStat-B, or antibodies to receptors of BLyS. Examples of the artificial binding sequences include the 17mer peptides described herein, polypeptides incorporating one or more 17mer peptides as core regions, and covalently modified forms of the 17 mer peptides and polypeptides (e.g., Fc-fusion proteins, labeled polypeptides, protected polypeptides, conjugated polypeptides, fusion proteins, etc.). Various techniques that are employed for making these forms of polypeptides are described herein. Methods for labeling polypeptides and conjugating molecules to polypeptides are known in the art.

Compositions of the invention can be prepared using recombinant techniques known in the art.

The description below relates to methods of producing such specific polypeptides by culturing host cells transformed or transfected with a vector containing the encoding nucleic acid and recovering the polypeptide from the cell culture. (See, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995)).

The nucleic acid (e.g., cDNA orgenomic DNA) encoding the desired polypeptide may be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that may be employed are known in the art and described in further detail in WO 97/25428.

Expression and cloning vectors usually contain a promoter that is recognized by the host organism and is operably linked to the encoding nucleic acid sequence. Promoters are untranslated sequences located upstream (5') to the start codon of a structural gene (generally within about 100 to 1000 bp) that control the transcription and translation of a particular nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to the encoding DNA by removing the promoter from the source DNA by restriction enzyme digestion and inserting the isolated promoter sequence into the vector.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures can be used to transform E. coli K12 strain 294 (ATCC 31,446) and successful transformants selected by ampicillin or tetracycline resistance where appropriate. Plasmids from the transformants are prepared, analyzed by restriction endonuclease digestion, and/or sequenced using standard techniques known in the art. [See, e.g., Messing et al., Nucleic Acids Res., 9: 309 (1981); Maxam et al., Methods in Enzymology, 65: 499 (1980)].

Expression vectors that provide for the transient expression in mammalian cells of the encoding DNA may be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties.

Other methods, vectors, and host cells suitable for adaptation to the synthesis of the desired polypeptide in recombinant vertebrate cell culture are described in Gething et al., Nature, 293: 620-625 (1981); Mantei et al., Nature, 281: 40-46 (1979); EP 117,060; and EP 117,058.

Suitable host cells for cloning or expressing the DNA in the vectors herein include prokaryote, yeast, or higher eukaryote cells. Suitable prokaryotes for this purpose include but are not limited to eubacteria, such as Gram-negative or Gram-positive organisms, for-example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Preferably, the host cell should secrete minimal amounts of proteolytic enzymes.

In addition to prokaryotes, eukaryotic microbes such as filamentous fungi or yeast are suitable cloning or expression hosts for vectors. Suitable host cells for the expression of glycosylated polypeptide are derived from multicellular organisms. Examples of all such host cells are described further in WO97/25428.

Host cells are transfected and preferably transformed with the above-described expression or cloning vectors and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO4 and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23: 315 (1983) and WO 89/05859 published 29 Jun. 1989. In addition, plants may be transfected using ultrasound treatment as described in WO 91/00358 published 10 Jan. 1991.

For mammalian cells without such cell walls, the calcium phosphate precipitation method of Graham and van der Eb, Virology, 52: 456-457 (1978) may be employed. General aspects of mammalian cell host system transformations have been described in U.S. Pat. No. 4,399,216. Transformations into yeast are typically carried out according to the method of Van Solingen et al., J. Bact., 130: 946 (1977) and Hsiao et al., Proc. Natl. Acad. Sci. (USA), 76: 3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185: 527-537 (1990) and Mansour et al., Nature, 336: 348-352 (1988).

Prokaryotic cells can be cultured in suitable culture media as described generally in Sambrook et al., supra. Examples of commercially available culture media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), -trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, Ore those previously used with the host cell selected for expression, and will be apparent to the ordinarily skilled artisan.

In general, principles, protocols, and practical techniques for maximizing the productivity of mammalian cell cultures can be found in Mammalian Cell Biotechnology: A Practical Approach, M. Butler, ed. (IRL Press, 1991).

The expressed polypeptides may be recovered from the culture medium as a secreted polypeptide, although may also be recovered from host cell lysates when directly produced without a secretory signal. If the polypeptide is membrane-bound, it can be released from the membrane using a suitable detergent solution (e.g. Triton-X 100) or its extracellular region may be released by enzymatic cleavage.

When the polypeptide is produced in a recombinant cell other than one of human origin, it is free of proteins or polypeptides of human origin. However, it is usually necessary to recover or purify the polypeptide from recombinant cell proteins or polypeptides to obtain preparations that are substantially homogeneous. As a first step, the culture medium or lysate may be centrifuged to remove particulate cell debris. The following are procedures exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

Phage Display

According to some embodiments, the polypeptides of this invention selected from the group consisting of: Formula I, Formula II, Formula III, ECFDLLVRAWVPCSVLK (SEQ ID NO:13), ECFDLLVRHWVPCGLLR (SEQ ID NO:14), ECFDLLVRRWVPCEMLG (SEQ ID NO:15), ECFDLLVR-SWVPCHMLR (SEQ ID NO:16), ECFDLLVRHW-VACGLLR (SEQ ID NO:17), and sequences listed in FIG. 32 of WO 05/000351, may utilized in phage display.

Using the techniques of phage display allows the generation of large libraries of protein variants which can be rapidly sorted for those sequences that bind to a target molecule with high affinity. Nucleic acids encoding variant polypeptides are fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S., Proteins, 8: 309 (1990); Lowman and Wells, Methods: A Companion to Methods in Enzymology, 3: 205 (1991)). In a monovalent phage display system, the gene fusion is expressed at low levels and wild type gene III proteins are also expressed so that infectivity of the particles is retained. Methods of generating peptide libraries and screening those libraries have been disclosed in many patents (e.g.

U.S. Pat. No. 5,723,286; U.S. Pat. No. 5,432,018; U.S. Pat. No. 5,580,717; U.S. Pat. No. 5,427,908; and U.S. Pat. No. 5,498,530).

In some embodiments, Formula I, Formula II or Formula III are expressed as peptide libraries on phage. The phage expressing the library of polypeptides of Formula I, Formula II or Formula III are then subjected to selection based on BLyS binding. In some embodiments, the selection process involves allowing some phage bind to biotinylated BLyS which is subsequently bound to a neutravidin plate. Phage bound to the plate through the BLyS-biotin-neutravidin binding are recovered and propogated. In some embodiments, the phage are subject to several rounds of selection. In some embodiments, the phage is incubated with BLyS-biotin, followed by the addition of unbiotinylated BLyS as a competitive binder.

Additional guidance of use of phage display in the context of the present invention is provided in the Examples.

Polypeptides Fused or Conjugated to Heterologous Polypeptides

Fc-fusion protein molecules comprising the polypeptides of this invention are further contemplated for use in the methods herein. In some embodiments, the molecule comprises a fusion of a polypeptide of this invention with an immunoglobulin or a particular region of an immunoglobulin. For a bivalent form of the Fc-fusion protein, such a fusion usefully comprises the Fc region of an IgG molecule. In a further embodiment, the Fc region is from a human IgG1 molecule. In some embodiments, the immunoglobulin fusion includes the hinge, CH2 and CH3, or the hinge, CH1, CH2 and CH3 regions of an IgG1 molecule.

For the production of immunoglobulin fusions, see also U.S. Pat. No. 5,428,130, U.S. Pat. No. 5,843,725, U.S. Pat. No. 6,018,026, and Chamow et al., TIBTECH, 14: 52-60 (1996).

The simplest and most straightforward Fc-fusion protein design often combines the binding domain(s) of an antagonist polypeptide of this invention, preferably a native sequence, with the Fc region of an immunoglobulin heavy chain. In another embodiment, the polypeptide can be artificial, such as a polypeptide comprising a sequence of Formula I, Formula II, Formula III, ECFDLLVRAWVPCSVLK (SEQ ID NO: 13), ECFDLLVRHWVPCGLLR (SEQ ID NO: 14), ECFDLLVRRWVPCEMLG (SEQ ID NO: 15), ECFDLLVRSWVPCHMLR (SEQ ID NO: 16), ECFDLLVRHWVACGLLR (SEQ ID NO: 17), or sequences listed in FIG. 32 can be covalently linked to an Fc portion of an immunoglobulin. In addition, one or more of these polypeptides can be linked to one another and linked to an Fc portion of an immunoglobulin.

Ordinarily, when preparing the Fc-fusion proteins of the present invention, nucleic acid encoding the binding domain will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion, or binding characteristics of the Fc-fusion protein.

In a preferred embodiment, the binding domain sequence is fused to the N-terminus of the Fc region of immunoglobulin G1 (IgG1). It is possible to fuse the entire heavy chain constant region to the binding domain sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the binding domain amino acid sequence is fused to (a) the hinge region and CH2 and CH3 or (b) the CH1, hinge, CH2 and CH3 domains, of an IgG heavy chain.

For bispecific Fc-fusion proteins, the Fc-fusion proteins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled Fc-fusion proteins within the scope herein are schematically diagrammed below: (a) ACL-ACL; (b) ACH- (ACH, ACL-ACH, ACL-VHCH, or VLCL-ACH); (c) ACL-ACH- (ACL-ACH, ACL-VHCH, VLCL-ACH, or VLCL-VHCH) (d) ACL-VHCH- (ACH, or ACL-VHCH, or VLCL-ACH); (e) VLCL-ACH- (ACL-VHCH, or VLCL-ACH); and (f) (A-Y) n- (VLCL-VHCH) 2, wherein each A represents identical or different polypeptides comprising an amino acid sequence of sequences derived from BLyS receptor domains, sequences derived from antibodies to BLyS or to receptors to BLyS, or artificial sequences such as Formula I, Formula II, Formula III, ECFDLLVRAWVPCSVLK (SEQ ID NO 5), ECFDLLVRHWVPCGLLR (SEQ ID NO 6), ECFDLLVR-RWVPCEMLG (SEQ ID NO 7), ECFDLLVRSWVPCH-MLR (SEQ ID NO 8), ECFDLLVRHWVACGLLR (SEQ ID NO 9), or sequences listed in FIG. 32 or combinations thereof;

VL is an immunoglobulin light chain variable domain; VH is an immunoglobulin heavy chain variable domain; CL is an immunoglobulin light chain constant domain; CH is an immunoglobulin heavy chain constant domain; n is an integer greater than 1; Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the Fc sequences can be inserted between immunoglobulin heavy chain and light chain sequences, such that an immunoglobulin comprising a chimeric heavy chain is obtained. In this embodiment, the Fc sequences are fused to the 3' end of an immunoglobulin heavy chain in each arm of an immunoglobulin, either between the hinge and the CH2 domain, or between the CH2 and CH3 domains. Similar constructs have been reported by Hoogenboom et al., Mol. Immunol., 28: 1027-1037 (1991).

Although the presence of an immunoglobulin light chain is not required in the Fc-fusion proteins of the present invention, an immunoglobulin light chain might be present either covalently associated to an binding domain-immunoglobulin heavy chain fusion polypeptide, or directly fused to the bdining domain. In the former case, DNA encoding an immunoglobulin light chain is typically coexpressed with the DNA encoding the binding domain-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Fc-fusion proteins are most conveniently constructed by fusing the cDNA sequence encoding the binding domain portion in-frame to an immunoglobulin cDNA sequence. However, fusion to genomic immunoglobulin fragments can also be used (see, e.g. Aruffo et al., Cell, 61: 1303-1313 (1990); and Stamenkovic et al., Cell, 66: 1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the binding domain and the immunoglobulin parts of the Fc-fusion protein are inserted in tandem into a plasmid vector that directs efficient expression in the chosen host cells.

Particular modifications have been made to produce Fc sequences useful for creating fusion molecules such as the BLyS and/or APRIL antagonist Fc fusion molecules for use in the present invention. Specifically, six versions of a modified human IgG1 Fc were generated for creating Fc fusion proteins and are named Fc-488, as well as Fc4, Fc5, Fc6, Fc7, and Fc8. Fc-488 (SEQ ID NO: 39) was designed for convenient cloning of a fusion protein containing the human γ1 Fc region, and it was constructed using the wild-type human immunoglobulin γ1 constant region as a template. Concern about potential deleterious effects due to an unpaired cysteine residue led to the decision to replace the cysteine that normally disulfide bonds with the immunoglobulin light chain constant region with a serine residue. An additional change was introduced at the codon encoding EU index position 218 to introduce a BglII restriction enzyme recognition site for ease of future DNA manipulations. These changes were introduced into the PCR product encoded on the PCR primers. Due to the location of the BglII site and in order to complete the Fc hinge region, codons for EU index positions 216 and 217 were incorporated in the fusion protein partner sequences.

Fc4, Fc5, and Fc6 contain mutations to reduce effector functions mediated by the Fc by reducing FcγRI binding and complement C1q binding. Fc4 contains the same amino acid substitutions that were introduced into Fc-488. Additional amino acid substitutions were introduced to reduce potential Fc mediated effector functions. Specifically, three amino acid substitutions were introduced to reduce FcγRI binding. These are the substitutions at EU index position 234, 235, and 237. Substitutions at these positions have been shown to reduce binding to FcγRI (Duncan et al., Nature 332:563 (1988)). These amino acid substitutions may also reduce FcγRIIa binding, as well as FcγRIII binding (Sondermann et al., Nature 406:267 (2000); Wines et al., J. Immunol. 164:5313 (2000)).

Several groups have described the relevance of EU index positions 330 and 331 (amino acid residues 134 and 135 of SEQ ID NO:6) in complement C1q binding and subsequent complement fixation (Canfield and Morrison, J. Exp. Med. 173:1483 (1991); Tao et al., J. Exp. Med. 178:661 (1993)). Amino acid substitutions at these positions were introduced in Fc4 to reduce complement fixation. The $C_{H3}$ domain of Fc4 is identical to that found in the corresponding wild-type polypeptide, except for the stop codon, which was changed from TGA to TAA to eliminate a potential dam methylation site when the cloned DNA is grown in dam plus strains of *E. coli*.

In Fc5, the arginine residue at EU index position 218 was mutated back to a lysine, because the BglII cloning scheme was not used in fusion proteins containing this particular Fc. The remainder of the Fc5 sequence matches the above description for Fc4.

Fc6 is identical to Fc5 except that the carboxyl terminal lysine codon has been eliminated. The C-terminal lysine of mature immunoglobulins is often removed from mature immunoglobulins post-translationally prior to secretion from B-cells, or removed during serum circulation. Consequently, the C-terminal lysine residue is typically not found on circulating antibodies. As in Fc4 and Fc5 above, the stop codon in the Fc6 sequence was changed to TAA.

Fc7 is identical to the wild-type γ1 Fc except for an amino acid substitution at EU index position 297 located in the $C_{H2}$ domain. EU index position Asn-297 is a site of N-linked carbohydrate attachment. N-linked carbohydrate introduces a potential source of variability in a recombinantly expressed protein due to potential batch-to-batch variations in the carbohydrate structure. In an attempt to eliminate this potential variability, Asn-297 was mutated to a glutamine residue to prevent the attachment of N-linked carbohydrate at that residue position. The carbohydrate at residue 297 is also involved in Fc binding to the FcRIII (Sondermann et al., Nature 406: 267 (2000)). Therefore, removal of the carbohydrate should decrease binding of recombinant Fc7 containing fusion proteins to the FcγRs in general. As above, the stop codon in the Fc7 sequence was mutated to TAA.

Fc8 is identical to the wild-type immunoglobulin γ1 region shown in SEQ ID NO:6, except that the cysteine residue at EU index position 220 was replaced with a serine residue. This mutation eliminated the cysteine residue that normally disulfide bonds with the immunoglobulin light chain constant region. The use of any of these specific Fc domains for formation of the BLyS and/or APRIL antagonist is within the scope of the present invention.

Leucine zipper forms of these molecules are also contemplated by the invention. "Leucine zipper" is a term in the art used to refer to a leucine rich sequence that enhances, promotes, or drives dimerization ortrimerization of its fusion partner (e.g., the sequence or molecule to which the leucine zipper is fused or linked to). Various leucine zipper polypeptides have been described in the art. See, e.g., Landschulz et al., Science, 240: 1759 (1988); U.S. Pat. No. 5,716,805; WO 94/10308; Hoppe et al., FEBS Letters, 344: 1991 (1994); Maniatis et al., Nature, 341: 24 (1989). Those skilled in the art will appreciate that a leucine zipper sequence may be fused at either the 5' or 3' end of the polypeptide of this invention.

The polypeptides of the present invention can also be modified in a way to form chimeric molecules by fusing the polypeptide to another, heterologous polypeptide or amino acid sequence.

According to some embodiments, such heterologous polypeptide or amino acid sequence is one which acts to oligimerize the chimeric molecule. In some embodiments, such a chimeric molecule comprises a fusion of the polypeptide with a tag polypeptide which provides an epitope to which a tag antibody can selectively bind. The epitope tag is generally placed at the amino- or carboxyl-terminus of the polypeptide.

The presence of such epitope-tagged forms of the polypeptide can be detected using an antibody against the tag polypeptide. Also, provision of the epitope tag enables the polypeptide to be readily purified by affinity purification using a tag antibody or another type of affinity matrix that binds to the epitope tag.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8: 2159-2165 (1988)]; the c-myc tag and the 8F9, 3C7, 6E10, G4, B7 and 9E10 antibodies thereto [Evan et al., Molecular and Cellular Biology, 5: 3610-3616 (1985)]; and the Herpes Simplex virus glycoprotein D (gD) tag and its antibody [Paborsky et al., Protein Engineering, 3 (6): 547-553 (1990)]. Other tag polypeptides include the Flag-peptide [Hopp et al., BioTechnology, 6: 1204-1210 (1988)]; the KT3 epitope peptide [Martin et al., Science, 255: 192-194 (1992)]; an"-tubulin epitope peptide [Skinner et al., J. Biol. Chem., 266: 15163-15166 (1991)]; and the T7 gene 10 protein peptide tag [Lutz-Freyermuth et al., Proc. Natl. Acad. Sci: USA, 87: 6393-6397 (1990)].

Construction of Peptide-Polymer Conjugates

In some embodiments the strategy for the conjugation of a polymer, (e.g, PEGylation) of synthetic peptides consists of combining, through forming a conjugate linkage in solution, a peptide and a PEG moiety, each bearing a special functionality that is mutually reactive toward the other. The peptides can be easily prepared with conventional solid phase synthesis. The peptides are "preactivated" with an appropriate functional group at a specific, site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

In some embodiments, a peptide is covalently bonded via one or more of the amino acid residues of the peptide to a terminal reactive group on the polymer, depending mainly on the reaction conditions, the molecular weight of the polymer, etc. The polymer with the reactive group(s) is designated herein as activated polymer. The reactive group selectively reacts with free amino or other reactive groups on the peptide. Potential reactive sites include: N-terminal amino group, epsilon amino groups on lysine residues, as well as other amino, imino, carboxyl, sulfhydryl, hydroxyl, and other hydrophilic groups. It will be understood, however, that the type and amount of the reactive group chosen, as well as the type of polymer employed, to obtain optimum results, will depend on the particular peptide employed to avoid having the reactive group react with too many particularly active groups on the peptide. In some embodiments, a reactive residue, (e.g., lysine (K), a modified, non-natural amino acid, or other small molecule) may be substituted at a position suitable for conjugation.

In some embodiments, the peptide comprises the sequence of Formula I, Formula II, Formula III, ECFDLLVRAWVPCSVLK (SEQ ID NO 5), ECFDLLVRHWVPCGLLR (SEQ ID NO 6), ECFDLLVRRWVPCEMLG (SEQ ID NO 7), ECFDLLVRSWVPCHMLR (SEQ ID NO 8), ECFDLLVRHWVACGLLR (SEQ ID NO 9), or sequences listed in FIG. 32 of WO 05/000351 have a terminal reactive group.

In some embodiments, the peptide comprises at least one and more preferably, more than one of a polypeptide comprising a sequence of Formula I, Formula II, Formula III, ECFDLLVRAWVPCSVLK (SEQ ID NO 5), ECFDLLVRHWVPCGLLR (SEQ ID NO 6), ECFDLLVR-RWVPCEMLG (SEQ ID NO 7), ECFDLLVRSWVPCHMLR (SEQ ID NO 8), ECFDLLVRHWVACGLLR (SEQ ID NO 9), or sequences listed in FIG. 32 of WO 05/000351. The polypeptides that are linked together can have the same sequence or have different sequences and a terminal reactive group. In some embodiments, these polypeptides can be joined to one another, optionally, through the use of a linker.

While conjugation may occur at any reactive amino acid on the polypeptide, in some embodiments, the reactive amino acid is lysine, which is linked to the reactive group of the activated polymer through its free epsilon-amino group, or glutamic oraspartic acid, which is linked to the polymer through an amide bond. In some embodiments, the reactive amino acids of the peptide are not cysteine residues at positions X2 and X1z.

The degree of polymer conjugation with each peptide will vary depending upon the number of reactive sites on the peptide, the molecular weight, hydrophilicity and other characteristics of the polymer, and the particular peptide derivatization sites chosen. In some embodiments, the conjugate has a final molar ratio of 1 to 10 polymer molecules per peptide molecule, but greater numbers of polymer molecules attached to the peptides of the invention are also contemplated. In some embodiments, each conjugate contains one polymer molecule. The desired amount of derivatization is easily achieved by using an experimental matrix in which the time, temperature and other reaction conditions are varied to change the degree of substitution, after which the level of polymer substitution of the conjugates is determined by size exclusion chromatography or other means known in the art.

In some embodiments, the polymer contains only a single group which is reactive. This helps to avoid cross-linking of protein molecules. However, it is within the scope herein to maximize reaction conditions to reduce cross-linking, or to purify the reaction products through gel filtration or ion exchange chromatography to recover substantially homogenous derivatives. In other embodiments, the polymer contains two or more reactive groups for the purpose of linking multiple peptides to the polymer backbone.

Again, gel filtration or ion exchange chromatography can be used to recover the desired derivative in substantially homogeneous form. In some embodiments, the polymer is covalently bonded directly to the peptide without the use of a multifunctional (ordinarily bifunctional) crosslinking agent. In some embodiments, there is a 1:1 molar ratio of PEG chain to peptide.

The covalent modification reaction may take place by any appropriate method generally used for reacting biologically active materials with inert polymers, preferably at about pH 5-9, more preferably 7-9 if the reactive groups on the peptide are lysine groups. Generally, the process involves preparing an activated polymer (the polymer typically having at least one terminal hydroxyl group to be activated), preparing an active substrate from this polymer, and thereafter reacting the peptide with the active substrate to produce the peptide suitable for formulation. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In some embodiments, the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the peptide. Examples of such compounds include N-hydroxysuccinimide, 4-hydroxy-3-nitrobenzene sulfonic acid, and the like, and preferably N-hydroxysuccinimide or 4-hydroxy-3-nitrobenzene sulfonic acid is used. For example, monomethyl substituted PEG may be reacted at elevated temperatures, preferably about 100-110 C for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the GH. This method is described in detail in Abuchowski et al., Cancer Biochem. Biophys., 7: 175-186 (1984). In another example, the monomethyl substituted PEG may be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., Peptides:Synthesis-Structure-Func-tion. Proceedings of the Seventh American Peptide Symposium, Rich et al. (eds.) (Pierce Chemical Co., RockfordIll., 1981), p. 97-100, and in Nitecki et al., High-Technology Route to Virus Vaccines (American Society for Microbiology: 1986) entitled "Novel Agent for Coupling Synthetic Peptides to Carriers and Its Applications."

In some embodiments, covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylchloroformate or P-nitrophenylchloroformate activated PEG. Carboxyl groups are derivatized by coupling PEG-amine using carbodiimide. Sulfhydryl groups are derivatized by coupling to maleimido-substituted PEG (e.g. alkoxy-PEG amine plus sulfosuccinimidyl 4-(N-maleimidomethyl) cyclohexane-1-carboxylate) as described in WO97/10847 published Mar. 27, 1997, or PEG-maleimide commercially available from Nektar Technologies, San Carlos, Calif. (formerly Shearwater Polymers, Inc.). Alternatively, free amino groups on the peptide (e.g. epsilon amino groups on lysine residues) may be coupled to N-hydroxysucciminidyl substituted PEG (PEG-NHS available from Nektar Technologies;) or can be thiolated with 2-imino-thiolane (Traut's reagent) and then coupled to maleimide-containing derivatives of PEG as described in Pedley et al., Br. J. Cancer, 70: 1126-1130 (1994).

Many inert polymers, including but not limited to PEG, are suitable for use in pharmaceuticals. See, e.g., Davis et al., Biomedical Polymers: Polymeric Materials and Pharmaceuticals for Biomedical Use, pp. 441-451 (1980). In some embodiments of the invention, a non-proteinaceous polymer is used. The nonproteinaceous polymer is typically a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; heparin orheparon.

The polymer prior to conjugation need not be, but preferably is, water soluble, but the final conjugate is preferably water-soluble. Preferably, the conjugate exhibits a water solubility of at least about 0.01 mg/ml, and more preferably at least about 0.1 mg/ml, and still more preferably at least about 1 mg/ml.

In addition, the polymer should not be highly immunogenic in the conjugate form, nor should it possess viscosity that is incompatible with intravenous infusion, injection, or inhalation if the conjugate is intended to be administered by such routes.

The molecular weight of the polymer can range up to about 100,000 D, and preferably is at least about 500 D, or at least about 1,000 D, or at least about 5,000 D. In some embodiments, the PEG or other polymer has a molecular weight in the range of 5000 to 20,000 D. The molecular weight chosen can depend upon the effective size of the conjugate to be achieved, the nature (e.g. structure, such as linear or branched) of the polymer, and the degree of derivatization, i.e. the number of polymer molecules per peptide, and the polymer attachment site or sites on the peptide. In some embodiments, branched PEG's may used to induce a large increase in effective size of the peptides. PEG or other polymer conjugates may be utilized to increase half-life, increase solubility, stabilize against proteolytic attack, and reduce immunogenicity.

Functionalized PEG polymers to modify the peptides of the invention are available from Nektar Technologies of San Carlos, Calif. (formerly Shearwater Polymers, Inc.). Such commercially available PEG derivatives include, but are not limited to, amino-PEG, PEG amino acid esters. PEG-N-hydroxysuccinamide chemistry HS), PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-xycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, hetero functional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates may be characterized by SDS-PAGE, gel filtration, NMR, tryptic mapping, liquid chromatography-mass spectrophotometry, and in vitro biological assays. For example, the extent of PEG conjugation may be shown by SDS-PAGE and gel filtration, and then analyzed by NMR, which has a specific resonance peak for the methylene hydrogens of PEG. The number of PEG groups on each molecule can be calculated from the NMR spectrum or mass spectrometry. Polyacrylamide gelelectrophoresis in 10% SDS is appropriately run in 10 mMTris-HCl pH 8.0, 100 mMNaCl as elution buffer. To demonstrate which residue is PEGylated, tryptic mapping can be performed. Thus, PEGylated peptides are digested with trypsin at the protein/enzyme ratio of 100 to 1 in mg basis at 37 C for 4 hours in 100 mM sodium acetate, 10 mMTris-HCl, 1 mM calcium chloride, pH 8.3, and acidified to pH<4 to stop digestion before separating on HPLC NucleosilC-18 (4.6 mm. times. 150 mm, 5. mu., 100 A). The chromatogram is compared to that of non-PEGylated starting material. Each peak can then be analyzed by mass spectrometry to verify the size of the fragment in the peak. The fragment (s) that carried PEG groups are usually not retained on the HPLC column after injection and disappear from the chromatograph. Such disappearance from the chromatograph is an indication of PEGylation on that particular fragment that should contain at least one lysine residue. PEGylated peptides may then be assayed for ability to bind to the BLyS by conventional methods.

In some embodiments, conjugates are purified by ion-exchange chromatography, (e.g, ion-exchange HPLC. The chemistry of many of the electrophilically activated PEG's results in a reduction of amino group charge of the PEGylated product. Thus, high resolution ion exchange chromatography can be used to separate the free and conjugated proteins, and to resolvespecies-', with different levels of PEGylation.

In fact, the resolution of different species (e.g. containing one or two PEG residues) is also possible due to the difference in the ionic properties of the unreacted amino acids. In one embodiment, species with difference levels of PEGylation are resolved according to the methods described in WO 96/34015 (International Application No. PCT/US96/05550 published Oct. 31, 1996). Heterologous species of the conjugates are purified from one another in the same fashion.

In some embodiments, PEG-N-hydroxysuccinamide (NHS) reacts with a primary amine (e.g. lysines and the N-terminus). In some embodiments, PEG-NHS reacts with a C-terminal lysine (K) of the polypeptide. In some embodiments, the lysine residue is added to the C-terminus of the 17-mer polypeptide, while in other embodiments, Xi is substituted with lysine. In some embodiments, the polymer reacts with the N-terminus. In a preferred embodiment, the conjugate is generated by utilizing the derivatization and purification methods described in the Examples below.

In one aspect, the invention provides any of the above-described conjugates formed by its component parts, i.e. one or more peptide(s) covalently attached to one or more polymer molecule (s), without any extraneous matter in the covalent molecular structure of the conjugate.

The methods and articles of manufacture of the present invention use, or incorporate, an antibody which binds to BLyS or one or more of its three receptors. Accordingly, methods for generating such antibodies will be described here.

The BLyS or BLyS receptor to be used for production of, or screening for, antibodies may be, e.g., a soluble form of the antigen or a portion thereof, containing the desired epitope. As described above, the BLyS sequence and the sequence of the BLyS receptors are known as are the boundaries of the various domains of these polypeptides. Peptide fragments of the extracellular domain (ECD) can be used as immunogens. Based on these known sequences and domain delineations, one of skill in the art can express the BLyS or BLyS receptors polypeptides and fragments thereof for use to produce antibodies.

To generate antibodies to BLyS or its receptors, full length polypeptides or peptide fragments of 6 or greater residues in length can be used as immunogens to raise antibodies in rodents including mice, hamsters, and rats, in rabbit, goat, or other suitable animal. Soluble BLyS or BLyS receptor polypeptide or immunogenic fragments thereof can be expressed is suitable host cells such as bacteria or eukaryotic cells. In one embodiment, human and murine detergent-solubilized full-length BLyS are produced in *E. coli* and used to immunize and screen for hybridomas producing BLyS antibodies.

Alternatively, or additionally, B cells or cell lines expressing BLyS or BLyS receptors at their cell surface can be used to generate, and/or screen for, antibodies. Other forms of BLyS useful for generating antibodies will be apparent to those skilled in the art, such as phage display methodology can also be used to produce BLyS binding antibody. The antibodies that bind BLyS or the BLyS receptors may be chimeric, humanized, or human. Such antibodies and methods of generating them are described in more detail below.

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOC12, or R1N=C=NR, where R and R' are different alkyl groups.

Animals are immunized against the antigen, immunogenic conjugates, or derivatives by combining, e.g., 100 wu or 5 g of the protein or conjugate (for rabbits or mice, respectively) with 3 volumes of Freund's complete adjuvant and injecting the solution intradermally at multiple sites. One month later the animals are boosted with $\frac{1}{5}$ to $\frac{1}{10}$ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256: 495 (1975), or may be made by recombinant DNA methods (U.S. Pat. No. 4,816,567). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are-fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium.

Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, Monoclonal Antibodies Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5: 256-262 (1993) and Pluckthun, Immunol Revs., 130: 151-188 (1992).

In a further embodiment, antibodies or antibody fragments can be isolated from antibody phage libraries generated using the techniques described in McCafferty et al., Nature, 348: 552-554 (1990).

Clackson et al., Nature, 352: 624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., BiolZ'echraology, 10: 779-783 (1992)), as well as combinatorial infection and in vivo recombination as a strategy for constructing very large phage libraries (Waterhouse et aL, Nuc. Acids. Res., 21: 2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81: 6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321: 522-525 (1986); Riechmann et al., Nature, 332: 323-327 (1988); Verhoeyen et al., Science, 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., J. Immunol., 151: 2296 (1993); Chothia et al., J. Mol. Biol., 196: 901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89: 4285 (1992); Presta et al., J. Immunol., 15-1:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences.

Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen (s), is achieved. In general, the hypervariable region residues are directly and most substantially involved in influencing antigen binding.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production.

Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255-258 (1993); Brug-germann et al., Year in Immuno., 7: 33 (1993); and U.S. Pat. Nos. 5,591,669, 5, 589,369 and 5,545,807.

Alternatively, phage display technology (McCafferty et al., Nature 348: 552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell.

Phage display can be performed in a variety of formats; for their review see, e.g., Johnson, Kevin S, and Chiswell, David J., Current Opinion in Structural Biology 3: 564-571 (1993). Several sources of V-gene segments can be used for phage display. Clackson et al., Nature, 352: 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222: 581-597 (1991), or Griffith et al., EMBO J. 12: 725-734 (1993). See, also, U.S. Pat. Nos. 5,565,332 and 5,573,905. Human antibodies may also be generated by in vitro activated B cells (see U.S. Pat. Nos. 5,567,610 and 5,229,275).

Various techniques have been developed for the production of antibody fragments. Traditionally, these fragments were derived via proteolytic digestion of intact antibodies (see, e.g., Morimoto et al., Journal of Biochemical and Biophysical Methods 24: 107-117 (1992) and Brennan et al., Science, 229: 81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F (ab') 2 fragments (Carter et al., Bio/Technology 10: 163-167 (1992)). According to another approach, F (ab')2 fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody,", e.g., as described in U.S. Pat. No. 5,641,870 for example. Such linear antibody fragments may be monospecific or bispecific.

Bispecific antibodies are antibodies that have binding specificities for at least two different epitopes. Exemplary bispecific antibodies may bind to two different epitopes of the B cell surface marker. Other such antibodies may bind a first B cell marker and further bind a second B cell surface marker. Alternatively, an anti-B cell marker binding arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the B cell. Bispecific antibodies may also be used to localize cytotoxic agents to the B cell. These antibodies possess a B cell marker-binding arm and an arm which binds the cytotoxic agent (e.g. saporin, anti-interferon-, vinca alkaloid, ricin A chain, methotrexate or radioactive isotope hapten).

Bispecific antibodies can be prepared as full length antibodies or antibody fragments (e.g. F (ab') 2 bispecific antibodies). Methods for making bispecific antibodies are known in the art. Traditional production of full length bispecific antibodies is based on the coexpression of two immunoglobulin heavy chain-light chain pairs, where the two chains have different specificities (Millstein et al., Nature, 305: 537-539 (1983)).

Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO93/08829, and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region(CH1) containing the site necessary for light chain binding, present in at least one of the fusions. DNAs-encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121: 210 (1986). According to another approach described in U.S. Pat. No. 5,731,168, the interface between a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al, Science, 229: 81 (1985) describe a procedure wherein intact antibodies are proteolytically cleaved to generate F (ab') 2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F (ab') 2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148 (5): 1547-1553 (1992). The leucine zipper peptides from the Fos and Jun proteins were linked to the Fab'portions of two different antibodies by gene fusion. The antibody homodimers were reduced at the hinge region to form monomers and then re-oxidized to form the antibody heterodimers. This method can also be utilized for the production of antibody homodimers.

The "diabody" technology described by Hollinger et al, Proc. Natl. Acad. Sci. USA, 90: 6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152: 5368 (1994).

Antibodies with more than two valencies are contemplated. For example, trispecific antibodies can be prepared. Tutt et al., J. Immunol. 147: 60 (1991).

Amino acid sequence modification(s) of protein or peptide antagonists and antibodies described herein are contemplated. For example, it may be desirable to improve the binding affinity and/or other biological properties of the BLYS binding antibody or antagonist. Amino acid sequence variants of the antagonist are prepared by introducing appropriate nucleotide changes into the antagonist nucleic acid, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics. The amino acid changes also may alter post-translational processes of the antagonist, such as changing the number or position of glycosylation sites.

A useful method for identification of certain residues or regions of the antagonist that are preferred locations for mutagenesis is called "alanine scanning mutagenesis" as described by Cunningham and Wells Science, 244: 1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, -the sites of substitution. Thus, while the site for introducing an amino acid sequence variation is predetermined, the nature of the mutation per se need not be predetermined. For example, to analyze the performance of a mutation at a given site, tala scanning or random mutagenesis is conducted at the target codon or region and the expressed antagonist variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antagonist with an N-terminal methionyl residue or the antagonist fused to a cytotoxic polypeptide. Other insertional variants of the antagonist molecule include the fusion to the N- or C-terminus of the antagonist of an enzyme, or a polypeptide which increases the serum half-life of the antagonist.

Another type of variant is an amino acid substitution variant. These variants have at least one amino acid residue in the antagonist molecule replaced by different residue. The sites of greatest interest for substitutional mutagenesis of antibody antagonists include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

Substantial modifications in the biological properties of the antagonist are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe. Non-conservative substitutions will entail exchanging a member of one of these classes for another class.

Any cysteine residue not involved in maintaining the proper conformation of the antagonist also may be substituted, generally with serine, to improve the oxidative stability of the molecule and prevent aberrant crosslinking. Conversely, cysteine bond(s) may be added to the antagonist to improve its stability (particularly where the antagonist is an antibody fragment such as an Fv fragment).

A particularly preferred type of substitutional variant involves substituting one or more hypervariable region residues of a parent antibody. Generally, the resulting variant(s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution-according to the techniques elaborated herein. Once such variants are generated, the panel of variants is subjected to screening as described herein and antibodies with superior properties in one or more relevant assays may be selected for further development.

Another type of amino acid variant of the antagonist alters the original glycosylation pattern of the antagonist. By altering is meant deleting one or more carbohydrate moieties found in the antagonist, and/or adding one or more glycosylation sites that are not present in the antagonist.

Glycosylation of polypeptides is typically either N-linked or 0-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. 0-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antagonist is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antagonist (for 0-linked glycosylation sites).

Nucleic acid molecules encoding amino acid sequence variants of the antagonist are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antagonist.

It may be desirable to modify the antagonist of the invention with respect to effector function, e.g. so as to enhance antigen-dependent cell-mediated cyotoxicity (ADCC) and/or complement dependent cytotoxicity (CDC) of the antagonist. This may be achieved by introducing one or more amino acid substitutions in an Fc region of an antibody antagonist. Alternatively or additionally, cysteine residue (s) may be introduced in the Fc region, thereby allowing interchain disulfide bond formation in this region.

The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148: 2918-2922 (1992). Homodimeric antibodies with enhanced anti-tumor activity may also be prepared using heterobifunctional cross-linkers as described in Wolff et al. Cancer Research 53: 2560-2565 (1993). Alternatively, an antibody can be engineered which has dual Fc regions and may thereby have enhanced complement lysis and ADCC capabilities. See Stevenson et al. Anti-Cancer Drug Design 3: 219-230 (1989).

To increase the serum half life of the antagonist, one may incorporate a salvage receptor binding epitope into the antagonist (especially an antibody fragment) as described in U.S. Pat. No. 5,739,277, for example. As used herein, the term "salvage receptor binding epitope" refers to an epitope of the Fc region of an IgG molecule (e.g.,—IgG1, IgG2, IgG3, or IgG4) that-is responsible for increasing the in vivo serum half-life of the IgG molecule.

Assays

Peripheral B-cell concentrations are determined by a FACS method that count CD3−/CD40+ cells.

The percent of CD3-CD40+ B cells of total lymphocytes in samples can be obtained by the following gating strategy. The lymphocyte population is marked on the forward scatter/side scatter scattergram to define Region 1(Ri). Using events in RI, fluorescence intensity dot plots are displayed for CD40 and CD3 markers. Fluorescently labeled isotype controls are used to determine respective cutoff points for CD40 and CD3 positivity.

FACS Analysis

Half million cells are washed and resuspended in 100l of FACS buffer, which is phosphate buffered saline with 1% BSA, containing 5, ul of staining or control antibody. All the staining antibodies, including isotype controls, are obtained from PharMingen, San Diego, Calif. Human BLYS expression is assessed by staining with Rituxan@ along with FITC-conjugated anti-human IgG1 secondary antibody.

FACS analysis is conducted using FACScan and Cell Quest (Becton Dickinson Immunocytometry Systems, San Jose, Calif.). All the lymphocytes are defined in the forward and side light scatterings, while all the B lymphocytes are defined with the expression of B220 on the cell surface.

B cell depletion and recovery are assessed by analyzing peripheral B cell counts and analysis of hBLYS+ B cells by FACS in the spleen, lymph node and bone marrow on a daily basis for the first week after injection and thereafter on a weekly basis. Serum levels of the injected 2H7 variant antibody are monitored.

Pharmaceutical Formulations

Therapeutic formulations of the BLyS and/or APRIL antagonists such as BLyS-binding antibodies used in accordance with the present invention are prepared for storage by mixing an antibody having the desired degree of purity with optional pharmaceutically acceptable carriers, excipients or stabilizers (Remitgtorz's Phamamaceutical Science 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN, PLURONICS™ or polyethylene glycol (PEG).

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g. one which binds LFA-1). The effective amount of such other agents depends on the amount of antibody present in the formulation, the type of disease or disorder or treatment, and other factors discussed above. These are generally used in the same dosages and with administration routes as described herein or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Disease Treatment

Diseases

The immunosuppressive drugs and the BLyS and/or APRIL antagonists of the invention are useful to treat B-cell regulated autoimmune disorders. B-cell regulated autoimmune diseases include arthritis (rheumatoid arthritis, juvenile rheumatoid arthritis, osteoarthritis, psoriatic arthritis), psoriasis, dermatitis including atopic dermatitis; chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), respiratory distress syndrome, adult respiratory distress syndrome (ARDS), meningitis, allergic rhinitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), lupus (including nephritis, non-renal, discoid, alopecia), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pretreatment for high panel reactive antibody titers, IgA deposit in tissues, etc), graft versus host disease (GVHD), pemphigoid bullous, pemphigus (all including vulgaris, foliaceus), autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura(TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), sub-acute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, Lymphoid interstitial pneumonitis (HIV), bronchiolitis obliterans (non-transplant) vs NSIP, Guillain-Barre' Syndrome, Large Vessel Vasculitis (including Polymyalgia Rheumatica and Giant Cell (Takayasu's) Arteritis), Medium Vessel Vasculitis (including Kawasaki's Disease and Polyarteritis Nodosa), ankylosing spondylitis, Berger's Disease (IgA nephropathy), Rapidly Progressive Glomerulonephritis, Primary biliary cirrhosis, Celiac sprue (gluten enteropathy), Cryoglobulinemia, ALS, coronary artery disease.

The desired level of B-cell depletion will depend on the disease. Preferably, the B cell depletion is sufficient to prevent progression of disease for at least 2 months, more preferably 3 months, even more preferably 4 months, more preferably 5 months, even more preferably 6 or more months. In even more preferred embodiments, the B cell depletion is sufficient to increase the time in remission by at least 6 months, more preferably 9 months, more preferably one year, more preferably 2 years, more preferably 3 years, even more preferably 5 or more years. In a most preferred embodiment, the B cell depletion is sufficient to cure the disease. In preferred embodiments, the B cell depletion in the autoimmune patient is at least transiently about 75% and more preferably, 80%, 85%, 90%, 95%, 99% and even 100% of the baseline level before treatment.

For treatment of an autoimmune disease, it may be desirable to modulate the extent of B cell depletion depending on the disease and/or the severity of the condition in the individual patient, by adjusting the dosage of the immunosuppressive drug or the BLyS and/or APRIL antagonist. Thus, B-cell depletion can but does not have to be complete. Or, total B cell-depletion may be desired in initial treatment but in subsequent treatments, the dosage may be adjusted to achieve only partial depletion. In one embodiment, the B cell depletion is at least 20%, i.e., 80% or less of B-cells remain as compared to the baseline level before treatment. In other embodiments, B-cell depletion is 25%, 30%, 40%, 50%, 60%, 70% or greater.

Preferably, the B cell depletion is sufficient to halt progression of the disease, more preferably to alleviate the signs and symptoms of the particular disease under treatment, even more preferably to cure the disease.

For therapeutic applications, the immunosuppressive drug and BLyS and/or APRIL antagonist compositions of the invention can be used in combination therapy with additional drugs such as anti-inflammatory drugs, including DMARDS and other biologics. The preceding treatment methods can be administered in conjunction with other forms of conventional therapy for autoimmune disease, either consecutively with, pre- or post-conventional therapy.

A patient is alleviated or successfully treated of a B cell regulated autoimmune diseases by the present methods of the invention if there is a measurable-improvement in the symptoms or other applicable criteria after administration of the compositions of the invention compared to before treatment. The effect of treatment may be apparent within 3-10 weeks after administration of the compositions of the invention. The applicable criteria for each disease will be well known to the physician of skill in the appropriate art. For example, the physician can monitor the treated patient for clinical, or serologic evidence of disease such as serologic markers of disease, complete blood count including B cell count, and serum immunoglobulin levels. Serum levels of IgG and IgM are reduced in BLyS and/or APRIL antagonist, such as atacicept, treated mice. Human patients responding to actacicept treatment likewise show a reduction in serum IgG and IgM levels.

The parameters for assessing efficacy or success of treatment of an autoimmune or autoimmune related disease will be known to the physician of skill in the appropriate disease. Generally, the physician of skill will look for reduction in the signs and symptoms of the specific disease. The following are by way of examples.

Rheumatoid arthritis (RA) is an autoimmune disorder of unknown etiology. Most RA patients suffer a chronic course of disease that, even with therapy, may result in progressive joint destruction, deformity, disability and even premature death. The goals of RA therapy are to prevent or control joint damage, prevent-loss of function and decrease pain. Initial therapy of RA usually involves administration of one or more of the following drugs: nonsteroidal anti-inflammatory drugs (NSAIDs), glucocorticoid (via joint injection), and low-dose prednisone. See "Guidelines for the management of rheumatoid arthritis" Arthritis & Rhemmatism 46 (2): 328-346 (February, 2002). The majority of patients with newly diagnosed RA are started with disease-modifying antirheumatic drug (DMARD) therapy within 3 months of diagnosis.

DMARDs commonly used in RA are hydroxycloroquine, sulfasalazine, methotrexate, leflunomide, etanercept, infliximab (plus oral and subcutaneous methrotrexate), azathioprine, D-penicillamine, Gold (oral), Gold (intramuscular), minocycline, cyclosporine, Staphylococcal protein A immunoadsorption.

Because the body produces tumor necrosis factor alpha (TNFa) during RA, TNFa inhibitors have used for therapy of that disease. Etanercept (ENBREL) is an injectable drug approved in the US for therapy of active RA. Etanercept binds to TNFa and serves to remove most TNFa from joints and blood, thereby preventing TNFa from promoting inflammation and other symptoms of rheumatoid arthritis.

Etanercept is an "Fc-fusion protein" fusion protein consisting of the extracellular ligand binding portion of the human 75 kD (p 75) tumor necrosis factor receptor (TNFR) linked to the Fc portion of a human Ig G1.

Infliximab, sold under the trade name REMICADE, is an immune-suppressing drug prescribed to treat RA and Crohn's disease. Infliximab is a chimeric monoclonal antibody that binds to TNF and reduces inflammation in the body by targeting and binding to TNFα which produces inflammation.

Adalimumab(HUMIRA™, Abbott Laboratories), previously known as D2E7, is a human monoclonal antibody that binds to TNFa and is approved for reducing the signs and symptoms and inhibiting the progression of structural damage in adults with moderately to severely active RA who have had insufficient response to one or more traditional disease modifying DMARDs.

Treatment of rheumatoid arthritis by administering immunosuppressive drugs and a BLyS and/or APRIL antagonist can be preformed in conjunction with therapy with one or more of the aforementioned drugs for RA. For rheumatoid arthritis, for example, measurements for progress in treatment may include the number of swollen and tender joints and the length of morning stiffness. Patients may be examined for how much the joint in the hands and feet have eroded by using X-rays and a scoring system known as the Sharp score. Another scoring system is based on the American College of Rheumatology criteria for assessing response to therapies.

One method of evaluating treatment efficacy in RA is based on American College of Rheumatology (ACR) criteria, which measures the percentage of improvement in tender and swollen joints, among other things. The RA patient can be scored at for example, ACR 20 (20 percent improvement) compared with no antibody treatment (e.g, baseline before treatment) or treatment with placebo. Other ways of evaluating the efficacy of antibody treatment include X-ray scoring such as the Sharp X-ray score used to score structural damage such as bone erosion and joint space narrowing. Patients can also be evaluated for the prevention of or improvement in disability based on Health Assessment Questionnaire [HAQ] score, AIMS score, SF-36 at time periods during or after treatment. The ACR 20 criteria may include 20% improvement in both tender (painful) joint count and swollen joint count plus a 20% improvement in at least 3 of 5 additional measures:
1. patient's pain assessment by visual analog scale (VAS),
2. patient's global assessment of disease activity (VAS),
3. physician's global assessment of disease activity (VAS),
4. patient's self-assessed disability measured by the Health Assessment Questionnaire, and
5. acute phase reactants, CRP or ESR.

The ACR 50 and 70 are defined analogously. Preferably, the patient is administered an amount of a BLYS binding antibody of the invention effective to achieve at least a score of ACR 20, preferably at least ACR 30, more preferably at least ACR 50, even more preferably at least ACR 70, most preferably at least ACR 75 and higher.

Psoriatic arthritis has unique and distinct radiographic features. For psoriatic arthritis, joint erosion and joint space narrowing can be evaluated by the Sharp score as well. The humanized BLYS binding antibodies disclosed herein can be used to prevent the joint damage as well as reduce disease signs and symptoms of the disorder.

Yet another aspect of the invention is a method of treating Lupus or SLE by administering to the patient suffering from SLE, a therapeutically effective amount of a BLyS and/or APRIL antagonist in combination with an immunosuppressive drug of the invention. SLEDAI scores provide a numerical quantitation of disease activity. The SLEDAI is a weighted index of 24 clinical and laboratory parameters known to correlate with disease activity, with a numerical range of 0-103. See Bryan Gescuk & John Davis, "Novel therapeutic agent for systemic lupus erythematosus" in Current Opinion in Rheumatology 2002, 14: 515-521. Antibodies to double-stranded DNA are believed to cause renal flares and other manifestations of lupus. Patients undergoing antibody treatment can be monitored for time to renal flare, which is defined as a significant, reproducible increase in serum creatinine, urine protein or blood in the urine. Alternatively or in addition, patients can be monitored for levels of antinuclear antibodies and antibodies to double-stranded DNA. Treatments for SLE include high-dose corticosteroids and/or cyclophosphamide (HDCC). For systemic lupus erythematosus, patients can be monitored for levels of antinuclear antibodies and antibodies to double-stranded DNA.

A particular aspect of the present invention is the treatment of lupus nephritis with a combination of immunosuppressive drugs and a BLyS and/or APRIL antagonist, such as atacicept.

Spondyloarthropathies are a group of disorders of the joints, including ankylosing spondylitis, psoriatic arthritis and Crohn's disease. Treatment success can be determined by validated patient and physician global assessment measuring tools.

A further autoimmune disease that can be treated using the methods of the present invention is psoriasis. Various medications are presently used to treat psoriasis; treatment differs directly in relation to disease severity. Patients with a more mild form of psoriasis typically utilize topical treatments, such as topical steroids, anthralin, calcipotriene, clobetasol, and tazarotene, to manage the disease while patients with moderate and severe psoriasis are more likely to employ systemic (methotrexate, retinoids, cyclosporine, PLTVA and UVB) therapies. Tars are also used. These therapies have a combination of safety concerns, time consuming regimens, or inconvenient processes of treatment. Furthermore, some require expensive equipment and dedicated space in the office setting. Systemic medications can produce serious side effects, including hypertension, hyperlipidemia, bone marrow suppression, liver disease, kidney disease and gastrointestinal upset. Also, the use of phototherapy can increase the incidence of skin cancers. In addition to the inconvenience and discomfort associated with the use of topical therapies, phototherapy and systemic treatments require cycling patients on and off therapy and monitoring lifetime exposure due to their side effects.

Treatment efficacy for psoriasis is assessed by monitoring changes in clinical signs and symptoms of the disease including Physician's Global Assessment (PGA) changes and Psoriasis Area and Severity Index (PASI) scores, Psoriasis Symptom Assessment (PSA), compared with the baseline condition. The patient can be measured periodically throughout treatment on the Visual analog scale used to indicate the degree of itching experienced at specific time points.

Various other inflammatory diseases that have autoimmune causation are also within the scope of the present treatment method. Among the diseases specifically contemplated are autoimmune hepatitis and autoimmune thyroiditis. Autoimmune hepatitis involves inflammation of the liver due to self-attack by the patient's own immune system. Similarly, self-attack and resulting inflammation of the thyroid is the biological cause of autoimmune thyroiditis. Diseases such as this are expected to be elevated using by the combination of BLyS and/or APRIL antagonist with an immunesuppressive drug such as MMF.

Dosing

Depending on the indication to be treated and factors relevant to the dosing that a physician of skill in the field would be familiar with, the BLyS and/or APRIL antagonists and immunosuppressive drugs of the invention will be administered at a dosage that is efficacious for the treatment of that indication while minimizing toxicity and side effects. Generally, the BLyS and/or APRIL antagonist of the present invention will be administered to a human patient at a dosage range of about 0.25 mg/kg to about 25 mg/kg body weight, preferably at about 1 mg/kg to about 10 mg/kg. Alternatively expressed, a preferred range of dosages for the BLyS and/or APRIL antagonist is about 75 to about 190 mg per dose. In a preferred embodiment, the dosage is about 150 mg per dose for the BLyS and/or APRIL antagonist.

The treatment methods of the invention comprises a combination of concurrently and sequentially administering the immunosuppressive drugs and the BLyS and/or APRIL antagonist (both referred to herein as the treatment moieties). In sequential administration, the treatment moeities can be administered in either order, i.e., immunosuppressive drugs first followed by BLyS and/or APRIL antagonist. The patient can be treated with one drug and monitored for efficacy before treatment with the one drug. For example, if the immunosuppressive drug produces a partial response, treatment can be followed with the BLyS and/or APRIL antagonist to achieve a full response, and vice versa. Alternatively, the patient can be initially administered both drugs and subsequent dosing can be with only one or the other drug.

To condition the patient to tolerate the drugs and/or to reduce the occurrence of adverse effects such as infusion-related symptoms which arise from the initial and subsequent administrations of the therapeutic compound, the mammal in need thereof can be administered a first or initial conditioning dose of one or both drugs and then administered at least a second therapeutically effective dose of one or both drugs wherein the second and any subsequent doses are higher than the first dose. The first dose serves to condition the mammal to tolerate the higher second therapeutic dose. In this way, the mammal is able to tolerate higher doses of the therapeutic compound than could be administered initially. A "conditioning dose" is a dose which attenuates or reduces the frequency or the severity of first dose adverse side effects associated with administration of a therapeutic compound. The conditioning dose may be a therapeutic dose, a sub-therapeutic dose, a symptomatic dose or a sub-symptomatic dose. A therapeutic dose is a dose which exhibits a therapeutic effect on the patient and a sub-therapeutic dose is a dose which does not exhibit a therapeutic effect on the patient treated. A symptomatic dose is a dose which induces at least one adverse effect on administration and a sub-symptomatic dose is a dose which does not induce an adverse effect. Some adverse effects are fever, headache, nausea, vomiting, breathing difficulties, myalgia, and chills.

Beyond a conditioning dose regimen, there are a number of other regimens that can be followed to achieve the disease alleviation of the presention invention. One such approach is a short treatment course of one immunosuppressive drug, followed by tapering, followed by treatment with the combination of another immunosuppressive drug and the BLyS and/or APRIL antagonist. For example, corticosteroids can be given 1000-1500 mg orally, twice daily for four weeks, followed by tapering of 5 mg/week down to 10 mg/day over the course of 10 weeks. Once it is time to begin the BLyS and/or APRIL antagonist, a loading dose regimen may be appropriate. In particular, atacicept can be administered twice per week for four weeks followed by weekly administration for an extended period of time, such as 48 weeks. In contrast, the immunosuppressive drug will tend to be administered in an escalating dose regimen. For example, MMF can be administered at a dose of 500 mg twice daily and increased to 750 mg twice daily after two weeks. Weekly advances in dosage can be made up to a maximum dose of 1000 mg 3 times daily if the patient's white blood cell count remains at acceptable levels (i.e., above $3.0 \times 10^9$/L or 3000/mm$^2$). In particular, it would be expected that the maximal range of administration of MMF would be from 2000 to 3000 mg per patient per day.

Route of Administration

The BLyS and/or APRIL antagonists and the immunosuppressive drugs are administered to a human patient in accord with known methods, such as by intravenous administration, e.g., as a bolus or by continuous infusion over a period of time, by subcutaneous, intramuscular, intraperitoneal, intracerobrospinal, intra-articular, intrasynovial, intrathecal, or inhalation routes. Immunosuppressive drugs with appropriate formulation may also be administered orally or topically. The BLyS and/or APRIL antagonist and some immunosuppressive drugs will generally be administered by intravenous or subcutaneous administration. The different treatment moeities can be administered by the same or different routes.

Articles of Manufacture and Kits

Another embodiment of the invention is an article of manufacture comprising a BLyS and/or APRIL antagonist and immunosuppressive drugs to treat a B-cell regulated autoimmune disorder as disclosed above. In a specific embodiment, the article of manufacture contains actacicept and MMF for the treatment of lupus nephritis.

The article of manufacture comprises at least one container and a label or package insert on or associated with the container. Suitable containers include, for example, bottles, vials, syringes, etc. The containers may be formed from a variety of materials such as glass or plastic. The container holds a composition of the invention which is effective for treating the condition and may have a sterile access port (for example the container may be an intravenous solution bag or a vial having a stopper pierceable by a hypodermic injection needle). The label or package insert indicates that the composition is used for treating the particular condition, e.g., lupus nephritis or rheumatoid arthritis. The label or package insert will further comprise instructions for administering the composition to the patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for B-cell killing assays. As with the article of manufacture, the kit comprises a container and a label or package insert on or associated with the container. The container holds a composition comprising at least one immunosuppressive drug and one BLyS and/or APRIL antagonist of the invention. Additional containers may be included that contain, e.g., diluents and buffers, control antibodies. The label or package insert may provide a description of the composition as well as instructions for the intended in vitro or diagnostic use.

EXPERIMENTAL EXAMPLES

Example 1

Production of BLyS and/or APRIL Antagonist

Four amino terminal truncated versions of TACI-Fc were generated. All four had a modified human tissue plasminogen activator signal sequence as disclosed in WO 02/094852 (SEQ ID NO: 41) fused to amino acid residue number 30 of SEQ ID NO:2. However, the four proteins differed in the location of point in which the Fc5 was fused to the TACI amino acid sequence of SEQ ID NO:2. Table 1 outlines the structures of the four fusion proteins.

TABLE 1

TACI Fc Fusion Proteins

| Designation of TACI-Fc | TACI amino acid residues |
|---|---|
| TACI(d1-29)-Fc5 | 30 to 154 of SEQ ID NO: 2 |
| TACI(d1-29, d107-154)-Fc5 | 30 to 106 of SEQ ID NO: 2 |

TABLE 1-continued

TACI Fc Fusion Proteins

| Designation of TACI-Fc | TACI amino acid residues |
|---|---|
| TACI(d1-29, d111-154)-Fc5 | 30 to 110 of SEQ ID NO: 2 |
| TACI(d1-29, d120-154)-Fc5 | 30 to 119 of SEQ ID NO: 2 |

Protein encoding expression cassettes were generated by overlap PCR using standard techniques (see, for example, Horton et al., Gene 77:61 (1989)). A nucleic acid molecule encoding TACI and a nucleic acid molecule encoding Fc5 were used as PCR templates. Oligonucleotide primers are identified in Tables 2 and 3.

TABLE 2

Oligonucleotide Primers Used to Produce TACI Fusion Proteins

| | Oligonucleotide Designations | | | |
|---|---|---|---|---|
| Designation of TACI-Fc | 5' TACI | 3' TACI | 5' Fc5 | 3' Fc5 |
| TACI(d1-29)-Fc5 | ZC24,903 | ZC24,955 | ZC24,952 | ZC24,946 |
| TACI(d1-29, d107-154)-Fc5 | ZC24,903 | ZC24,951 | ZC24,949 | ZC24,946 |
| TACI(d1-29, d111-154)-Fc5 | ZC24,903 | ZC28,978 | ZC28,979 | ZC24,946 |
| TACI(d1-29, d120-154)-Fc5 | ZC24,903 | ZC28,981 | ZC28,980 | ZC24,946 |

TABLE 3

Oligonucleotide Sequences

| Primer | Nucleotide Sequence | SEQ ID NO. |
|---|---|---|
| ZC24,903 | 5' TATTAGGCCGGCCACCATGGATGCAATGA 3' | 27 |
| ZC24,955 | 5' TGAAGATTTGGGCTCCTTGAGACCTGGGA 3' | 28 |
| ZC24,952 | 5' TCCCAGGTCTCAAGGAGCCCAAATCTTCA 3' | 29 |
| ZC24,946 | 5' TAATTGGCGCGCCTCTAGATTATTTACCCGGAGACA 3' | 30 |
| ZC24,951 | 5' TGAAGATTTGGGCTCGTTCTCACAGAAGTA 3' | 31 |
| ZC24,949 | 5' ATACTTCTGTGAGAACGAGCCCAAATCTTCA 3' | 32 |
| ZC28,978 | 5' TTTGGGCTCGCTCCTGAGCTTGTTCTCACA 3' | 33 |
| ZC28,979 | 5' CTCAGGAGCGAGCCCAAATCTTCAGACA 3' | 34 |
| ZC28,981 | 5' TTTGGGCTCCCTGAGCTCTGGTGGAA 3' | 35 |
| ZC28,980 | 5' GAGCTCAGGGAGCCCAAATCTTCAGACA 3' | 36 |

The first round of PCR amplifications consisted of two reactions for each of the four amino terminal truncated versions. The two reactions were performed separately using the 5' and 3' TACI oligonucleotides in one reaction, and the 5' and 3'Fc5 oligonucleotides in another reaction for each version. The conditions of the first round PCR amplification were as follows. To a 25 µl final volume was added approximately 200 ng template DNA, 2.5 µl 10× Pfu reaction Buffer (Stratagene), 2 µl of 2.5 mM dNTPs, 0.5 µl of 20 µM each 5' oligonucleotide and 3' oligonucleotide, and 0.5 µl Pfu polymerase (2.5 units, Stratagene). The amplification thermal profile consisted of 94° C. for 3 minutes, 35 cycles at 94° C. for 15 seconds, 50° C. for 15 seconds, 72° C. for 2 minutes, followed by a 2 minute extension at 72° C. The reaction products were fractionated by agarose gel electrophoresis, and the bands corresponding to the predicted sizes were excised from the gel and recovered using a QIAGEN QIAQUICK Gel Extraction Kit (Qiagen), according to the manufacturer's instructions.

The second round of PCR amplification, or overlap PCR amplification reaction, was performed using the gel purified fragments from the first round PCR as DNA template. The conditions of the second round PCR amplification were as follows. To a 25 µl final volume was added approximately 10 ng template DNA each of the TACI fragment and the Fc5 fragment, 2.5 µl 10× Pfu reaction Buffer (Stratagene), 2 µl of 2.5 mM dNTPs, 0.5 µl of 20 µM each ZC24,903 (SEQ ID NO:27) and ZC24,946 (SEQ ID NO:30) and 0.5 µl Pfu polymerase (2.5 units, Stratagene). The amplification thermal profile consisted of 94° C. for 1 minute, 35 cycles at 94° C. for 15 seconds, 55° C. for 15 seconds, 72° C. for 2 minutes, followed by a 2 minute extension at 72° C. The reaction products were fractionated by agarose gel electrophoresis, and the bands corresponding to the predicted sizes were excised from the gel and recovered using a QIAGEN QIAQUICK Gel Extraction Kit (Qiagen), according to the manufacturer's instructions.

Each of the four versions of the amino terminal truncated TACI-Fc PCR products were separately cloned using Invitrogen's ZEROBLUNT TOPO PCR Cloning Kit following the manufacturer's recommended protocol. Table 4 identifies the nucleotide and amino acid sequences of these TACI-Fc constructs.

TABLE 4

Sequences of TACI-Fc Variants

| | SEQ ID Nos. | |
|---|---|---|
| Designation of TACI-Fc | Nucleotide | Amino Acid |
| TACI(d1-29)-Fc5 | 18 | 19 |
| TACI(d1-29, d107-154)-Fc5 | 20 | 21 |
| TACI(d1-29, d111-154)-Fc5 | 22 | 23 |
| TACI(d1-29, d120-154)-Fc5 | 24 | 25 |

After the nucleotide sequences were verified, plasmids comprising each of the four versions of the amino terminal truncated TACI-Fc fusions were digested with FseI and AscI to release the amino acid encoding segments. The FseI-AscI fragments were ligated into a mammalian expression vector containing a CMV promoter and an SV40 poly A segment. Expression vectors were introduced into Chinese hamster ovary cells as described below.

Example 2

Production of TACI-Fc Proteins by Chinese Hamster Ovary Cells

The TACI-Fc expression constructs were used to transfect, via electroporation, suspension-adapted Chinese hamster ovary (CHO) DG44 cells grown in animal protein-free medium (Urlaub et al., Som. Cell. Molec. Genet. 12:555 (1986)). CHO DG44 cells lack a functional dihydrofolate reductase gene due to deletions at both dihydrofolate reductase chromosomal locations. Growth of the cells in the presence of increased concentrations of methotrexate results in the amplification of the dihydrofolate reductase gene, and the linked recombinant protein-encoded gene on the expression construct.

CHO DG44 cells were passaged in PFCHO media (JRH Biosciences, Lenexa, Kans.), 4 mM L-Glutamine (JRH Biosciences), and 1× hypothanxine-thymidine supplement (Life Technologies), and the cells were incubated at 37° C. and 5% $CO_2$ in Corning shake flasks at 120 RPM on a rotating shaker platform. The cells were transfected separately with linearized expression plasmids. To ensure sterility, a single ethanol precipitation step was performed on ice for 25 minutes by combining 200 µg of plasmid DNA in an Eppendorf tube with 20 µl of sheared salmon sperm carrier DNA (5'→3' Inc. Boulder, Colo., 10 mg/ml), 22 µl of 3M NaOAc (pH 5.2), and 484 µl of 100% ethanol (Gold Shield Chemical Co., Hayward, Calif.). After incubation, the tube was centrifuged at 14,000 RPM in a microfuge placed in a 4° C. cold room, the supernatant removed and the pellet washed twice with 0.5 ml of 70% ethanol and allowed to air dry.

The CHO DG44 cells were prepared while the DNA pellet was drying by centrifuging $10^6$ total cells (16.5 ml) in a 25 ml conical centrifuge tube at 900 RPM for 5 minutes. The CHO DG44 cells were resuspended into a total volume of 300 µl of PFCHO growth media, and placed in a Gene-Pulser Cuvette with a 0.4 cm electrode gap (Bio-Rad). The DNA, after approximately 50 minutes of drying time, was resuspended into 500 µl of PFCHO growth media and added to the cells in the cuvette so that the total volume did not exceed 800 µl and was allowed to sit at room temperature for 5 minutes to decrease bubble formation. The cuvette was placed in a Bio-Rad Gene Pulser II unit set at 0.296 kV (kilovolts) and 0.950 HC (high capacitance) and electroporated immediately.

The cells were incubated 5 minutes at room temperature before placement in 20 ml total volume of PFCHO media in a CoStar T-75 flask. The flask was placed at 37° C. and 5% $CO_2$ for 48 hours when the cells were then counted by hemocytometer utilizing trypan blue exclusion and put into PFCHO selection media without hypothanxine-thymidine supplement and containing 200 mM methotrexate (Cal Biochem).

Upon recovery of the methotrexate selection process, the conditioned media containing the secreted TACI-Fc proteins were examined by Western Blot analysis.

Example 3

Combination of Atacicept and MMF in Mice

Atacicept and MMF (CellCept) co-administration was tested in a 28-day study in CD-1 mice. One hundred fifty animals were distributed among four treatment groups. Group 1 received vehicle control articles used for both atacicept and MMF using the same route and regimen used for each test article. Group 2 received MMF (351 mg/kg) via daily oral gavage. Group 3 received atacicept (20 mg/kg) three times weekly via subcutaneous injection. Group 4 received atacicept (20 mg/kg, 3×/week, SC) and MMF (351 mg/kg, daily, oral), typically administered within 30 minutes of each other. The administered dose of MMF was chosen as the maximum feasible dose in mice, and mimicked the human equivalent dose for a 70 kg human of 29 mg/kg used for liver transplant patients (approximately 2 g/day) using body surface area to scale the human dose to mice.

Animals were sacrificed at baseline (Day-1) and Days 14, 28 (last day of treatment), 42, 56, and 112. Mice were checked daily for mortality, abnormalities, and signs of pain or distress. Body weights were measured and recorded on Day-1 of the study and weekly thereafter, and prior to sacrifice. Blood was collected from sacrificed animals for comprehensive hematology and serum chemistry analyses, flow cytometric analyses of lymphocyte subtypes, and total serum IgG, IgM, and IgA concentrations. Total serum IgG, IgM, and IgA were measured using a Comprehensive necropsies were conducted on sacrificed animals for evaluation of organ weight changes, gross pathology, and histopathology.

Total IgG levels were evaluated using a mouse IgG ELISA quantitation kit (Catalog #E90-131, Bethyl Laboratories, Montgomery, Tex.), combined with the ELISA Starter Accessory Package (Catalog #E101, Bethyl Laboratories, Montgomery, Tex.). All liquid handling was performed using the integrated Freedom Evo 150 liquid handling system and Columbus Washer (TECAN, Denmark). Microtiter wells were coated with affinity purified goat anti-mouse IgG and incubated at room temperature for 1 hour. The wells were aspirated, washed with wash solution, and then blocked with blocking solution for 30 minutes. The blocking solution was removed, the plates washed, and samples/standards added in duplicate. After 1 hour, the samples/standards were aspirated and the wells washed with Wash Solution. Horseradish peroxidase-conjugated goat anti-mouse IgG was added, and the wells were incubated at room temperature for 1 hour. Unbound conjugated antibody was removed by washing, and the amount of conjugate remaining in the well was measured by incubation with TMB substrate (Bethyl Laboratories, Montgomery, Tex.) for 10 minutes. The color reaction was stopped with addition of 2 M $H_2SO_4$, and the resulting absorbance (OD-450) was measured on a Spectramax 190 microplate reader.

Data calculations for total IgG were performed as follows: the average zero standard (plate blank) OD-450 value was subtracted from each sample and standard, and the duplicate readings were averaged. A standard curve was created by plotting the mean OD for each standard vs. concentration using a four-parameter logistic curve fit. Sample concentrations were obtained by interpolation from the standard curve. The mean sample concentration was multiplied by the dilution factor. Data analyzed using SoftMax®Pro software included OD values, the standard curve(s), the standard deviation and % CV between replicates, and the interpolated value of the unknown(s).

Total IgM levels were evaluated using a mouse IgM ELISA quantitation kit (Catalog #E90-101, Bethyl Laboratories, Montgomery, Tex.), combined with the ELISA Starter Accessory Package (Catalog #E101, Bethyl Laboratories, Montgomery, Tex.). All liquid handling was performed using the integrated Freedom Evo 150 liquid handling system and Columbus Washer (TECAN, Denmark). Microtiter wells were coated with affinity purified goat anti-mouse IgM and incubated at room temperature for 1 hour. The wells were aspirated, washed with wash solution, and then blocked with blocking solution for 30 minutes. The blocking solution was removed, the plates washed, and samples/standards added in duplicate. After 1 hour, the samples/standards were aspirated and the wells washed with wash solution. Horseradish peroxidase-conjugated goat anti-mouse IgM was added, and the wells were incubated at room temperature for 1 hour. Unbound conjugated antibody was removed by washing, and the amount of conjugate remaining in the well was measured by incubation with TMB substrate (Bethyl Laboratories, Montgomery, Tex.) for 10 minutes. The color reaction was stopped with addition of 2 M $H_2SO_4$, and the resulting absorbance (OD-450) was measured on a Spectramax 190 microplate reader.

Data Calculations for Total IgM were Performed as Follows:

The average zero standard (plate blank) OD-450 value was subtracted from each sample and standard, and the duplicate readings were averaged. A standard curve was created by plotting the mean OD for each standard vs. concentration using a four-parameter logistic curve fit. Sample concentrations were obtained by interpolation from the standard curve. The mean sample concentration was multiplied by the dilution factor. Data analyzed with SoftMax®Pro software, included OD values, the standard curve(s), the standard deviation and % CV between replicates, and the interpolated value of the unknown(s).

Total IgA levels were evaluated using a mouse IgA ELISA quantitation kit (Catalog #E90-103, Bethyl Laboratories, Montgomery, Tex.), combined with the ELISA Starter Accessory Package (Catalog #E101, Bethyl Laboratories, Montgomery, Tex.). All liquid handling was performed using the integrated Freedom Evo 150 liquid handling system and Columbus Washer (TECAN, Denmark). Microtiter wells were coated with affinity purified goat anti-mouse IgA and incubated at room temperature for 1 hour. The wells were aspirated, washed with wash solution, and then blocked with blocking solution for 30 minutes. The blocking solution was removed, the plates washed, and samples/standards added in duplicate. After 1 hour, the samples/standards were aspirated and the wells washed with wash solution. Horseradish peroxidase-conjugated goat anti-mouse IgM was added, and the wells were incubated at room temperature for 1 hour. Unbound conjugated antibody was removed by washing, and the amount of conjugate remaining in the well was measured by incubation with TMB substrate (Bethyl Laboratories, Montgomery, Tex.) for 10 minutes. The color reaction was stopped with addition of 2 M $H_2SO_4$, and the resulting absorbance (OD-450) was measured on a Spectramax 190 microplate reader.

Data Calculations for Total IgA were Performed as Follows:

The average zero standard (plate blank) OD-450 value was subtracted from each sample and standard, and the duplicate readings were averaged. A standard curve was created by plotting the mean OD for each standard vs. concentration using a four-parameter logistic curve fit. Sample concentrations were obtained by interpolation from the standard curve. The mean sample concentration was multiplied by the dilution factor. Data analyzed with SoftMax®Pro software, included OD values, the standard curve(s), the standard deviation and % CV between replicates, and the interpolated value of the unknown(s).

Figure 2:
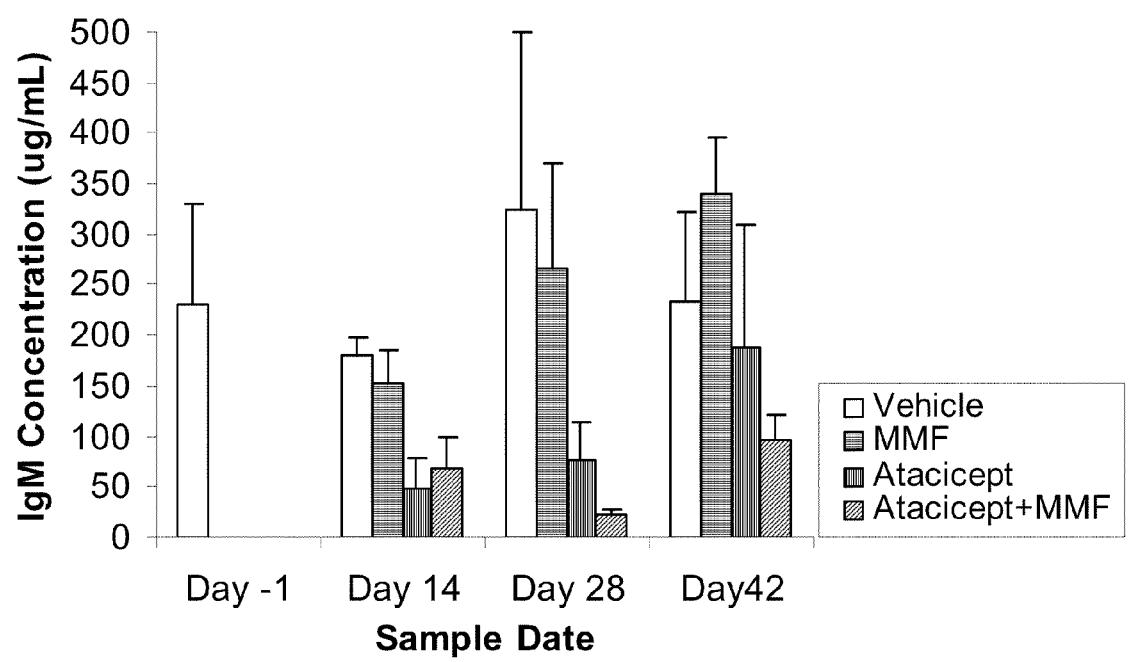
FIG. 2 graphs the mean value (±standard deviation) of IgM for the four treatment groups—vehicle, MMF only, atacicept only, and atacicept and MMF. All pairwise comparisons of these values were statistically significant (p<0.05) using log-transformed data other than vehicle vs. MMF alone.
Figure 3:
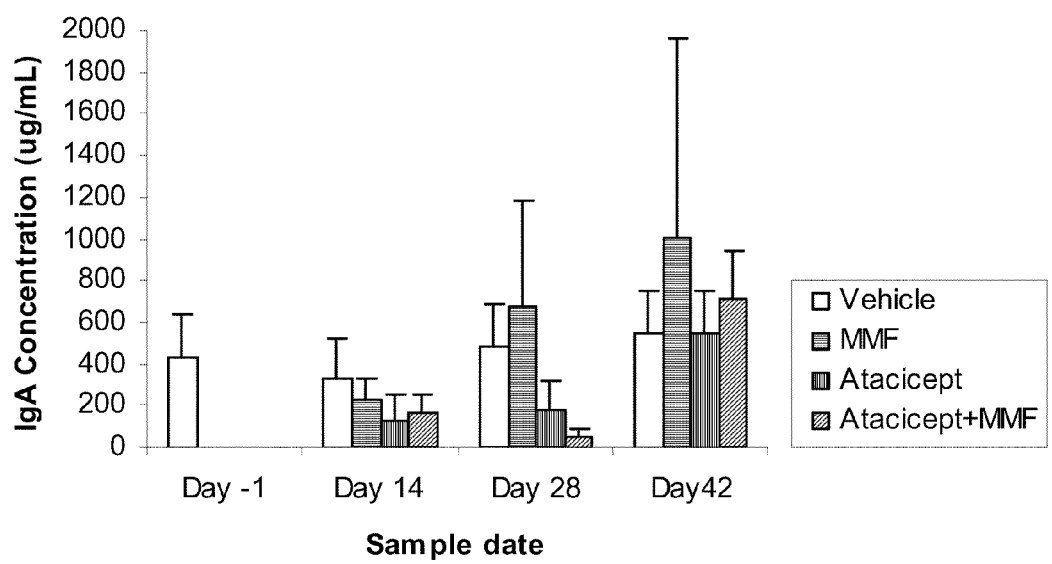
FIG. 3 graphs the mean value (±standard deviation) of IgA for the four treatment groups—vehicle, MMF only, atacicept only, and atacicept and MMF. All pairwise comparisons of these values were statistically significant (p<0.05) using log-transformed data other than vehicle vs. MMF alone.

The mean results of the change in immunoglobulin measurements are recorded in Table 5 below and graphically in FIGS. 1, 2, and 3.

TABLE 5

Numeric Mean IgG, IgM, and IgA results for Day 28 and Difference from Vehicle (μg/mL)

|  | Vehicle (V) | MMF | Atacicept (A) | Atacicept + MMF (A + M) |
|---|---|---|---|---|
| IgG | 179 | 185 | 75 | 31 |
| IgM | 238 | 317 | 76 | 19 |
| IgA | 498 | 506 | 105 | 33 |

|  | Δ1 (V − MMF) | Δ2 (V − A) | Δ1 + Δ2 | Δ3 (V − (A + M)) | Δ3 Compared to Δ1 + Δ2 |
|---|---|---|---|---|---|
| IgG | −6 | 104 | 98 | 148 | 148 > 98 |
| IgM | −79 | 162 | 83 | 219 | 219 > 83 |
| IgA | −8 | 393 | 385 | 464 | 464 > 385 |

As can be seen from these calculations, the combination has a synergistic effect on the reduction of immunoglobin for all three types (i.e., the mean change from vehicle with the combination (Δ3) is more than the addition of the mean change from vehicle to MMF alone (Δ1) with the mean change from vehicle to Atacicept alone (Δ2) (or, mathematically, Δ3>Δ1+Δ2)).

Conclusion

The experiments herein demonstrated surprising results in that the combination of immunosuppressive drugs and BLyS and/or APRIL antagonists, such as MMF and atacicept, resulted in a synergistic depletion of Ig levels compared to the level of reduction with immunosuppressive drugs and BLyS and/or APRIL antagonists alone.

Example 4

Repeat and Extension of Atacicept and MMF Combination Experiment

Using similar procedures to those described in Example 3 and dosing until day 91, the results of Example 3 were replicated and extended in time to days 35, 91, 126, and 182. The results of this experiment confirmed the synergistic effect of Atacicept and MMF on the mean levels of immunoglobulin for at least one of the three types of immunoglobulin at each time point. The synergistic results are summarized in Tables 6 below.

TABLE 6

Synergistic Results of the Numeric Mean for IgG, IgM, and IgA results for Extended Experiment and Difference from Vehicle (μg/mL)

| Sample Day | Immunoglobulin Type | Vehicle (V) | MMF | Atacicept (A) | Atacicept + MMF (A + M) |
|---|---|---|---|---|---|
| 35 | IgG | 519.7 | 940.13 | 261.35 | 148.59 |
| 35 | IgM | 105.7 | 141.34 | 5.54 | 5.11 |

TABLE 6-continued

Synergistic Results of the Numeric Mean for IgG, IgM, and IgA results for
Extended Experiment and Difference from Vehicle (µg/mL)

| 91  | IgG | 697.01  | 1192.87 | 191.84 | 128.22 |
|-----|-----|---------|---------|--------|--------|
| 91  | IgA | 924.36  | 1764.55 | 37.53  | 0      |
| 126 | IgA | 1113.48 | 1467.05 | 817.22 | 778.05 |
| 182 | IgM | 73.95   | 53.77   | 73.75  | 47.63  |

| Sample Day | Immunoglobulin Type | Δ1 (V − MMF) | Δ2 (V − A) | Δ1 + Δ2 | Δ3 (V − (A + M)) | Δ3 Compared to Δ1 + Δ2 |
|---|---|---|---|---|---|---|
| 35  | IgG | −420.43 | 258.35 | −162.08 | 371.11 | 371.11 > −162.08 |
| 35  | IgM | −35.64  | 100.16 | 64.52   | 100.59 | 100.59 > 64.52   |
| 91  | IgG | −495.86 | 505.17 | 9.31    | 568.79 | 568.79 > 9.31    |
| 91  | IgA | −840.19 | 886.83 | 46.64   | 924.36 | 924.36 > 46.64   |
| 126 | IgA | −353.57 | 296.26 | 57.31   | 335.43 | 335.43 > 57.31   |
| 182 | IgM | 20.18   | .20    | 20.38   | 26.32  | 26.32 > 20.38    |

It should be noted that as selected immunoglobulin subtypes reached maximal suppression, the ability to observe the synergistic effect is masked because of the low absolute numbers. This "masking effect" explains why the synergy was less consistently seen across all three immunoglobulin subtypes at later time points. In sum, these results confirm the synergistic effects of the combination of Atacicept and MMF on the numeric mean of the levels of the indicated immunoglobulin types seen in Example 3 and extend that conclusion over a time course from 35, 91, 126, and 182 days.

For the sake of completeness, the following describes the experimental groups, doses, volumes administered and concentrations used in this repeat and extension experiment:

TABLE 7

| Group | | No of animals | Dose (mg/kg/day) | Dose route | Dose schedule |
|---|---|---|---|---|---|
| 1 | Vehicle 1 + | 20 M + | 0 | s.c. | 3/week |
|   | Vehicle 2   | 20 F   | 0 | oral | daily  |
| 2 | Atacicept   | 20 M + 20 F | 20 | s.c. | 3/week |
| 3 | MMF         | 20 M + 20 F | 350 | oral | daily |
| 4 | Atacicept + | 20 M + | 20  | s.c. | 3/week |
|   | MMF         | 20 F   | 350 | oral | daily |

Administration regimen
ATACICEPT: every other day, for 3 days/week, by subcutaneous route.
MMF: daily, by oral route.

Group 1 received both the vehicle for ATACICEPT and the vehicle for CellCept at the same treatment frequency as the treated groups. Group 2 was treated with only ATACICEPT Group 3 received only CellCept. Group 4 received CellCept oral gavage followed by ATACICEPT s.c. injection within a period of approximately 30 minutes. The day of the first treatment was considered day 1 of the study. Throughout the study period clinical observations, hematological and blood chemistry tests, toxicokinetics and additional investigations were carried out.

Total IgG, IgM and IgA Determinations/Satellite Groups 9, 10, 11 and 12

Additional satellite groups of animals were used for total immunoglobulin determinations and antibody determination. They were treated and weighed according to the same procedures as the main study.

TABLE 8

| Group/sex (N° of animals) | ATACICEPT Doses (mg/kg/day) Subcutaneous | MMF Doses (mg/kg/day) Oral |
|---|---|---|
| 9 M (15)  | 0    | 0    |
| 9 F (15)  |      |      |
| 10 M (12) | 20   | n.a. |
| 10 F (12) |      |      |
| 11 M (12) | n.a. | 350  |
| 11 F (12) |      |      |
| 12 M (12) | 20   | 350  |
| 12 F (12) |      |      |

Animals were housed in 3 mice/sex/cage.

Blood samples were collected from 3 animals/sex/group (in progressive numerical order) for the determination of IgG, IgM and IgA serum levels at the following times:
from animals of the control group (gr. 9): Pre-dose
from animals of groups 9, 10, 11 and 12:
  on day 34 of the 5-week treatment period
  on day 90 of the 13-week treatment period
  on day 34 of the 5-week recovery period
  on day 90 of the 13-week recovery period The blood (at least 0.8-1 mL) was collected at sacrifice from the abdominal aorta of mice after they have been completely anaesthetized with diethyl ether.

Samples were collected in tubes without any anticoagulant and allowed to clot for about 1 hour at room temperature. The clot were spun down by centrifugation at 3000 rpm at +4° C. for 15 minutes. Blood cells were discarded and the serum banked in 100 µL aliquots (four aliquots for every single analysis) and stored at −80° C. until analysis. Total IgG, IgM and IgA levels were determined by validated ELISA methods.

Sacrifice was performed at the end of the 5-week treatment period on 4 animals/sex/group (the first ones in numerical order); at the end of the 13-week treatment period on 8 animals/sex/group (the second ones in numerical order); at the end of the 5-week recovery period on 4 animals/sex/group (the first recovered animals in numerical order); and at the end of the 13-week recovery period on 4 animals/sex/group (the remaining animals).

CONCLUSION

The extension experiment reported herein support the results of Example 3 where it was surprisingly shown that the combination of immunosuppressive drugs and BLyS and/or APRIL antagonists, such as MMF and atacicept, resulted in a synergistic depletion of Ig levels compared to the level of reduction with immunosuppressive drugs and BLyS and/or APRIL antagonists alone.

REFERENCES

References cited within this application, including patents, published applications and other publications are herein incorporated by reference.

We claim:

1. A method of reducing immunoglobulin levels in a mammal comprising administering a BLyS antagonist and mycophenolate mofetil (MMF), wherein said B Lymphocyte Stimulator (BLyS) antagonist and said MMF are administered in an amount such that the combination of the MMF and the BlyS antagonist act at synergistically to reduce immunoglobulin levels said BLyS antagonist comprises the TACI-Fc protein set forth in SEQ ID NO: 23, wherein the modified tissue plasminogen activation signal sequence has been removed from the protein set forth in SEQ ID NO: 23.

2. The method of claim 1 wherein the immunoglobulin level that is reduced is selected from the group consisting of IgM, IgG, and IgA.

3. A method of alleviating a B-cell regulated autoimmune disorder comprising administering to a patient suffering from the disorder a therapeutically effective amount of a B Lymphocyte Stimulator (BLyS) antagonist and mycophenolate mofetil (MMF), wherein the B-cell regulated autoimmune disorder arises from antibodies that are directed against said patient's own (self) antigens or tissues wherein said BLyS antagonist and said MMF are administered in an amount wherein the combination of the MMF and the BlyS antagonist act synergistically to reduce immunoglobulin levels, said BLyS antagonist comprises the TACI-Fc protein set forth in SEQ ID NO: 23 and wherein the modified tissue plasminogen activation signal sequence has been removed from the protein set forth in SEQ ID NO: 23.

4. The method of claim 3, wherein the immunoglobulin level that is reduced is selected from the group consisting of IgM, IgG, and IgA.

5. The method of claim 3 wherein the autoimmune disease is selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpuria (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes, mellitus, Reynauld's syndrome, Sjorgen's syndrome, glomerulonephritis, autoimmune hepatitis, and autoimmune thyroiditis.

6. The method of claim 5 wherein the autoimmune disease is lupus nephritis.

7. The method of claim 3 wherein the BLyS antagonist is administered at a dosage of about 1 to about 2.5 mg/kg and the MMF is administered at a dosage of about 1 to about 4 mg/kg.

8. The method of claim 3 wherein the BLyS antagonist and the MMF is administered in conjunction with therapy using a second immunosuppressive drug selected from the group consisting of nonsteroidal anti-inflammatory drugs (NSAIDs), glucocorticoid, prednisone, and disease-modifying antirheumatic drugs (DMARDs).

9. A method of reducing immunoglobulin levels in a mammal comprising administering an A Proliferation Inducing Ligand (APRIL) antagonist and mycophenolate mofetil (MMF), wherein said April antagonist and said MMF are administered in an amount such that the combination of the MMF and the APRIL antagonist act to synergistically reduce immunoglobulin levels, said APRIL antagonist comprises the TACI-Fc protein set forth in SEQ ID NO: 23 wherein the modified tissue plasminogen activation signal sequence has been removed from the protein set forth in SEQ ID NO: 23.

10. A method of alleviating a B-cell regulated autoimmune disorder comprising administering to a patient suffering from the disorder a therapeutically effective amount of an A Proliferation Inducing Ligand (APRIL) antagonist and mycophenolate mofetil (MMF), wherein the B-cell regulated autoimmune disorder arises from antibodies that are directed against said patient's own (self) antigens or tissues wherein said April antagonist and said MMF are administered in an amount wherein the combination of the MMF and the APRIL antagonist act synergistically to reduce immunoglobulin levels, said APRIL antagonist comprises the TACI-Fc protein set forth in SEQ ID NO: 23 wherein the modified tissue plasminogen activation signal sequence has been removed from said protein set forth in SEQ ID NO: 23.

11. The method of claim 9, wherein the immunoglobulin level that is reduced is selected from the group consisting of IgM, IgG, and IgA.

12. The method of claim 10, wherein the autoimmune disease is selected from the group consisting of rheumatoid arthritis, juvenile rheumatoid arthritis, systemic lupus erythematosus (SLE), lupus nephritis (LN), Wegener's disease, inflammatory bowel disease, idiopathic thrombocytopenic purpuria (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes, mellitus, Reynauld's syndrome, Sjorgen's syndrome, glomerulonephritis, autoimmune hepatitis, and autoimmune thyroiditis.

13. The method of claim 11, wherein the autoimmune disease is lupus nephritis.

14. The method of claim 10, wherein the APRIL antagonist and the MMF is administered in conjunction with therapy using a second immunosuppressive drug selected from the group consisting of nonsteroidal anti-inflammatory drugs (NSAIDs), glucocorticoid, prednisone, and disease-modifying antirheumatic drugs (DMARDs).

* * * * *

UNITED STATES PATENT AND TRADEMARK OFFICE
CERTIFICATE OF CORRECTION

PATENT NO. : 8,852,591 B2  
APPLICATION NO. : 12/057133  
DATED : October 7, 2014  
INVENTOR(S) : Ponce, Jr. et al.

Page 1 of 1

It is certified that error appears in the above-identified patent and that said Letters Patent is hereby corrected as shown below:

ON THE TITLE PAGE

Item (73), delete "Zymogenetics, Inc." and insert -- ZymoGenetics, Inc. --.

IN THE CLAIMS

Column 106 (Claim 13), line 56, delete "11" and insert -- 12 --.

Signed and Sealed this  
Seventeenth Day of March, 2015

Michelle K. Lee  
*Director of the United States Patent and Trademark Office*

SEQUENCE LISTING

```
<160> NUMBER OF SEQ ID NOS: 41

<210> SEQ ID NO 1
<211> LENGTH: 1377
<212> TYPE: DNA
<213> ORGANISM: homo sapiens
<220> FEATURE:
<221> NAME/KEY: CDS
<222> LOCATION: (14)...(892)

<400> SEQUENCE: 1
agcatcctga gta atg agt ggc ctg ggc cgg agc agg cga ggt ggc cgg           49
             Met Ser Gly Leu Gly Arg Ser Arg Arg Gly Gly Arg
              1               5                  10 agc cgt gtg gac cag gag gag cgc ttt cca cag ggc ctg tgg acg ggg          97
Ser Arg Val Asp Gln Glu Glu Arg Phe Pro Gln Gly Leu Trp Thr Gly
            15                  20                  25 gtg gct atg aga tcc tgc ccc gaa gag cag tac tgg gat cct ctg ctg         145
Val Ala Met Arg Ser Cys Pro Glu Glu Gln Tyr Trp Asp Pro Leu Leu
        30                  35                  40 ggt acc tgc atg tcc tgc aaa acc att tgc aac cat cag agc cag cgc         193
Gly Thr Cys Met Ser Cys Lys Thr Ile Cys Asn His Gln Ser Gln Arg
 45                  50                  55                  60 acc tgt gca gcc ttc tgc agg tca ctc agc tgc cgc aag gag caa ggc         241
Thr Cys Ala Ala Phe Cys Arg Ser Leu Ser Cys Arg Lys Glu Gln Gly
                 65                  70                  75 aag ttc tat gac cat ctc ctg agg gac tgc atc agc tgt gcc tcc atc         289
Lys Phe Tyr Asp His Leu Leu Arg Asp Cys Ile Ser Cys Ala Ser Ile
             80                  85                  90 tgt gga cag cac cct aag caa tgt gca tac ttc tgt gag aac aag ctc         337
Cys Gly Gln His Pro Lys Gln Cys Ala Tyr Phe Cys Glu Asn Lys Leu
         95                 100                 105 agg agc cca gtg aac ctt cca cca gag ctc agg aga cag cgg agt gga         385
Arg Ser Pro Val Asn Leu Pro Pro Glu Leu Arg Arg Gln Arg Ser Gly
    110                 115                 120 gaa gtt gaa aac aat tca gac aac tcg gga agg tac caa gga ttg gag         433
Glu Val Glu Asn Asn Ser Asp Asn Ser Gly Arg Tyr Gln Gly Leu Glu
125                 130                 135                 140 cac aga ggc tca gaa gca agt cca gct ctc ccg ggg ctg aag ctg agt         481
His Arg Gly Ser Glu Ala Ser Pro Ala Leu Pro Gly Leu Lys Leu Ser
                145                 150                 155 gca gat cag gtg gcc ctg gtc tac agc acg ctg ggc ctg tgc ctg tgt         529
Ala Asp Gln Val Ala Leu Val Tyr Ser Thr Leu Gly Leu Cys Leu Cys
            160                 165                 170 gcc gtc ctc tgc tgc ttc ctg gtg gcg gtg gcc tgc ttc ctc aag aag         577
Ala Val Leu Cys Cys Phe Leu Val Ala Val Ala Cys Phe Leu Lys Lys
        175                 180                 185 agg ggg gat ccc tgc tcc tgc cag ccc gcc tca ggg ccc gtc caa agt         625
Arg Gly Asp Pro Cys Ser Cys Gln Pro Arg Ser Arg Pro Arg Gln Ser
    190                 195                 200 ccg gcc aag tct tcc cag gat cac gcg atg gaa gcc ggc agc cct gtg         673
Pro Ala Lys Ser Ser Gln Asp His Ala Met Glu Ala Gly Ser Pro Val
```

-continued

```
                205                 210                 215                 220 agc aca tcc ccc gag cca gtg gag acc tgc agc ttc tgc ttc cct gag        721
Ser Thr Ser Pro Glu Pro Val Glu Thr Cys Ser Phe Cys Phe Pro Glu
                    225                 230                 235 tgc agg gcg ccc acg cag gag agc gca gtc acg cct ggg acc ccc gac        769
Cys Arg Ala Pro Thr Gln Glu Ser Ala Val Thr Pro Gly Thr Pro Asp
                    240                 245                 250 ccc act tgt gct gga agg tgg ggg tgc cac acc agg acc aca gtc ctg        817
Pro Thr Cys Ala Gly Arg Trp Gly Cys His Thr Arg Thr Thr Val Leu
                    255                 260                 265 cag cct tgc cca cac atc cca gac agt ggc ctt ggc att gtg tgt gtg        865
Gln Pro Cys Pro His Ile Pro Asp Ser Gly Leu Gly Ile Val Cys Val
                    270                 275                 280 cct gcc cag gag ggg ggc cca ggt gca taaatggggg tcagggaggg              912
Pro Ala Gln Glu Gly Gly Pro Gly Ala
285                 290 aaaggaggag ggagagagat ggagaggagg ggagagagaa agagaggtgg ggagaggga        972 gagagatatg aggagagaga gacagaggag gcagaaaggg agagaaacag aggagacaga      1032
gagggagaga gagacagagg gagagagaga cagaggggaa gagaggcaga gagggaaaga      1092
ggcagagaag gaaagagaca ggcagagaag gagagaggca gagagggaga gaggcagaga      1152
gggagagagg cagagagaca gagagggaga gagggacaga gagagataga gcaggaggtc      1212
ggggcactct gagtcccagt tcccagtgca gctgtaggtc gtcatcacct aaccacacgt      1272
gcaataaagt cctcgtgcct gctgctcaca gcccccgaga gcccctcctc ctggagaata      1332
aaacctttgg cagctgccct tcctcaaaaa aaaaaaaaaa aaaaa                      1377
```

<210> SEQ ID NO 2
<211> LENGTH: 293
<212> TYPE: PRT
<213> ORGANISM: homo sapiens

<400> SEQUENCE: 2

```
Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
                20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
                100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
        130                 135                 140

Glu Ala Ser Pro Ala Leu Pro Gly Leu Lys Leu Ser Ala Asp Gln Val
145                 150                 155                 160

Ala Leu Val Tyr Ser Thr Leu Gly Leu Cys Leu Cys Ala Val Leu Cys
                165                 170                 175
```

-continued

```
Cys Phe Leu Val Ala Val Ala Cys Phe Leu Lys Lys Arg Gly Asp Pro
            180                 185                 190

Cys Ser Cys Gln Pro Arg Ser Arg Pro Arg Gln Ser Pro Ala Lys Ser
        195                 200                 205

Ser Gln Asp His Ala Met Glu Ala Gly Ser Pro Val Ser Thr Ser Pro
    210                 215                 220

Glu Pro Val Glu Thr Cys Ser Phe Cys Phe Pro Glu Cys Arg Ala Pro
225                 230                 235                 240

Thr Gln Glu Ser Ala Val Thr Pro Gly Thr Pro Asp Pro Thr Cys Ala
                245                 250                 255

Gly Arg Trp Gly Cys His Thr Arg Thr Thr Val Leu Gln Pro Cys Pro
            260                 265                 270

His Ile Pro Asp Ser Gly Leu Gly Ile Val Cys Val Pro Ala Gln Glu
        275                 280                 285

Gly Gly Pro Gly Ala
    290
```

<210> SEQ ID NO 3
<211> LENGTH: 586
<212> TYPE: DNA
<213> ORGANISM: homo sapiens
<220> FEATURE:
<221> NAME/KEY: CDS
<222> LOCATION: (27)...(578)

<400> SEQUENCE: 3

```
gcagcttgtg cggcggcgtc ggcacc atg agg cga ggg ccc cgg agc ctg cgg        53
                               Met Arg Arg Gly Pro Arg Ser Leu Arg
                                 1               5 ggc agg gac gcg cca gcc ccc acg ccc tgc gtc ccg gcc gag tgc ttc        101
Gly Arg Asp Ala Pro Ala Pro Thr Pro Cys Val Pro Ala Glu Cys Phe
 10                  15                  20                  25 gac ctg ctg gtc cgc cac tgc gtg gcc tgc ggg ctc ctg cgc acg ccg        149
Asp Leu Leu Val Arg His Cys Val Ala Cys Gly Leu Leu Arg Thr Pro
                 30                  35                  40 cgg ccg aaa ccg gcc ggg gcc agc agc cct gcg ccc agg acg gcg ctg        197
Arg Pro Lys Pro Ala Gly Ala Ser Ser Pro Ala Pro Arg Thr Ala Leu
             45                  50                  55 cag ccg cag gag tcg gtg ggc gcg ggg gcc ggc gag gcg gcg ctg ccc        245
Gln Pro Gln Glu Ser Val Gly Ala Gly Ala Gly Glu Ala Ala Leu Pro
         60                  65                  70 ctg ccc ggg ctg ctc ttt ggc gcc ccc gcg ctg ctg ggc ctg gca ctg        293
Leu Pro Gly Leu Leu Phe Gly Ala Pro Ala Leu Leu Gly Leu Ala Leu
     75                  80                  85 gtc ctg gcg ctg gtc ctg gtg ggt ctg gtg agc tgg agg cgg cga cag        341
Val Leu Ala Leu Val Leu Val Gly Leu Val Ser Trp Arg Arg Arg Gln
 90                  95                 100                 105 cgg cgg ctt cgc ggc gcg tcc tcc gca gag gcc ccc gac gga gac aag        389
Arg Arg Leu Arg Gly Ala Ser Ser Ala Glu Ala Pro Asp Gly Asp Lys
                110                 115                 120 gac gcc cca gag ccc ctg gac aag gtc atc att ctg tct ccg gga atc        437
Asp Ala Pro Glu Pro Leu Asp Lys Val Ile Ile Leu Ser Pro Gly Ile
            125                 130                 135 tct gat gcc aca gct cct gcc tgg cct cct cct ggg gaa gac cca gga        485
Ser Asp Ala Thr Ala Pro Ala Trp Pro Pro Pro Gly Glu Asp Pro Gly
        140                 145                 150 acc acc cca cct ggc cac agt gtc cct gtg cca gcc aca gag ctg ggc        533
Thr Thr Pro Pro Gly His Ser Val Pro Val Pro Ala Thr Glu Leu Gly
    155                 160                 165
```

```
tcc act gaa ctg gtg acc acc aag acg gcc ggc cct gag caa caa        578
Ser Thr Glu Leu Val Thr Thr Lys Thr Ala Gly Pro Glu Gln Gln
170                 175                 180 tagcaggg                                                            586

<210> SEQ ID NO 4
<211> LENGTH: 184
<212> TYPE: PRT
<213> ORGANISM: homo sapiens

<400> SEQUENCE: 4

Met Arg Arg Gly Pro Arg Ser Leu Arg Gly Arg Asp Ala Pro Ala Pro
 1               5                   10                  15

Thr Pro Cys Val Pro Ala Glu Cys Phe Asp Leu Leu Val Arg His Cys
             20                  25                  30

Val Ala Cys Gly Leu Leu Arg Thr Pro Arg Pro Lys Pro Ala Gly Ala
         35                  40                  45

Ser Ser Pro Ala Pro Arg Thr Ala Leu Gln Pro Gln Glu Ser Val Gly
     50                  55                  60

Ala Gly Ala Gly Glu Ala Ala Leu Pro Leu Pro Gly Leu Leu Phe Gly
 65                  70                  75                  80

Ala Pro Ala Leu Leu Gly Leu Ala Leu Val Leu Ala Leu Val Leu Val
                 85                  90                  95

Gly Leu Val Ser Trp Arg Arg Gln Arg Arg Leu Arg Gly Ala Ser
            100                 105                 110

Ser Ala Glu Ala Pro Asp Gly Asp Lys Asp Ala Pro Glu Pro Leu Asp
        115                 120                 125

Lys Val Ile Ile Leu Ser Pro Gly Ile Ser Asp Ala Thr Ala Pro Ala
    130                 135                 140

Trp Pro Pro Pro Gly Glu Asp Pro Gly Thr Thr Pro Pro Gly His Ser
145                 150                 155                 160

Val Pro Val Pro Ala Thr Glu Leu Gly Ser Thr Glu Leu Val Thr Thr
                165                 170                 175

Lys Thr Ala Gly Pro Glu Gln Gln
            180

<210> SEQ ID NO 5
<211> LENGTH: 995
<212> TYPE: DNA
<213> ORGANISM: homo sapiens
<220> FEATURE:
<221> NAME/KEY: CDS
<222> LOCATION: (219)...(770)

<400> SEQUENCE: 5
aagactcaaa cttagaaact tgaattagat gtggtattca atccttacg tgccgcgaag    60 acacagacag cccccgtaag aacccacgaa gcaggcgaag ttcattgttc tcaacattct   120
agctgctctt gctgcatttg ctctggaatt cttgtagaga tattacttgt ccttccaggc   180
tgttctttct gtagctccct gttttctttt tgtgatc atg ttg cag atg gct ggg   236
                                        Met Leu Gln Met Ala Gly
                                         1               5 cag tgc tcc caa aat gaa tat ttt gac agt ttg ttg cat gct tgc ata    284
Gln Cys Ser Gln Asn Glu Tyr Phe Asp Ser Leu Leu His Ala Cys Ile
             10                  15                  20 cct tgt caa ctt cga tgt tct tct aat act cct cct cta aca tgt cag    332
Pro Cys Gln Leu Arg Cys Ser Ser Asn Thr Pro Pro Leu Thr Cys Gln
         25                  30                  35
```

| | | | | | | | | | | | | | | | | |
|---|---|---|---|---|---|---|---|---|---|---|---|---|---|---|---|---|
| cgt | tat | tgt | aat | gca | agt | gtg | acc | aat | tca | gtg | aaa | gga | acg | aat | gcg | 380 |
| Arg | Tyr | Cys | Asn | Ala | Ser | Val | Thr | Asn | Ser | Val | Lys | Gly | Thr | Asn | Ala | |
| | 40 | | | | 45 | | | | 50 | | | | | | | |
| att | ctc | tgg | acc | tgt | ttg | gga | ctg | agc | tta | ata | att | tct | ttg | gca | gtt | 428 |
| Ile | Leu | Trp | Thr | Cys | Leu | Gly | Leu | Ser | Leu | Ile | Ile | Ser | Leu | Ala | Val | |
| 55 | | | | 60 | | | | | 65 | | | | | 70 | | |
| ttc | gtg | cta | atg | ttt | ttg | cta | agg | aag | ata | agc | tct | gaa | cca | tta | aag | 476 |
| Phe | Val | Leu | Met | Phe | Leu | Leu | Arg | Lys | Ile | Ser | Ser | Glu | Pro | Leu | Lys | |
| | | | 75 | | | | | 80 | | | | | 85 | | | |
| gac | gag | ttt | aaa | aac | aca | gga | tca | ggt | ctc | ctg | ggc | atg | gct | aac | att | 524 |
| Asp | Glu | Phe | Lys | Asn | Thr | Gly | Ser | Gly | Leu | Leu | Gly | Met | Ala | Asn | Ile | |
| | | | 90 | | | | | 95 | | | | | 100 | | | |
| gac | ctg | gaa | aag | agc | agg | act | ggt | gat | gaa | att | att | ctt | ccg | aga | ggc | 572 |
| Asp | Leu | Glu | Lys | Ser | Arg | Thr | Gly | Asp | Glu | Ile | Ile | Leu | Pro | Arg | Gly | |
| | | 105 | | | | | 110 | | | | | 115 | | | | |
| ctc | gag | tac | acg | gtg | gaa | gaa | tgc | acc | tgt | gaa | gac | tgc | atc | aag | agc | 620 |
| Leu | Glu | Tyr | Thr | Val | Glu | Glu | Cys | Thr | Cys | Glu | Asp | Cys | Ile | Lys | Ser | |
| 120 | | | | | 125 | | | | | 130 | | | | | | |
| aaa | ccg | aag | gtc | gac | tct | gac | cat | tgc | ttt | cca | ctc | cca | gct | atg | gag | 668 |
| Lys | Pro | Lys | Val | Asp | Ser | Asp | His | Cys | Phe | Pro | Leu | Pro | Ala | Met | Glu | |
| 135 | | | | 140 | | | | | 145 | | | | | 150 | | |
| gaa | ggc | gca | acc | att | ctt | gtc | acc | acg | aaa | acg | aat | gac | tat | tgc | aag | 716 |
| Glu | Gly | Ala | Thr | Ile | Leu | Val | Thr | Thr | Lys | Thr | Asn | Asp | Tyr | Cys | Lys | |
| | | | | 155 | | | | | 160 | | | | | 165 | | |
| agc | ctg | cca | gct | gct | ttg | agt | gct | acg | gag | ata | gag | aaa | tca | att | tct | 764 |
| Ser | Leu | Pro | Ala | Ala | Leu | Ser | Ala | Thr | Glu | Ile | Glu | Lys | Ser | Ile | Ser | |
| | | 170 | | | | | 175 | | | | | 180 | | | | |
| gct | agg | taattaacca | tttcgactcg | agcagtgcca | ctttaaaaat | cttttgtcag | | | | | | | | | | 820 |
| Ala | Arg | | | | | | | | | | | | | | | |

| | | |
|---|---|---|
| aatagatgat gtgtcagatc tctttaggat gactgtattt tcagttgcc gatacagctt | | 880 |
| tttgtcctct aactgtggaa actctttatg ttagatatat ttctctaggt tactgttggg | | 940 |
| agcttaatgg tagaaacttc cttggtttca tgattaaagt cttttttttt cctga | | 995 |

<210> SEQ ID NO 6
<211> LENGTH: 184
<212> TYPE: PRT
<213> ORGANISM: homo sapiens

<400> SEQUENCE: 6

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Ser Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

```
Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Leu Ser Ala Thr Glu
                165                 170                 175

Ile Glu Lys Ser Ile Ser Ala Arg
            180

<210> SEQ ID NO 7
<211> LENGTH: 1149
<212> TYPE: DNA
<213> ORGANISM: homo sapiens
<220> FEATURE:
<221> NAME/KEY: CDS
<222> LOCATION: (173)...(1023)

<400> SEQUENCE: 7
gaattcggca cgaggcagaa aggagaaaat tcaggataac tctcctgagg ggtgagccaa      60
gccctgccat gtagtgcacg caggacatca acaaacacag ataacaggaa atgatccatt     120
ccctgtggtc acttattcta aaggccccaa ccttcaaagt tcaagtagtg at atg gat    178
                                                         Met Asp
                                                           1 gac tcc aca gaa agg gag cag tca cgc ctt act tct tgc ctt aag aaa      226
Asp Ser Thr Glu Arg Glu Gln Ser Arg Leu Thr Ser Cys Leu Lys Lys
      5                  10                  15 aga gaa gaa atg aaa ctg aag gag tgt gtt tcc atc ctc cca cgg aag      274
Arg Glu Glu Met Lys Leu Lys Glu Cys Val Ser Ile Leu Pro Arg Lys
 20                  25                  30 gaa agc ccc tct gtc cga tcc tcc aaa gac gga aag ctg ctg gct gca      322
Glu Ser Pro Ser Val Arg Ser Ser Lys Asp Gly Lys Leu Leu Ala Ala
 35                  40                  45                  50 acc ttg ctg ctg gca ctg ctg tct tgc tgc ctc acg gtg gtg tct ttc      370
Thr Leu Leu Leu Ala Leu Leu Ser Cys Cys Leu Thr Val Val Ser Phe
                 55                  60                  65 tac cag gtg gcc gcc ctg caa ggg gac ctg gcc agc ctc cgg gca gag      418
Tyr Gln Val Ala Ala Leu Gln Gly Asp Leu Ala Ser Leu Arg Ala Glu
             70                  75                  80 ctg cag ggc cac cac gcg gag aag ctg cca gca gga gca gga gcc ccc      466
Leu Gln Gly His His Ala Glu Lys Leu Pro Ala Gly Ala Gly Ala Pro
         85                  90                  95 aag gcc ggc ctg gag gaa gct cca gct gtc acc gcg gga ctg aaa atc      514
Lys Ala Gly Leu Glu Glu Ala Pro Ala Val Thr Ala Gly Leu Lys Ile
100                 105                 110 ttt gaa cca cca gct cca gga gaa ggc aac tcc agt cag aac agc aga      562
Phe Glu Pro Pro Ala Pro Gly Glu Gly Asn Ser Ser Gln Asn Ser Arg
115                 120                 125                 130 aat aag cgt gcc gtt cag ggt cca gaa gaa aca gtc act caa gac tgc      610
Asn Lys Arg Ala Val Gln Gly Pro Glu Glu Thr Val Thr Gln Asp Cys
                135                 140                 145 ttg caa ctg att gca gac agt gaa aca cca act ata caa aaa gga tct      658
Leu Gln Leu Ile Ala Asp Ser Glu Thr Pro Thr Ile Gln Lys Gly Ser
            150                 155                 160 tac aca ttt gtt cca tgg ctt ctc agc ttt aaa agg gga agt gcc cta      706
Tyr Thr Phe Val Pro Trp Leu Leu Ser Phe Lys Arg Gly Ser Ala Leu
        165                 170                 175 gaa gaa aaa gag aat aaa ata ttg gtc aaa gaa act ggt tac ttt ttt      754
Glu Glu Lys Glu Asn Lys Ile Leu Val Lys Glu Thr Gly Tyr Phe Phe
    180                 185                 190 ata tat ggt cag gtt tta tat act gat aag acc tac gcc atg gga cat      802
Ile Tyr Gly Gln Val Leu Tyr Thr Asp Lys Thr Tyr Ala Met Gly His
```

```
            195                 200                 205                 210
cta att cag agg aag aag gtc cat gtc ttt ggg gat gaa ttg agt ctg        850
Leu Ile Gln Arg Lys Lys Val His Val Phe Gly Asp Glu Leu Ser Leu
                    215                 220                 225 gtg act ttg ttt cga tgt att caa aat atg cct gaa aca cta ccc aat        898
Val Thr Leu Phe Arg Cys Ile Gln Asn Met Pro Glu Thr Leu Pro Asn
            230                 235                 240 aat tcc tgc tat tca gct ggc att gca aaa ctg gaa gaa gga gat gaa        946
Asn Ser Cys Tyr Ser Ala Gly Ile Ala Lys Leu Glu Glu Gly Asp Glu
            245                 250                 255 ctc caa ctt gca ata cca aga gaa aat gca caa ata tca ctg gat gga        994
Leu Gln Leu Ala Ile Pro Arg Glu Asn Ala Gln Ile Ser Leu Asp Gly
            260                 265                 270 gat gtc aca ttt ttt ggt gca ttg aaa ct gctgtgacct acttacacca          1043
Asp Val Thr Phe Phe Gly Ala Leu Lys
275                 280 tgtctgtagc tattttcctc cctttctctg tacctctaag aagaaagaat ctaactgaaa     1103
ataccaaaaa aaaaaaaaaa aaaaaaaaaa ccctcgagcg gccgcc                    1149
```

<210> SEQ ID NO 8
<211> LENGTH: 283
<212> TYPE: PRT
<213> ORGANISM: homo sapiens

<400> SEQUENCE: 8

```
Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
                20                  25                  30

Arg Lys Glu Ser Pro Ser Val Arg Ser Ser Lys Asp Gly Lys Leu Leu
            35                  40                  45

Ala Ala Thr Leu Leu Leu Ala Leu Leu Ser Cys Cys Leu Thr Val Val
        50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
210                 215                 220

Ser Leu Val Thr Leu Phe Arg Cys Ile Gln Asn Met Pro Glu Thr Leu
225                 230                 235                 240
```

```
Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys
        275                 280

<210> SEQ ID NO 9
<211> LENGTH: 1680
<212> TYPE: DNA
<213> ORGANISM: mus musculus
<220> FEATURE:
<221> NAME/KEY: CDS
<222> LOCATION: (164)...(1093)

<400> SEQUENCE: 9
tactcactat agggctcgag cggccgcccg ggcaggtgct cctgggggaa cccagccctg      60
ccatgctctg agggcagtct cccaggacac agatgacagg aaatgaccca ccctgtggt     120 cacttactcc aaaggcctag accttcaaag tgctcctcgt gga atg gat gag tct     175
                                              Met Asp Glu Ser
                                                1 gca aag acc ctg cca cca ccg tgc ctc tgt ttt tgc tcc gag aaa gga     223
Ala Lys Thr Leu Pro Pro Pro Cys Leu Cys Phe Cys Ser Glu Lys Gly
  5                  10                  15                  20 gaa gat atg aaa gtg gga tat gat ccc atc act ccg cag aag gag gag     271
Glu Asp Met Lys Val Gly Tyr Asp Pro Ile Thr Pro Gln Lys Glu Glu
                 25                  30                  35 ggt gcc tgg ttt ggg atc tgc agg gat gga agg ctg ctg gct gct acc     319
Gly Ala Trp Phe Gly Ile Cys Arg Asp Gly Arg Leu Leu Ala Ala Thr
             40                  45                  50 ctc ctg ctg gcc ctg ttg tcc agc agt ttc aca gcg atg tcc ttg tac     367
Leu Leu Leu Ala Leu Leu Ser Ser Ser Phe Thr Ala Met Ser Leu Tyr
         55                  60                  65 cag ttg gct gcc ttg caa gca gac ctg atg aac ctg cgc atg gag ctg     415
Gln Leu Ala Ala Leu Gln Ala Asp Leu Met Asn Leu Arg Met Glu Leu
     70                  75                  80 cag agc tac cga ggt tca gca aca cca gcc gcc gcg ggt gct cca gag     463
Gln Ser Tyr Arg Gly Ser Ala Thr Pro Ala Ala Ala Gly Ala Pro Glu
 85                  90                  95                 100 ttg acc gct gga gtc aaa ctc ctg aca ccg gca gct cct cga ccc cac     511
Leu Thr Ala Gly Val Lys Leu Leu Thr Pro Ala Ala Pro Arg Pro His
                105                 110                 115 aac tcc agc cgc ggc cac agg aac aga cgc gct ttc cag gga cca gag     559
Asn Ser Ser Arg Gly His Arg Asn Arg Arg Ala Phe Gln Gly Pro Glu
            120                 125                 130 gaa aca gaa caa gat gta gac ctc tca gct cct cct gca cca tgc ctg     607
Glu Thr Glu Gln Asp Val Asp Leu Ser Ala Pro Pro Ala Pro Cys Leu
        135                 140                 145 cct gga tgc cgc cat tct caa cat gat gat aat gga atg aac ctc aga     655
Pro Gly Cys Arg His Ser Gln His Asp Asp Asn Gly Met Asn Leu Arg
    150                 155                 160 aac atc att caa gac tgt ctg cag ctg att gca gac agc gac acg ccg     703
Asn Ile Ile Gln Asp Cys Leu Gln Leu Ile Ala Asp Ser Asp Thr Pro
165                 170                 175                 180 act ata cga aaa gga act tac aca ttt gtt cca tgg ctt ctc agc ttt     751
Thr Ile Arg Lys Gly Thr Tyr Thr Phe Val Pro Trp Leu Leu Ser Phe
                185                 190                 195 aaa aga gga aat gcc ttg gag gag aaa gag aac aaa ata gtg gtg agg     799
Lys Arg Gly Asn Ala Leu Glu Glu Lys Glu Asn Lys Ile Val Val Arg
            200                 205                 210
```

-continued

```
caa aca ggc tat ttc ttc atc tac agc cag gtt cta tac acg gac ccc      847
Gln Thr Gly Tyr Phe Phe Ile Tyr Ser Gln Val Leu Tyr Thr Asp Pro
        215                 220                 225 atc ttt gct atg ggt cat gtc atc cag agg aag aaa gta cac gtc ttt      895
Ile Phe Ala Met Gly His Val Ile Gln Arg Lys Lys Val His Val Phe
    230                 235                 240 ggg gac gag ctg agc ctg gtg acc ctg ttc cga tgt att cag aat atg      943
Gly Asp Glu Leu Ser Leu Val Thr Leu Phe Arg Cys Ile Gln Asn Met
245                 250                 255                 260 ccc aaa aca ctg ccc aac aat tcc tgc tac tcg gct ggc atc gcg agg      991
Pro Lys Thr Leu Pro Asn Asn Ser Cys Tyr Ser Ala Gly Ile Ala Arg
                265                 270                 275 ctg gaa gaa gga gat gag att cag ctt gca att cct cgg gag aat gca     1039
Leu Glu Glu Gly Asp Glu Ile Gln Leu Ala Ile Pro Arg Glu Asn Ala
            280                 285                 290 cag att tca cgc aac gga gac gac acc ttc ttt ggt gcc cta aaa ctg     1087
Gln Ile Ser Arg Asn Gly Asp Asp Thr Phe Phe Gly Ala Leu Lys Leu
        295                 300                 305 ctg taa ctcacttgct ggagtgcgtg atcccttcc ctcgtcttct ctgtacctcc       1143
Leu * gagggagaaa cagacgactg gaaaaactaa aagatgggga aagccgtcag cgaaagtttt   1203
ctcgtgaccc gttgaatctg atccaaacca ggaaatataa cagacagcca caaccgaagt   1263
gtgccatgtg agttatgaga acggagccc gcgctcagaa agaccggatg aggaagaccg    1323
ttttctccag tcctttgcca acacgcaccg caaccttgct ttttgccttg ggtgacacat   1383
gttcagaatg cagggagatt tccttgtttt gcgatttgcc atgagaagag gcccacaac    1443 tgcaggtcac tgaagcattc acgctaagtc tcaggattta ctctcccttc tcatgctaag   1503
tacacacacg ctctttttcca ggtaatacta tgggatacta tggaaaggtt gtttgttttt  1563
aaatctagaa gtcttgaact ggcaatagac aaaaatcctt ataaattcaa gtgtaaaata   1623
aacttaatta aaaaggtaaa aaaaaaaaa aaaaaaaaaa aaaaaaaaaa aaaaaaa       1680

<210> SEQ ID NO 10
<211> LENGTH: 309
<212> TYPE: PRT
<213> ORGANISM: mus musculus

<400> SEQUENCE: 10

Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Leu Ala Leu Leu Ser Ser Ser Phe Thr Ala
    50                  55                  60

Met Ser Leu Tyr Gln Leu Ala Ala Leu Gln Ala Asp Leu Met Asn Leu
65                  70                  75                  80

Arg Met Glu Leu Gln Ser Tyr Arg Gly Ser Ala Thr Pro Ala Ala Ala
                85                  90                  95

Gly Ala Pro Glu Leu Thr Ala Gly Val Lys Leu Leu Thr Pro Ala Ala
            100                 105                 110

Pro Arg Pro His Asn Ser Ser Arg Gly His Arg Asn Arg Arg Ala Phe
        115                 120                 125

Gln Gly Pro Glu Glu Thr Glu Gln Asp Val Asp Leu Ser Ala Pro Pro
```

```
            130                 135                 140
Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
                165                 170                 175

Ser Asp Thr Pro Thr Ile Arg Lys Gly Thr Tyr Thr Phe Val Pro Trp
            180                 185                 190

Leu Leu Ser Phe Lys Arg Gly Asn Ala Leu Glu Glu Lys Glu Asn Lys
        195                 200                 205

Ile Val Val Arg Gln Thr Gly Tyr Phe Phe Ile Tyr Ser Gln Val Leu
    210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
                245                 250                 255

Ile Gln Asn Met Pro Lys Thr Leu Pro Asn Asn Ser Cys Tyr Ser Ala
                260                 265                 270

Gly Ile Ala Arg Leu Glu Glu Gly Asp Glu Ile Gln Leu Ala Ile Pro
            275                 280                 285

Arg Glu Asn Ala Gln Ile Ser Arg Asn Gly Asp Asp Thr Phe Phe Gly
        290                 295                 300

Ala Leu Lys Leu Leu
305

<210> SEQ ID NO 11
<211> LENGTH: 185
<212> TYPE: PRT
<213> ORGANISM: homo sapiens

<400> SEQUENCE: 11

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
                20                  25                  30

Val Ala Cys Gly Leu Leu Arg Thr Pro Arg Pro Lys Pro Ala Gly Ala
            35                  40                  45

Ala Ser Ser Pro Ala Pro Arg Thr Ala Leu Gln Pro Gln Glu Ser Val
50                  55                  60

Gly Ala Gly Ala Gly Glu Ala Ala Leu Pro Leu Pro Gly Leu Leu Phe
65                  70                  75                  80

Gly Ala Pro Ala Leu Leu Gly Leu Ala Leu Val Leu Ala Leu Val Leu
                85                  90                  95

Val Gly Leu Val Ser Trp Arg Arg Arg Gln Arg Arg Leu Arg Gly Ala
            100                 105                 110

Ser Ser Ala Glu Ala Pro Asp Gly Asp Lys Asp Ala Pro Glu Pro Leu
        115                 120                 125

Asp Lys Val Ile Ile Leu Ser Pro Gly Ile Ser Asp Ala Thr Ala Pro
    130                 135                 140

Ala Trp Pro Pro Pro Gly Glu Asp Pro Gly Thr Thr Pro Pro Gly His
145                 150                 155                 160

Ser Val Pro Val Pro Ala Thr Glu Leu Gly Ser Thr Glu Leu Val Thr
                165                 170                 175

Thr Lys Thr Ala Gly Pro Glu Gln Gln
            180                 185
```

<210> SEQ ID NO 12
<211> LENGTH: 247
<212> TYPE: PRT
<213> ORGANISM: homo sapiens

<400> SEQUENCE: 12

Met Ser Gly Leu Gly Arg Ser Arg Arg Gly Gly Arg Ser Arg Val Asp
1               5                   10                  15

Gln Glu Glu Arg Trp Ser Leu Ser Cys Arg Lys Glu Gln Gly Lys Phe
            20                  25                  30

Tyr Asp His Leu Leu Arg Asp Cys Ile Ser Cys Ala Ser Ile Cys Gly
        35                  40                  45

Gln His Pro Lys Gln Cys Ala Tyr Phe Cys Glu Asn Lys Leu Arg Ser
    50                  55                  60

Pro Val Asn Leu Pro Pro Glu Leu Arg Arg Gln Arg Ser Gly Glu Val
65                  70                  75                  80

Glu Asn Asn Ser Asp Asn Ser Gly Arg Tyr Gln Gly Leu Glu His Arg
                85                  90                  95

Gly Ser Glu Ala Ser Pro Ala Leu Pro Gly Leu Lys Leu Ser Ala Asp
            100                 105                 110

Gln Val Ala Leu Val Tyr Ser Thr Leu Gly Leu Cys Leu Cys Ala Val
        115                 120                 125

Leu Cys Cys Phe Leu Val Ala Val Ala Cys Phe Leu Lys Lys Arg Gly
    130                 135                 140

Asp Pro Cys Ser Cys Gln Pro Arg Ser Arg Pro Arg Gln Ser Pro Ala
145                 150                 155                 160

Lys Ser Ser Gln Asp His Ala Met Glu Ala Gly Ser Pro Val Ser Thr
                165                 170                 175

Ser Pro Glu Pro Val Glu Thr Cys Ser Phe Cys Phe Pro Glu Cys Arg
            180                 185                 190

Ala Pro Thr Gln Glu Ser Ala Val Thr Pro Gly Thr Pro Asp Pro Thr
        195                 200                 205

Cys Ala Gly Arg Trp Gly Cys His Thr Arg Thr Thr Val Leu Gln Pro
210                 215                 220

Cys Pro His Ile Pro Asp Ser Gly Leu Gly Ile Val Cys Val Pro Ala
225                 230                 235                 240

Gln Glu Gly Gly Pro Gly Ala
                245

<210> SEQ ID NO 13
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 13

Glu Cys Phe Asp Leu Leu Val Arg Ala Trp Val Pro Cys Ser Val Leu
1               5                   10                  15

Lys

<210> SEQ ID NO 14
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 14

Glu Cys Phe Asp Leu Leu Val Arg His Trp Val Pro Cys Gly Leu Leu
1               5                   10                  15

Arg

<210> SEQ ID NO 15
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 15

Glu Cys Phe Asp Leu Leu Val Arg Arg Trp Val Pro Cys Glu Met Leu
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 16

Glu Cys Phe Asp Leu Leu Val Arg Ser Trp Val Pro Cys His Met Leu
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: BLyS binding polypeptide

<400> SEQUENCE: 17

Glu Cys Phe Asp Leu Leu Val Arg His Trp Val Ala Cys Gly Leu Leu
1               5                   10                  15

Arg

<210> SEQ ID NO 18
<211> LENGTH: 1214
<212> TYPE: DNA
<213> ORGANISM: Artificial Sequence
<220> FEATURE:
<223> OTHER INFORMATION: TACI-Fc fusion protein
<221> NAME/KEY: CDS
<222> LOCATION: (17)...(1192)

<400> SEQUENCE: 18

```
tattaggccg gccacc atg gat gca atg aag aga ggg ctc tgc tgt gtg ctg        52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc         100
Leu Leu Cys Gly Ala Val Phe Val Ser Leu Ser Gln Glu Ile His Ala
        15                  20                  25 gag ttg aga cgc ttc cgt aga gct atg aga tcc tgc ccc gaa gag cag         148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc         196
Tyr Trp Asp Pro Leu Leu Gly Thr Cys Met Ser Cys Lys Thr Ile Cys
 45                  50                  55                  60
```

| | | |
|---|---|---|
| aac cat cag agc cag cgc acc tgt gca gcc ttc tgc agg tca ctc agc<br>Asn His Gln Ser Gln Arg Thr Cys Ala Ala Phe Cys Arg Ser Leu Ser<br>                 65                    70                  75 | 244 | |
| tgc cgc aag gag caa ggc aag ttc tat gac cat ctc ctg agg gac tgc<br>Cys Arg Lys Glu Gln Gly Lys Phe Tyr Asp His Leu Leu Arg Asp Cys<br>80                     85                   90 | 292 | |
| atc agc tgt gcc tcc atc tgt gga cag cac cct aag caa tgt gca tac<br>Ile Ser Cys Ala Ser Ile Cys Gly Gln His Pro Lys Gln Cys Ala Tyr<br>       95                 100                105 | 340 | |
| ttc tgt gag aac aag ctc agg agc cca gtg aac ctt cca cca gag ctc<br>Phe Cys Glu Asn Lys Leu Arg Ser Pro Val Asn Leu Pro Pro Glu Leu<br>110                  115               120 | 388 | |
| agg aga cag cgg agt gga gaa gtt gaa aac aat tca gac aac tcg gga<br>Arg Arg Gln Arg Ser Gly Glu Val Glu Asn Asn Ser Asp Asn Ser Gly<br>125                130               135              140 | 436 | |
| agg tac caa gga ttg gag cac aga ggc tca gaa gca agt cca gct ctc<br>Arg Tyr Gln Gly Leu Glu His Arg Gly Ser Glu Ala Ser Pro Ala Leu<br>               145               150              155 | 484 | |
| cca ggt ctc aag gag ccc aaa tct tca gac aaa act cac aca tgc cca<br>Pro Gly Leu Lys Glu Pro Lys Ser Ser Asp Lys Thr His Thr Cys Pro<br>           160                   165              170 | 532 | |
| ccg tgc cca gca cct gaa gcc gag ggg gca ccg tca gtc ttc ctc ttc<br>Pro Cys Pro Ala Pro Glu Ala Glu Gly Ala Pro Ser Val Phe Leu Phe<br>175                  180               185 | 580 | |
| ccc cca aaa ccc aag gac acc ctc atg atc tcc cgg acc cct gag gtc<br>Pro Pro Lys Pro Lys Asp Thr Leu Met Ile Ser Arg Thr Pro Glu Val<br>      190                 195                200 | 628 | |
| aca tgc gtg gtg gtg gac gtg agc cac gaa gac cct gag gtc aag ttc<br>Thr Cys Val Val Val Asp Val Ser His Glu Asp Pro Glu Val Lys Phe<br>205                  210               215              220 | 676 | |
| aac tgg tac gtg gac ggc gtg gag gtg cat aat gcc aag aca aag ccg<br>Asn Trp Tyr Val Asp Gly Val Glu Val His Asn Ala Lys Thr Lys Pro<br>               225               230              235 | 724 | |
| cgg gag gag cag tac aac agc acg tac cgt gtg gtc agc gtc ctc acc<br>Arg Glu Glu Gln Tyr Asn Ser Thr Tyr Arg Val Val Ser Val Leu Thr<br>          240                   245              250 | 772 | |
| gtc ctg cac cag gac tgg ctg aat ggc aag gag tac aag tgc aag gtc<br>Val Leu His Gln Asp Trp Leu Asn Gly Lys Glu Tyr Lys Cys Lys Val<br>               255               260              265 | 820 | |
| tcc aac aaa gcc ctc cca tcc tcc atc gag aaa acc atc tcc aaa gcc<br>Ser Asn Lys Ala Leu Pro Ser Ser Ile Glu Lys Thr Ile Ser Lys Ala<br>          270                   275              280 | 868 | |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>285                  290               295              300 | 916 | |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>               305               310              315 | 964 | |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>                  320               325              330 | 1012 | |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>335                  340               345 | 1060 | |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>      350                 355                360 | 1108 | |
| ggg aac gtc ttc tca tgc tcc gtg atg cat gag gct ctg cac aac cac<br>Gly Asn Val Phe Ser Cys Ser Val Met His Glu Ala Leu His Asn His | 1156 | |

```
                  365                 370                 375                 380
tac acg cag aag agc ctc tcc ctg tct ccg ggt aaa taatctagag                       1202
Tyr Thr Gln Lys Ser Leu Ser Leu Ser Pro Gly Lys
                385                 390 gcgcgccaat ta                                                                   1214

<210> SEQ ID NO 19
<211> LENGTH: 392
<212> TYPE: PRT
<213> ORGANISM: Artificial Sequence
<220> FEATURE:
<223> OTHER INFORMATION: TACI-Fc fusion protein

<400> SEQUENCE: 19

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Lys Leu Arg Ser Pro Val Asn Leu Pro Pro Glu Leu Arg Arg Gln Arg
        115                 120                 125

Ser Gly Glu Val Glu Asn Asn Ser Asp Asn Ser Gly Arg Tyr Gln Gly
    130                 135                 140

Leu Glu His Arg Gly Ser Glu Ala Ser Pro Ala Leu Pro Gly Leu Lys
145                 150                 155                 160

Glu Pro Lys Ser Ser Asp Lys Thr His Thr Cys Pro Pro Cys Pro Ala
                165                 170                 175

Pro Glu Ala Glu Gly Ala Pro Ser Val Phe Leu Phe Pro Pro Lys Pro
            180                 185                 190

Lys Asp Thr Leu Met Ile Ser Arg Thr Pro Glu Val Thr Cys Val Val
        195                 200                 205

Val Asp Val Ser His Glu Asp Pro Glu Val Lys Phe Asn Trp Tyr Val
    210                 215                 220

Asp Gly Val Glu Val His Asn Ala Lys Thr Lys Pro Arg Glu Glu Gln
225                 230                 235                 240

Tyr Asn Ser Thr Tyr Arg Val Val Ser Val Leu Thr Val Leu His Gln
                245                 250                 255

Asp Trp Leu Asn Gly Lys Glu Tyr Lys Cys Lys Val Ser Asn Lys Ala
            260                 265                 270

Leu Pro Ser Ser Ile Glu Lys Thr Ile Ser Lys Ala Lys Gly Gln Pro
        275                 280                 285

Arg Glu Pro Gln Val Tyr Thr Leu Pro Pro Ser Arg Asp Glu Leu Thr
    290                 295                 300

Lys Asn Gln Val Ser Leu Thr Cys Leu Val Lys Gly Phe Tyr Pro Ser
305                 310                 315                 320

Asp Ile Ala Val Glu Trp Glu Ser Asn Gly Gln Pro Glu Asn Asn Tyr
```

```
                         325                 330                 335
        Lys Thr Thr Pro Pro Val Leu Asp Ser Asp Gly Ser Phe Phe Leu Tyr
                     340                 345                 350

Ser Lys Leu Thr Val Asp Lys Ser Arg Trp Gln Gln Gly Asn Val Phe
                     355                 360                 365

Ser Cys Ser Val Met His Glu Ala Leu His Asn His Tyr Thr Gln Lys
                 370                 375                 380

Ser Leu Ser Leu Ser Pro Gly Lys
        385                 390

<210> SEQ ID NO 20
<211> LENGTH: 1070
<212> TYPE: DNA
<213> ORGANISM: Artificial Sequence
<220> FEATURE:
<223> OTHER INFORMATION: TACI-Fc fusion protein
<221> NAME/KEY: CDS
<222> LOCATION: (17)...(1048)

<400> SEQUENCE: 20
tattaggccg gccacc atg gat gca atg aag aga ggg ctc tgc tgt gtg ctg      52
                  Met Asp Ala Met Lys Arg Gly Leu Cys Cys Val Leu
                  1               5                  10 ctg ctg tgt ggc gcc gtc ttc gtt tcg ctc agc cag gaa atc cat gcc       100
Leu Leu Cys Gly Ala Val Phe Val Ser Leu Ser Gln Glu Ile His Ala
            15                  20                  25 gag ttg aga cgc ttc cgt aga gct atg aga tcc tgc ccc gaa gag cag       148
Glu Leu Arg Arg Phe Arg Arg Ala Met Arg Ser Cys Pro Glu Glu Gln
        30                  35                  40 tac tgg gat cct ctg ctg ggt acc tgc atg tcc tgc aaa acc att tgc       196
Tyr Trp Asp Pro Leu Leu Gly Thr Cys Met Ser Cys Lys Thr Ile Cys
 45                  50                  55                  60 aac cat cag agc cag cgc acc tgt gca gcc ttc tgc agg tca ctc agc       244
Asn His Gln Ser Gln Arg Thr Cys Ala Ala Phe Cys Arg Ser Leu Ser
                 65                  70                  75 tgc cgc aag gag caa ggc aag ttc tat gac cat ctc ctg agg gac tgc       292
Cys Arg Lys Glu Gln Gly Lys Phe Tyr Asp His Leu Leu Arg Asp Cys
             80                  85                  90 atc agc tgt gcc tcc atc tgt gga cag cac cct aag caa tgt gca tac       340
Ile Ser Cys Ala Ser Ile Cys Gly Gln His Pro Lys Gln Cys Ala Tyr
         95                 100                 105 ttc tgt gag aac gag ccc aaa tct tca gac aaa act cac aca tgc cca       388
Phe Cys Glu Asn Glu Pro Lys Ser Ser Asp Lys Thr His Thr Cys Pro
    110                 115                 120 ccg tgc cca gca cct gaa gcc gag ggg gca ccg tca gtc ttc ctc ttc       436
Pro Cys Pro Ala Pro Glu Ala Glu Gly Ala Pro Ser Val Phe Leu Phe
125                 130                 135                 140 ccc cca aaa ccc aag gac acc ctc atg atc tcc cgg acc cct gag gtc       484
Pro Pro Lys Pro Lys Asp Thr Leu Met Ile Ser Arg Thr Pro Glu Val
                145                 150                 155 aca tgc gtg gtg gtg gac gtg agc cac gaa gac cct gag gtc aag ttc       532
Thr Cys Val Val Val Asp Val Ser His Glu Asp Pro Glu Val Lys Phe
            160                 165                 170 aac tgg tac gtg gac ggc gtg gag gtg cat aat gcc aag aca aag ccg       580
Asn Trp Tyr Val Asp Gly Val Glu Val His Asn Ala Lys Thr Lys Pro
        175                 180                 185 cgg gag gag cag tac aac agc acg tac cgt gtg gtc agc gtc ctc acc       628
Arg Glu Glu Gln Tyr Asn Ser Thr Tyr Arg Val Val Ser Val Leu Thr
    190                 195                 200 gtc ctg cac cag gac tgg ctg aat ggc aag gag tac aag tgc aag gtc       676
```

| | | |
|---|---|---|
| Val Leu His Gln Asp Trp Leu Asn Gly Lys Glu Tyr Lys Cys Lys Val<br>205 210 215 220 | | |
| tcc aac aaa gcc ctc cca tcc tcc atc gag aaa acc atc tcc aaa gcc<br>Ser Asn Lys Ala Leu Pro Ser Ser Ile Glu Lys Thr Ile Ser Lys Ala<br>225 230 235 | | 724 |
| aaa ggg cag ccc cga gaa cca cag gtg tac acc ctg ccc cca tcc cgg<br>Lys Gly Gln Pro Arg Glu Pro Gln Val Tyr Thr Leu Pro Pro Ser Arg<br>240 245 250 | | 772 |
| gat gag ctg acc aag aac cag gtc agc ctg acc tgc ctg gtc aaa ggc<br>Asp Glu Leu Thr Lys Asn Gln Val Ser Leu Thr Cys Leu Val Lys Gly<br>255 260 265 | | 820 |
| ttc tat ccc agc gac atc gcc gtg gag tgg gag agc aat ggg cag ccg<br>Phe Tyr Pro Ser Asp Ile Ala Val Glu Trp Glu Ser Asn Gly Gln Pro<br>270 275 280 | | 868 |
| gag aac aac tac aag acc acg cct ccc gtg ctg gac tcc gac ggc tcc<br>Glu Asn Asn Tyr Lys Thr Thr Pro Pro Val Leu Asp Ser Asp Gly Ser<br>285 290 295 300 | | 916 |
| ttc ttc ctc tac agc aag ctc acc gtg gac aag agc agg tgg cag cag<br>Phe Phe Leu Tyr Ser Lys Leu Thr Val Asp Lys Ser Arg Trp Gln Gln<br>305 310 315 | | 964 |
| ggg aac gtc ttc tca tgc tcc gtg atg cat gag gct ctg cac aac cac<br>Gly Asn Val Phe Ser Cys Ser Val Met His Glu Ala Leu His Asn His<br>320 325 330 | | 1012 |
| tac acg cag aag agc ctc tcc ctg tct ccg ggt aaa taatctagag<br>Tyr Thr Gln Lys Ser Leu Ser Leu Ser Pro Gly Lys<br>335 340 | | 1058 |
| gcgcgccaat ta | | 1070 |

<210> SEQ ID NO 21
<211> LENGTH: 344
<212> TYPE: PRT
<213> ORGANISM: Artificial Sequence
<220> FEATURE:
<223> OTHER INFORMATION: TACI-Fc fusion protein

<400> SEQUENCE: 21

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60

Gln Arg Thr Cys Ala Ala Phe Cys Arg Ser Leu Ser Cys Arg Lys Glu
65                  70                  75                  80

Gln Gly Lys Phe Tyr Asp His Leu Leu Arg Asp Cys Ile Ser Cys Ala
                85                  90                  95

Ser Ile Cys Gly Gln His Pro Lys Gln Cys Ala Tyr Phe Cys Glu Asn
            100                 105                 110

Glu Pro Lys Ser Ser Asp Lys Thr His Thr Cys Pro Pro Cys Pro Ala
        115                 120                 125

Pro Glu Ala Glu Gly Ala Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

```
Asp Gly Val Glu Val His Asn Ala Lys Thr Lys Pro Arg Glu Glu Gln
            180                 185                 190

Tyr Asn Ser Thr Tyr Arg Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ser Ser Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 22
<211> LENGTH: 1082
<212> TYPE: DNA
<213> ORGANISM: Artificial Sequence
<220> FEATURE:
<223> OTHER INFORMATION: TACI-Fc fusion protein
<221> NAME/KEY: CDS
<222> LOCATION: (17)...(1060)

<400> SEQUENCE: 22
tattaggccg gccacc atg gat gca atg aag aga ggg ctc tgc tgt gtg ctg     52
                Met Asp Ala Met Lys Arg Gly Leu Cys Cys Val Leu
                 1               5                  10 ctg ctg tgt ggc gcc gtc ttc gtt tcg ctc agc cag gaa atc cat gcc    100
Leu Leu Cys Gly Ala Val Phe Val Ser Leu Ser Gln Glu Ile His Ala
        15                  20                  25 gag ttg aga cgc ttc cgt aga gct atg aga tcc tgc ccc gaa gag cag    148
Glu Leu Arg Arg Phe Arg Arg Ala Met Arg Ser Cys Pro Glu Glu Gln
    30                  35                  40 tac tgg gat cct ctg ctg ggt acc tgc atg tcc tgc aaa acc att tgc    196
Tyr Trp Asp Pro Leu Leu Gly Thr Cys Met Ser Cys Lys Thr Ile Cys
45                  50                  55                  60 aac cat cag agc cag cgc acc tgt gca gcc ttc tgc agg tca ctc agc    244
Asn His Gln Ser Gln Arg Thr Cys Ala Ala Phe Cys Arg Ser Leu Ser
                65                  70                  75 tgc cgc aag gag caa ggc aag ttc tat gac cat ctc ctg agg gac tgc    292
Cys Arg Lys Glu Gln Gly Lys Phe Tyr Asp His Leu Leu Arg Asp Cys
            80                  85                  90 atc agc tgt gcc tcc atc tgt gga cag cac cct aag caa tgt gca tac    340
Ile Ser Cys Ala Ser Ile Cys Gly Gln His Pro Lys Gln Cys Ala Tyr
        95                 100                 105 ttc tgt gag aac aag ctc agg agc gag ccc aaa tct tca gac aaa act    388
Phe Cys Glu Asn Lys Leu Arg Ser Glu Pro Lys Ser Ser Asp Lys Thr
    110                 115                 120 cac aca tgc cca ccg tgc cca gca cct gaa gcc gag ggg gca ccg tca    436
```

-continued

```
                His Thr Cys Pro Pro Cys Pro Ala Pro Glu Ala Gly Ala Pro Ser
                125                 130                 135                 140 gtc ttc ctc ttc ccc cca aaa ccc aag gac acc ctc atg atc tcc cgg             484
Val Phe Leu Phe Pro Pro Lys Pro Lys Asp Thr Leu Met Ile Ser Arg
                145                 150                 155 acc cct gag gtc aca tgc gtg gtg gtg gac gtg agc cac gaa gac cct             532
Thr Pro Glu Val Thr Cys Val Val Val Asp Val Ser His Glu Asp Pro
            160                 165                 170 gag gtc aag ttc aac tgg tac gtg gac ggc gtg gag gtg cat aat gcc             580
Glu Val Lys Phe Asn Trp Tyr Val Asp Gly Val Glu Val His Asn Ala
            175                 180                 185 aag aca aag ccg cgg gag gag cag tac aac agc acg tac cgt gtg gtc             628
Lys Thr Lys Pro Arg Glu Glu Gln Tyr Asn Ser Thr Tyr Arg Val Val
    190                 195                 200 agc gtc ctc acc gtc ctg cac cag gac tgg ctg aat ggc aag gag tac             676
Ser Val Leu Thr Val Leu His Gln Asp Trp Leu Asn Gly Lys Glu Tyr
205                 210                 215                 220 aag tgc aag gtc tcc aac aaa gcc ctc cca tcc tcc atc gag aaa acc             724
Lys Cys Lys Val Ser Asn Lys Ala Leu Pro Ser Ser Ile Glu Lys Thr
                225                 230                 235 atc tcc aaa gcc aaa ggg cag ccc cga gaa cca cag gtg tac acc ctg             772
Ile Ser Lys Ala Lys Gly Gln Pro Arg Glu Pro Gln Val Tyr Thr Leu
            240                 245                 250 ccc cca tcc cgg gat gag ctg acc aag aac cag gtc agc ctg acc tgc             820
Pro Pro Ser Arg Asp Glu Leu Thr Lys Asn Gln Val Ser Leu Thr Cys
            255                 260                 265 ctg gtc aaa ggc ttc tat ccc agc gac atc gcc gtg gag tgg gag agc             868
Leu Val Lys Gly Phe Tyr Pro Ser Asp Ile Ala Val Glu Trp Glu Ser
    270                 275                 280 aat ggg cag ccg gag aac aac tac aag acc acg cct ccc gtg ctg gac             916
Asn Gly Gln Pro Glu Asn Asn Tyr Lys Thr Thr Pro Pro Val Leu Asp
285                 290                 295                 300 tcc gac ggc tcc ttc ttc ctc tac agc aag ctc acc gtg gac aag agc             964
Ser Asp Gly Ser Phe Phe Leu Tyr Ser Lys Leu Thr Val Asp Lys Ser
                305                 310                 315 agg tgg cag cag ggg aac gtc ttc tca tgc tcc gtg atg cat gag gct             1012
Arg Trp Gln Gln Gly Asn Val Phe Ser Cys Ser Val Met His Glu Ala
            320                 325                 330 ctg cac aac cac tac acg cag aag agc ctc tcc ctg tct ccg ggt aaa             1060
Leu His Asn His Tyr Thr Gln Lys Ser Leu Ser Leu Ser Pro Gly Lys
            335                 340                 345 taatctagag gcgcgccaat ta                                                    1082
```

<210> SEQ ID NO 23
<211> LENGTH: 348
<212> TYPE: PRT
<213> ORGANISM: Artificial Sequence
<220> FEATURE:
<223> OTHER INFORMATION: TACI-Fc fusion protein

<400> SEQUENCE: 23

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Met Arg Ser Cys Pro Glu Glu Gln Tyr Trp Asp Pro
        35                  40                  45

Leu Leu Gly Thr Cys Met Ser Cys Lys Thr Ile Cys Asn His Gln Ser
    50                  55                  60
```

```
Gln Arg Thr Cys Ala Ala Phe Cys Arg Ser Leu Ser Cys Arg Lys Glu
 65                  70                  75                  80

Gln Gly Lys Phe Tyr Asp His Leu Leu Arg Asp Cys Ile Ser Cys Ala
                 85                  90                  95

Ser Ile Cys Gly Gln His Pro Lys Gln Cys Ala Tyr Phe Cys Glu Asn
            100                 105                 110

Lys Leu Arg Ser Glu Pro Lys Ser Ser Asp Lys Thr His Thr Cys Pro
        115                 120                 125

Pro Cys Pro Ala Pro Glu Ala Glu Gly Ala Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Asp Glu Leu Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys
            340                 345
```

<210> SEQ ID NO 24
<211> LENGTH: 1109
<212> TYPE: DNA
<213> ORGANISM: Artificial Sequence
<220> FEATURE:
<223> OTHER INFORMATION: TACI-Fc fusion protein
<221> NAME/KEY: CDS
<222> LOCATION: (17)...(1090)

<400> SEQUENCE: 24

```
tattaggccg gccacc atg gat gca atg aag aga ggg ctc tgc tgt gtg ctg        52
               Met Asp Ala Met Lys Arg Gly Leu Cys Cys Val Leu
                 1               5                  10 ctg ctg tgt ggc gcc gtc ttc gtt tcg ctc agc cag gaa atc cat gcc        100
Leu Leu Cys Gly Ala Val Phe Val Ser Leu Ser Gln Glu Ile His Ala
         15                  20                  25 gag ttg aga cgc ttc cgt aga gct atg aga tcc tgc ccc gaa gag cag        148
Glu Leu Arg Arg Phe Arg Arg Ala Met Arg Ser Cys Pro Glu Glu Gln
     30                  35                  40 tac tgg gat cct ctg ctg ggt acc tgc atg tcc tgc aaa acc att tgc        196
```

```
          Tyr Trp Asp Pro Leu Leu Gly Thr Cys Met Ser Cys Lys Thr Ile Cys
           45                  50                  55                  60 aac cat cag agc cag cgc acc tgt gca gcc ttc tgc agg tca ctc agc         244
Asn His Gln Ser Gln Arg Thr Cys Ala Ala Phe Cys Arg Ser Leu Ser
                     65                  70                  75 tgc cgc aag gag caa ggc aag ttc tat gac cat ctc ctg agg gac tgc         292
Cys Arg Lys Glu Gln Gly Lys Phe Tyr Asp His Leu Leu Arg Asp Cys
                 80                  85                  90 atc agc tgt gcc tcc atc tgt gga cag cac cct aag caa tgt gca tac         340
Ile Ser Cys Ala Ser Ile Cys Gly Gln His Pro Lys Gln Cys Ala Tyr
             95                 100                 105 ttc tgt gag aac aag ctc agg agc cca gtg aac ctt cca cca gag ctc         388
Phe Cys Glu Asn Lys Leu Arg Ser Pro Val Asn Leu Pro Pro Glu Leu
        110                 115                 120 agg gag ccc aaa tct tca gac aaa act cac aca tgc cca cgg tgc cca         436
Arg Glu Pro Lys Ser Ser Asp Lys Thr His Thr Cys Pro Pro Cys Pro
125                 130                 135                 140 gca cct gaa gcc gag ggg gca ccg tca gtc ttc ctc ttc ccc cca aaa         484
Ala Pro Glu Ala Glu Gly Ala Pro Ser Val Phe Leu Phe Pro Pro Lys
                145                 150                 155 ccc aag gac acc ctc atg atc tcc cgg acc cct gag gtc aca tgc gtg         532
Pro Lys Asp Thr Leu Met Ile Ser Arg Thr Pro Glu Val Thr Cys Val
            160                 165                 170 gtg gtg gac gtg agc cac gaa gac cct gag gtc aag ttc aac tgg tac         580
Val Val Asp Val Ser His Glu Asp Pro Glu Val Lys Phe Asn Trp Tyr
        175                 180                 185 gtg gac ggc gtg gag gtg cat aat gcc aag aca aag ccg cgg gag gag         628
Val Asp Gly Val Glu Val His Asn Ala Lys Thr Lys Pro Arg Glu Glu
190                 195                 200 cag tac aac agc acg tac cgt gtg gtc agc gtc ctc acc gtc ctg cac         676
Gln Tyr Asn Ser Thr Tyr Arg Val Val Ser Val Leu Thr Val Leu His
205                 210                 215                 220 cag gac tgg ctg aat ggc aag gag tac aag tgc aag gtc tcc aac aaa         724
Gln Asp Trp Leu Asn Gly Lys Glu Tyr Lys Cys Lys Val Ser Asn Lys
                225                 230                 235 gcc ctc cca tcc tcc atc gag aaa acc atc tcc aaa gcc aaa ggg cag         772
Ala Leu Pro Ser Ser Ile Glu Lys Thr Ile Ser Lys Ala Lys Gly Gln
            240                 245                 250 ccc cga gaa cca cag gtg tac acc ctg ccc cca tcc cgg gat gag ctg         820
Pro Arg Glu Pro Gln Val Tyr Thr Leu Pro Pro Ser Arg Asp Glu Leu
        255                 260                 265 acc aag aac cag gtc agc ctg acc tgc ctg gtc aaa ggc ttc tat ccc         868
Thr Lys Asn Gln Val Ser Leu Thr Cys Leu Val Lys Gly Phe Tyr Pro
270                 275                 280 agc gac atc gcc gtg gag tgg gag agc aat ggg cag ccg gag aac aac         916
Ser Asp Ile Ala Val Glu Trp Glu Ser Asn Gly Gln Pro Glu Asn Asn
285                 290                 295                 300 tac aag acc acg cct ccc gtg ctg gac tcc gac ggc tcc ttc ttc ctc         964
Tyr Lys Thr Thr Pro Pro Val Leu Asp Ser Asp Gly Ser Phe Phe Leu
                305                 310                 315 tac agc aag ctc acc gtg gac aag agc agg tgg cag cag ggg aac gtc        1012
Tyr Ser Lys Leu Thr Val Asp Lys Ser Arg Trp Gln Gln Gly Asn Val
            320                 325                 330 ttc tca tgc tcc gtg atg cat gag gct ctg cac aac cac tac acg cag        1060
Phe Ser Cys Ser Val Met His Glu Ala Leu His Asn His Tyr Thr Gln
        335                 340                 345 aag agc ctc tcc ctg tct ccg ggt aaa taa tctagaggcg cgccaatta           1109
Lys Ser Leu Ser Leu Ser Pro Gly Lys *
350                 355
```

```
<210> SEQ ID NO 25
<211> LENGTH: 357
<212> TYPE: PRT
<213> ORGANISM: Artificial Sequence
<220> FEATURE:
<223> OTHER INFORMATION: TACI-Fc fusion protein

<400> SEQUENCE: 25
```

| | | | | | | | | | | | | | | | |
|---|---|---|---|---|---|---|---|---|---|---|---|---|---|---|---|
| Met | Asp | Ala | Met | Lys | Arg | Gly | Leu | Cys | Cys | Val | Leu | Leu | Leu | Cys | Gly |
| 1 | | | | 5 | | | | | 10 | | | | | 15 | |
| Ala | Val | Phe | Val | Ser | Leu | Ser | Gln | Glu | Ile | His | Ala | Glu | Leu | Arg | Arg |
| | | | 20 | | | | | 25 | | | | | 30 | | |
| Phe | Arg | Arg | Ala | Met | Arg | Ser | Cys | Pro | Glu | Glu | Gln | Tyr | Trp | Asp | Pro |
| | | 35 | | | | | 40 | | | | | 45 | | | |
| Leu | Leu | Gly | Thr | Cys | Met | Ser | Cys | Lys | Thr | Ile | Cys | Asn | His | Gln | Ser |
| | 50 | | | | | 55 | | | | | 60 | | | | |
| Gln | Arg | Thr | Cys | Ala | Ala | Phe | Cys | Arg | Ser | Leu | Ser | Cys | Arg | Lys | Glu |
| 65 | | | | | 70 | | | | | 75 | | | | | 80 |
| Gln | Gly | Lys | Phe | Tyr | Asp | His | Leu | Leu | Arg | Asp | Cys | Ile | Ser | Cys | Ala |
| | | | | 85 | | | | | 90 | | | | | 95 | |
| Ser | Ile | Cys | Gly | Gln | His | Pro | Lys | Gln | Cys | Ala | Tyr | Phe | Cys | Glu | Asn |
| | | | 100 | | | | | 105 | | | | | 110 | | |
| Lys | Leu | Arg | Ser | Pro | Val | Asn | Leu | Pro | Pro | Glu | Leu | Arg | Glu | Pro | Lys |
| | | 115 | | | | | 120 | | | | | 125 | | | |
| Ser | Ser | Asp | Lys | Thr | His | Thr | Cys | Pro | Pro | Cys | Pro | Ala | Pro | Glu | Ala |
| | 130 | | | | | 135 | | | | | 140 | | | | |
| Glu | Gly | Ala | Pro | Ser | Val | Phe | Leu | Phe | Pro | Pro | Lys | Pro | Lys | Asp | Thr |
| 145 | | | | | 150 | | | | | 155 | | | | | 160 |
| Leu | Met | Ile | Ser | Arg | Thr | Pro | Glu | Val | Thr | Cys | Val | Val | Val | Asp | Val |
| | | | | 165 | | | | | 170 | | | | | 175 | |
| Ser | His | Glu | Asp | Pro | Glu | Val | Lys | Phe | Asn | Trp | Tyr | Val | Asp | Gly | Val |
| | | | 180 | | | | | 185 | | | | | 190 | | |
| Glu | Val | His | Asn | Ala | Lys | Thr | Lys | Pro | Arg | Glu | Glu | Gln | Tyr | Asn | Ser |
| | | 195 | | | | | 200 | | | | | 205 | | | |
| Thr | Tyr | Arg | Val | Val | Ser | Val | Leu | Thr | Val | Leu | His | Gln | Asp | Trp | Leu |
| | 210 | | | | | 215 | | | | | 220 | | | | |
| Asn | Gly | Lys | Glu | Tyr | Lys | Cys | Lys | Val | Ser | Asn | Lys | Ala | Leu | Pro | Ser |
| 225 | | | | | 230 | | | | | 235 | | | | | 240 |
| Ser | Ile | Glu | Lys | Thr | Ile | Ser | Lys | Ala | Lys | Gly | Gln | Pro | Arg | Glu | Pro |
| | | | | 245 | | | | | 250 | | | | | 255 | |
| Gln | Val | Tyr | Thr | Leu | Pro | Pro | Ser | Arg | Asp | Glu | Leu | Thr | Lys | Asn | Gln |
| | | | 260 | | | | | 265 | | | | | 270 | | |
| Val | Ser | Leu | Thr | Cys | Leu | Val | Lys | Gly | Phe | Tyr | Pro | Ser | Asp | Ile | Ala |
| | | 275 | | | | | 280 | | | | | 285 | | | |
| Val | Glu | Trp | Glu | Ser | Asn | Gly | Gln | Pro | Glu | Asn | Asn | Tyr | Lys | Thr | Thr |
| | 290 | | | | | 295 | | | | | 300 | | | | |
| Pro | Pro | Val | Leu | Asp | Ser | Asp | Gly | Ser | Phe | Phe | Leu | Tyr | Ser | Lys | Leu |
| 305 | | | | | 310 | | | | | 315 | | | | | 320 |
| Thr | Val | Asp | Lys | Ser | Arg | Trp | Gln | Gln | Gly | Asn | Val | Phe | Ser | Cys | Ser |
| | | | | 325 | | | | | 330 | | | | | 335 | |
| Val | Met | His | Glu | Ala | Leu | His | Asn | His | Tyr | Thr | Gln | Lys | Ser | Leu | Ser |
| | | | 340 | | | | | 345 | | | | | 350 | | |
| Leu | Ser | Pro | Gly | Lys | | | | | | | | | | | |
| | | | 355 | | | | | | | | | | | | |

<210> SEQ ID NO 26
<211> LENGTH: 311
<212> TYPE: PRT
<213> ORGANISM: Artificial Sequence
<220> FEATURE:
<223> OTHER INFORMATION: BAFF-R-Fc fusion protein

<400> SEQUENCE: 26

Met Ser Ala Leu Leu Ile Leu Ala Leu Val Gly Ala Ala Val Ala Ser
1               5                   10                  15

Thr Arg Arg Gly Pro Arg Ser Leu Arg Gly Arg Asp Ala Pro Ala Pro
            20                  25                  30

Thr Pro Cys Val Pro Ala Glu Cys Phe Asp Leu Leu Val Arg His Cys
        35                  40                  45

Val Ala Cys Gly Leu Leu Arg Thr Pro Arg Pro Lys Pro Ala Gly Ala
    50                  55                  60

Ser Ser Pro Ala Pro Arg Thr Ala Leu Gln Pro Gln Glu Ser Gln Val
65                  70                  75                  80

Thr Asp Lys Ala Ala His Tyr Thr Leu Cys Pro Pro Cys Pro Ala Pro
                85                  90                  95

Glu Leu Leu Gly Gly Pro Ser Val Phe Leu Phe Pro Pro Lys Pro Lys
            100                 105                 110

Asp Thr Leu Met Ile Ser Arg Thr Pro Glu Val Thr Cys Val Val Val
        115                 120                 125

Ala Val Ser His Glu Asp Pro Glu Val Lys Phe Asn Trp Tyr Val Asp
    130                 135                 140

Gly Val Glu Val His Asn Ala Lys Thr Lys Pro Arg Glu Glu Gln Tyr
145                 150                 155                 160

Asn Ser Thr Tyr Arg Val Val Ser Val Leu Thr Val Leu His Gln Asp
                165                 170                 175

Trp Leu Asn Gly Lys Glu Tyr Lys Cys Lys Val Ser Asn Lys Ala Leu
            180                 185                 190

Pro Ala Pro Ile Glu Lys Thr Ile Ser Lys Ala Lys Gly Gln Pro Arg
        195                 200                 205

Glu Pro Gln Val Tyr Thr Leu Pro Pro Ser Arg Glu Glu Met Thr Lys
    210                 215                 220

Asn Gln Val Ser Leu Thr Cys Leu Val Lys Gly Phe Tyr Pro Ser Asp
225                 230                 235                 240

Ile Ala Val Glu Trp Glu Ser Asn Gly Gln Pro Glu Asn Asn Tyr Lys
                245                 250                 255

Thr Thr Pro Pro Val Leu Asp Ser Asp Gly Ser Phe Phe Leu Tyr Ser
            260                 265                 270

Lys Leu Thr Val Asp Lys Ser Arg Trp Gln Gln Gly Asn Val Phe Ser
        275                 280                 285

Cys Ser Val Met His Glu Ala Leu His Asn His Tyr Thr Gln Lys Ser
    290                 295                 300

Leu Ser Leu Ser Pro Gly Lys
305                 310

<210> SEQ ID NO 27
<211> LENGTH: 29
<212> TYPE: DNA
<213> ORGANISM: Artificial Sequence
<220> FEATURE:
<223> OTHER INFORMATION: Primer sequence

<400> SEQUENCE: 27

```
tattaggccg gccaccatgg atgcaatga                                            29

<210> SEQ ID NO 28
<211> LENGTH: 29
<212> TYPE: DNA
<213> ORGANISM: Artificial Sequence
<220> FEATURE:
<223> OTHER INFORMATION: Primer sequence

<400> SEQUENCE: 28
tgaagatttg ggctccttga gacctggga                                            29

<210> SEQ ID NO 29
<211> LENGTH: 29
<212> TYPE: DNA
<213> ORGANISM: Artificial Sequence
<220> FEATURE:
<223> OTHER INFORMATION: Primer sequence

<400> SEQUENCE: 29
tcccaggtct caaggagccc aaatcttca                                            29

<210> SEQ ID NO 30
<211> LENGTH: 36
<212> TYPE: DNA
<213> ORGANISM: Artificial Sequence
<220> FEATURE:
<223> OTHER INFORMATION: Primer sequence

<400> SEQUENCE: 30
taattggcgc gcctctagat tatttacccg gagaca                                    36

<210> SEQ ID NO 31
<211> LENGTH: 30
<212> TYPE: DNA
<213> ORGANISM: Artificial Sequence
<220> FEATURE:
<223> OTHER INFORMATION: Primer sequence

<400> SEQUENCE: 31
tgaagatttg ggctcgttct cacagaagta                                           30

<210> SEQ ID NO 32
<211> LENGTH: 31
<212> TYPE: DNA
<213> ORGANISM: Artificial Sequence
<220> FEATURE:
<223> OTHER INFORMATION: Primer sequence

<400> SEQUENCE: 32
atacttctgt gagaacgagc ccaaatcttc a                                         31

<210> SEQ ID NO 33
<211> LENGTH: 30
<212> TYPE: DNA
<213> ORGANISM: Artificial Sequence
<220> FEATURE:
<223> OTHER INFORMATION: Primer sequence

<400> SEQUENCE: 33
tttgggctcg ctcctgagct tgttctcaca                                           30

<210> SEQ ID NO 34
<211> LENGTH: 28
<212> TYPE: DNA
```

<213> ORGANISM: Artificial Sequence
<220> FEATURE:
<223> OTHER INFORMATION: Primer sequence

<400> SEQUENCE: 34
ctcaggagcg agcccaaatc ttcagaca                                28

<210> SEQ ID NO 35
<211> LENGTH: 26
<212> TYPE: DNA
<213> ORGANISM: Artificial Sequence
<220> FEATURE:
<223> OTHER INFORMATION: Primer sequence

<400> SEQUENCE: 35
tttgggctcc ctgagctctg gtggaa                                  26

<210> SEQ ID NO 36
<211> LENGTH: 28
<212> TYPE: DNA
<213> ORGANISM: Artificial Sequence
<220> FEATURE:
<223> OTHER INFORMATION: Primer sequence

<400> SEQUENCE: 36
gagctcaggg agcccaaatc ttcagaca                                28

<210> SEQ ID NO 37
<211> LENGTH: 1216
<212> TYPE: DNA
<213> ORGANISM: homo sapiens
<220> FEATURE:
<221> NAME/KEY: CDS
<222> LOCATION: (141)...(890)

<400> SEQUENCE: 37
gaattcggct cgagcctttt tatttctcct tgcgtaacaa ccttcttccc ttctgcacca    60
ctgcccgtac ccttacccgc cccgccacct ccttgctacc ccactcttga aaccacagct   120
gttggcaggg tccccagctc atg cca gcc tca tct cct ttc ttg cta gcc ccc  173
                         Met Pro Ala Ser Ser Pro Phe Leu Leu Ala Pro
                          1               5                  10 aaa ggg cct cca ggc aac atg ggg ggc cca gtc aga gag ccg gca ctc    221
Lys Gly Pro Pro Gly Asn Met Gly Gly Pro Val Arg Glu Pro Ala Leu
         15                  20                  25 tca gtt gcc ctc tgg ttg agt tgg ggg gca gct ctg ggg gcc gtg gct    269
Ser Val Ala Leu Trp Leu Ser Trp Gly Ala Ala Leu Gly Ala Val Ala
 30                  35                  40 tgt gcc atg gct ctg ctg acc caa caa aca gag ctg cag agc ctc agg    317
Cys Ala Met Ala Leu Leu Thr Gln Gln Thr Glu Leu Gln Ser Leu Arg
             45                  50                  55 aga gag gtg agc cgg ctg cag ggg aca gga ggc ccc tcc cag aat ggg    365
Arg Glu Val Ser Arg Leu Gln Gly Thr Gly Gly Pro Ser Gln Asn Gly
 60                  65                  70                  75 gaa ggg tat ccc tgg cag agt ctc ccg gag cag agt tcc gat gcc ctg    413
Glu Gly Tyr Pro Trp Gln Ser Leu Pro Glu Gln Ser Ser Asp Ala Leu
                 80                  85                  90 gaa gcc tgg gag aat ggg gag aga tcc cgg aaa agg aga gca gtg ctc    461
Glu Ala Trp Glu Asn Gly Glu Arg Ser Arg Lys Arg Arg Ala Val Leu
             95                 100                 105 acc caa aaa cag aag aag cag cac tct gtc ctg cac ctg gtt ccc att    509
Thr Gln Lys Gln Lys Lys Gln His Ser Val Leu His Leu Val Pro Ile
        110                 115                 120

```
aac gcc acc tcc aag gat gac tcc gat gtg aca gag gtg atg tgg caa      557
Asn Ala Thr Ser Lys Asp Asp Ser Asp Val Thr Glu Val Met Trp Gln
        125                 130                 135 cca gct ctt agg cgt ggg aga ggc cta cag gcc caa gga tat ggt gtc      605
Pro Ala Leu Arg Arg Gly Arg Gly Leu Gln Ala Gln Gly Tyr Gly Val
140                 145                 150                 155 cga atc cag gat gct gga gtt tat ctg ctg tat agc cag gtc ctg ttt      653
Arg Ile Gln Asp Ala Gly Val Tyr Leu Leu Tyr Ser Gln Val Leu Phe
                160                 165                 170 caa gac gtg act ttc acc atg ggt cag gtg gtg tct cga gaa ggc caa      701
Gln Asp Val Thr Phe Thr Met Gly Gln Val Val Ser Arg Glu Gly Gln
            175                 180                 185 gga agg cag gag act cta ttc cga tgt ata aga agt atg ccc tcc cac      749
Gly Arg Gln Glu Thr Leu Phe Arg Cys Ile Arg Ser Met Pro Ser His
        190                 195                 200 ccg gac cgg gcc tac aac agc tgc tat agc gca ggt gtc ttc cat tta      797
Pro Asp Arg Ala Tyr Asn Ser Cys Tyr Ser Ala Gly Val Phe His Leu
    205                 210                 215 cac caa ggg gat att ctg agt gtc ata att ccc cgg gca agg gcg aaa      845
His Gln Gly Asp Ile Leu Ser Val Ile Ile Pro Arg Ala Arg Ala Lys
220                 225                 230                 235 ctt aac ctc tct cca cat gga acc ttc ctg ggg ttt gtg aaa ctg          890
Leu Asn Leu Ser Pro His Gly Thr Phe Leu Gly Phe Val Lys Leu
                240                 245                 250 tgattgtgtt ataaaaagtg gctcccagct tggaagacca gggtgggtac atactggaga    950
cagccaagag ctgagtatat aaaggagagg gaatgtgcag gaacagaggc gtcttcctgg    1010
gtttggctcc ccgttcctca cttttccctt ttcattccca cccccctagac tttgatttta   1070 cggatatctt gcttctgttc cccatggagc tccgaattct tgcgtgtgtg tagatgaggg    1130 gcggggacg ggcgccaggc attgttcaga cctggtcggg gcccactgga agcatccaga    1190
acagcaccac catctagcgg ccgccg                                         1216

<210> SEQ ID NO 38
<211> LENGTH: 250
<212> TYPE: PRT
<213> ORGANISM: homo sapiens

<400> SEQUENCE: 38

Met Pro Ala Ser Ser Pro Phe Leu Leu Ala Pro Lys Gly Pro Gly
 1               5                  10                  15

Asn Met Gly Gly Pro Val Arg Glu Pro Ala Leu Ser Val Ala Leu Trp
                20                  25                  30

Leu Ser Trp Gly Ala Ala Leu Gly Ala Val Ala Cys Ala Met Ala Leu
            35                  40                  45

Leu Thr Gln Gln Thr Glu Leu Gln Ser Leu Arg Arg Glu Val Ser Arg
 50                  55                  60

Leu Gln Gly Thr Gly Gly Pro Ser Gln Asn Gly Glu Gly Tyr Pro Trp
 65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
                100                 105                 110

Lys Gln His Ser Val Leu His Leu Val Pro Ile Asn Ala Thr Ser Lys
            115                 120                 125

Asp Asp Ser Asp Val Thr Glu Val Met Trp Gln Pro Ala Leu Arg Arg
130                 135                 140
```

```
Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 39
<211> LENGTH: 762
<212> TYPE: DNA
<213> ORGANISM: homo sapiens
<220> FEATURE:
<221> NAME/KEY: CDS
<222> LOCATION: (7)...(759)

<400> SEQUENCE: 39 ggatcc atg aag cac ctg tgg ttc ttc ctc ctg ctg gtg gcg gct ccc         48
       Met Lys His Leu Trp Phe Phe Leu Leu Leu Val Ala Ala Pro
         1               5                  10 aga tgg gtc ctg tcc gag ccc aaa tct tgt gac aaa act cac aca tgc        96
Arg Trp Val Leu Ser Glu Pro Lys Ser Cys Asp Lys Thr His Thr Cys
 15                  20                  25                  30 cca ccg tgc cca gca cct gaa ctc ctg ggg gga ccg tca gtc ttc ctc       144
Pro Pro Cys Pro Ala Pro Glu Leu Leu Gly Gly Pro Ser Val Phe Leu
                 35                  40                  45 ttc ccc cca aaa ccc aag gac acc ctc atg atc tcc cgg acc cct gag       192
Phe Pro Pro Lys Pro Lys Asp Thr Leu Met Ile Ser Arg Thr Pro Glu
             50                  55                  60 gtc aca tgc gtg gtg gtg gac gtg agc cac gaa gac cct gag gtc aag       240
Val Thr Cys Val Val Val Asp Val Ser His Glu Asp Pro Glu Val Lys
         65                  70                  75 ttc aac tgg tac gtg gac ggc gtg gag gtg cat aat gcc aag aca aag       288
Phe Asn Trp Tyr Val Asp Gly Val Glu Val His Asn Ala Lys Thr Lys
     80                  85                  90 ccg cgg gag gag cag tac aac agc acg tac cgt gtg gtc agc gtc ctc       336
Pro Arg Glu Glu Gln Tyr Asn Ser Thr Tyr Arg Val Val Ser Val Leu
 95                 100                 105                 110 acc gtc ctg cac cag gac tgg ctg aat ggc aag gag tac aag tgc aag       384
Thr Val Leu His Gln Asp Trp Leu Asn Gly Lys Glu Tyr Lys Cys Lys
                115                 120                 125 gtc tcc aac aaa gcc ctc cca gcc ccc atc gag aaa acc atc tcc aaa       432
Val Ser Asn Lys Ala Leu Pro Ala Pro Ile Glu Lys Thr Ile Ser Lys
            130                 135                 140 gcc aaa ggg cag ccc cga gaa cca cag gtg tac acc ctg ccc cca tcc       480
Ala Lys Gly Gln Pro Arg Glu Pro Gln Val Tyr Thr Leu Pro Pro Ser
        145                 150                 155 cgg gat gag ctg acc aag aac cag gtc agc ctg acc tgc ctg gtc aaa       528
Arg Asp Glu Leu Thr Lys Asn Gln Val Ser Leu Thr Cys Leu Val Lys
    160                 165                 170 ggc ttc tat ccc agc gac atc gcc gtg gag tgg gag agc aat ggg cag       576
Gly Phe Tyr Pro Ser Asp Ile Ala Val Glu Trp Glu Ser Asn Gly Gln
175                 180                 185                 190
```

```
ccg gag aac aac tac aag acc acg cct ccc gtg ctg gac tcc gac ggc      624
Pro Glu Asn Asn Tyr Lys Thr Thr Pro Pro Val Leu Asp Ser Asp Gly
            195                 200                 205 tcc ttc ttc ctc tac agc aag ctc acc gtg gac aag agc agg tgg cag      672
Ser Phe Phe Leu Tyr Ser Lys Leu Thr Val Asp Lys Ser Arg Trp Gln
        210                 215                 220 cag ggg aac gtc ttc tca tgc tcc gtg atg cat gag gct ctg cac aac      720
Gln Gly Asn Val Phe Ser Cys Ser Val Met His Glu Ala Leu His Asn
    225                 230                 235 cac tac acg cag aag agc ctc tcc ctg tct ccg ggt aaa tga              762
His Tyr Thr Gln Lys Ser Leu Ser Leu Ser Pro Gly Lys
240                 245                 250

<210> SEQ ID NO 40
<211> LENGTH: 251
<212> TYPE: PRT
<213> ORGANISM: homo sapiens

<400> SEQUENCE: 40

Met Lys His Leu Trp Phe Phe Leu Leu Leu Val Ala Ala Pro Arg Trp
1               5                   10                  15

Val Leu Ser Glu Pro Lys Ser Cys Asp Lys Thr His Thr Cys Pro Pro
            20                  25                  30

Cys Pro Ala Pro Glu Leu Leu Gly Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Lys Phe Asn
65                  70                  75                  80

Trp Tyr Val Asp Gly Val Glu Val His Asn Ala Lys Thr Lys Pro Arg
                85                  90                  95

Glu Glu Gln Tyr Asn Ser Thr Tyr Arg Val Val Ser Val Leu Thr Val
            100                 105                 110

Leu His Gln Asp Trp Leu Asn Gly Lys Glu Tyr Lys Cys Lys Val Ser
        115                 120                 125

Asn Lys Ala Leu Pro Ala Pro Ile Glu Lys Thr Ile Ser Lys Ala Lys
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
    210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 41
<211> LENGTH: 35
<212> TYPE: PRT
<213> ORGANISM: Artificial Sequence
<220> FEATURE:
```

```
<223> OTHER INFORMATION: Optimized tPA leader

<400> SEQUENCE: 41

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg
        35
```